(12) United States Patent
Wang et al.

(10) Patent No.: US 7,872,101 B1
(45) Date of Patent: Jan. 18, 2011

(54) MODULATORS OF THE ORPHAN G PROTEIN-COUPLED RECEPTORS GPR78 AND GPR26

(75) Inventors: Suke Wang, Edison, NJ (US); Frederick James Monsma, Jr., Summit, NJ (US); Xiaoxin Yang, Livingston, NJ (US); Eric L. Gustafson, Annandale, NJ (US); Maureen Laverty, Old Bridge, NJ (US); Elizabeth B. Smith, Princeton, NJ (US)

(73) Assignee: Schering Corporation, Kenilworth, NJ (US)

( * ) Notice: Subject to any disclaimer, the term of this patent is extended or adjusted under 35 U.S.C. 154(b) by 235 days.

(21) Appl. No.: 11/949,306

(22) Filed: Dec. 3, 2007

Related U.S. Application Data

(60) Provisional application No. 60/872,124, filed on Dec. 1, 2006.

(51) Int. Cl.
C07K 14/00 (2006.01)
(52) U.S. Cl. .................................. 530/350; 530/402
(58) Field of Classification Search ................. None
See application file for complete search history.

(56) References Cited

U.S. PATENT DOCUMENTS

| | | | |
|---|---|---|---|
| 2004/0197825 A1 | 10/2004 | Karicheti et al. | |
| 2006/0134109 A1 | 6/2006 | Gaitanaris et al. | |
| 2009/0048200 A1* | 2/2009 | Hendrick et al. | 514/44 |

FOREIGN PATENT DOCUMENTS

| | | | |
|---|---|---|---|
| WO | WO 2005/093091 | * | 10/2005 |
| WO | WO 2007/049059 | | 5/2007 |

OTHER PUBLICATIONS

Akiyama, T. et al., "Genistein, a specific inhibitor of tyrosine-specific protein kinases," *J. Biol. Chem.* 262(12):5592-5 (1987).
Albertazzi, P. et al., "Effect of pure genistein on bone markers and hot flushes," *Climacteric* 8(4):371-9 (2005).
Altavilla, D. et al, "Cardiovascular effects of the phytoestrogen genistein," *Curr. Med. Chem. Cardiovasc. Hematol. Agents* 2(2):179-86 (2004).
Ariazi, E.A. et al., "Estrogen-related receptors as emerging targets in cancer and metabolic disorders," *Curr. Top. Med. Chem.* 6(3):181-193 (2006).
Arjmandi, B., "The Role of Phytoestrogens in the Prevention and Treatment of Osteoporosis in Ovarian Hormone Deficiency," Journal of the American College of Nutrition, 20(5) 398S-402S (2001).
Barnes, S., "Effect of Genistein on In Vitro and In Vivo Models of Cancer," *American Institute of Nutrition* 125(3Suppl): 777S-783S (1995).
Behbod, F. et al., "Concomitant inhibition of Janus kinase 3 and calcineurin-dependent signaling pathways synergistically prolongs the survival of rat heart allografts," *J. Immunol.* 166(6):3724-32 (2001).

Bektic, J. et al "Molecular effects of the isoflavonoid genistein in prostate cancer," *Clin. Prostate Cancer* 4(2)124-9 (2005).
Bilder, G.E. et al., "Tyrphostins inhibit PDGF-induced DNA synthesis and associated early events in smooth muscle cells," *Am. J. Physiol.* 260(4 Pt 1):C721-30 (1991).
Bresnick, J.N. et al., "Identification of signal transduction pathways used by orphan g protein-coupled receptors," *Assay Drug Dev. Technol.* 1(2):239-49 (2003).
Chijiwa, T. et al., "Inhibition of forskolin-induced neurite outgrowth and protein phosphorylation by a newly synthesized selective inhibitor of cyclic AMP-dependent protein kinase, N-[2-(p-bromocinnamylamino)ethyl]-5-isoquinolinesulfonamide (H-89), of PC12D pheochromocytoma cells," *J. Biol. Chem.* 265(9):5267-72 (1990).
Cockerill. G et al., "Angiogenesis: Models and Modulators," *Inter. Review of Cytology*, 159:113-160 (1995).
Cotter, A. et al., "Genistein appears to prevent early postmenopausal bone loss as effectively as hormone replacement therapy" *Nutr. Rev.* 61(10):346-51 (2003).
Cross, A.R. et al., "The effect of the inhibitor diphenylene iodonium on the superoxide-generating system of neutrophils. Specific labelling of a component polypeptide of the oxidase," *Biochem. J.* 237:111-116 (1986).
Cruz, M.N. et al., "Acute responses to phytoestrogens in small arteries from men with coronary heart disease," *Am. J. Physicol. Heart Circ. Physiol.* 290(5):H1969-75 (2006).
Das, M. et al, "Clinicoepidemiological, toxicological, and safety evaluation studies on argemone oil," *Crit. Rev. Toxicol.* 27(3):273-297 (1997).
Dubey, R.K. et al., "Phytoestrogens inhibit growth and MAP kinase activity in human aortic smooth muscle cells," *Hypertension* 33(1 Pt 2):177-82 (1999).
Fotsis, T. et al., "Genistein, a dietary ingested isoflavonoid, inhibits cell proliferation and in vitro angiogenesis," *J. Nutr.* 125(3 Suppl):790S-797S (1995).
Geissler, J.F. et al., "Thiazolidine-diones. Biochemical and biological activity of a novel class of tyrosine protein kinase inhibitors," *J. Biol. Chem.* 265(36):22255-61 (1990).
Gupte et al., "Elucidation of signaling properties of vasopressin receptor-related receptor 1 by using the chimeric receptor approach," *Proc. Natl. Acad. Sci. USA* 101(6):1508-13 (2004).
Hancock, J.T. et al., "The inhibition by diphenyleneiodonium and its analogues of superoxide generation by macrophages," *Biochem. J.* 242:103-107 (1987).
Jiang, Y. et al., "Identification and characterization of a novel RF-amide peptide ligand for orphan G-protein-coupled receptor SP9155," *J. Biol. Chem.* 278(30):27652-7 (2003).
Kennedy, A., "The Evidence for Soybean Products as Cancer Preventive Agents," *Journal of Nutrition* 125(3 Suppl): 733S-743S (1995).

(Continued)

*Primary Examiner*—Celine X Qian

(57) ABSTRACT

The invention relates to the use of the interaction between the GPR78 polypeptide or the GPR26 polypeptide and their identified ligands and antagonists as the basis for screening methods for the identification of agents that modulate the activity of these receptors, and for diagnostic and therapeutic purposes. The agents identified by the screening methods of the invention have use in the treatment of GPR78- and/or GPR26-mediated disorders, including, but not limited to, neurological disorders (such as anxiety disorders), metabolic disorders, cardiovascular disorders, hormone-related disorders, vascular disorders and hyperproliferative disorders (such as cancer).

5 Claims, 32 Drawing Sheets

OTHER PUBLICATIONS

Kostenis, E., "Techniques: Promiscuous Gα proteins in basic research and drug discovery," *Trends in Pharmacological Sciences*, 26(11):595-602 (2005).

Kostenis E., G Proteins in Drug Screening: From Analysis of Receptor-G Protein Specificity to Manipulation of GPCR-Mediated Signalling Pathways, *Curr. Pharm. Des.* 12(14):1703-1715 (2006).

Kousidou, O. et al., "Effects of the natural isoflavonoid genistein on growth, signaling pathways and gene expression of matrix macromolecules by breast cancer cells," *Mini Rev. Med. Chem.* 6(3):331-7 (2006).

Lee, D.K. et al., "Cloning and characterization of additional members of the G protein-coupled receptor family," *Biochim. Biophys. Acta.* 1490(3):311-23 (2000).

Lee, D.K. et al., "Discovery and mapping of ten novel G protein-coupled receptor genes," *Gene* 275(1):83-91 (2001).

Lee, J.S., "Effects of soy protein and genistein on blood glucose, antioxidant enzyme activities, and lipid profile in streptozotocin-induced diabetic rats," *Life Sci.* 79:1578-84 (2006).

Lephart, E.D. et al., "Neurobehavioral effects of dietary soy phytoestrogens," *Neurotoxicol. Teratol.* 24(1):5-16 (2002).

Lephart, E.D. et al.,"Stress (hypothalamic-pituitary-adrenal axis) and pain response in male rats exposed lifelong to high vs. low phytoestrogen diets," *Neurosci. Lett.* 342(1-2):65-8 (2003).

Lippe, C. et al, "Actions of vasopressin and isoprenaline on the ionic transport across the isolated frog skin in the presence and the absence of adenyl cyclase inhibitors MDL12330A and SQ22536," *Comp. Biochem. Physiol. C.* 99(1/2)209-11 (1991).

Liu, D. et al., "Genistein acutely stimulates nitric oxide synthesis in vascular endothelial cells by a cyclic adenosine 5'-monophosphate-dependent mechanism," *Endocrinology* 145(12):5532-9 (2004).

Liu, D. et al., "Genistein activates the 3',5'-cyclic adenosine monophosphate signaling pathway in vascular endothelial cells and protects endothelial barrier function," *Endocrinology* 146(3):1312-20 (2005).

Liu, D. et al., "Genistein acutely stimulates insulin secretion in pancreatic beta-cells through a cAMP-dependent protein kinase pathway," *Diabetes* 55(4):1043-50 (2006).

Lopus, M. et al., "The benzophenanthridine alkaloid sanguinarine perturbs microtubule assembly dynamics through tubulin binding. A possible mechanism for its antiproliferative activity," *FEBS J.* 273(10):2139-2150 (2006).

Lund, T.D. et al., "Dietary soy phytoestrogens produce anxiolytic effects in the elevated plus-maze," *Brain Res.* 913(2):180-4 (2001).

Maggiolini, M. et al., "The G protein-coupled receptor GPR30 mediates c-fos up-regulation by 17beta-estradiol and phytoestrogens in breast cancer cells," *J. Biol. Chem.* 279(26):27008-16 (2004).

Nakashima, S. et al., "Genistein, a protein tyrosine kinase inhibitor, inhibits thromboxane A2-mediated human platelet responses," *Mol. Pharmacol.* 39(4):475-80 (1990).

New, D., et al., "Characterization of CHO Cells Stably Expressing a Gα 16/z Chimera for High Throughput Screening of GPCRs", *Assay Drug Dev. Techol.* 2(3):269-280 (2004).

Pan, Y. et al., "Effect of estradiol and soy phytoestrogens on choline acetyltransferase and nerve growth factor mRNAs in teh frontal cortex and hippocampus of female rats," *Proc. Soc. Exp. Biol. Med.* 221(2):118-25 (1999).

Parker, E. et al., "Cloning and characterization of the rate GALR1 galanin receptor from Rin14B insulinoma cells," *Mol. Brain Res.* 34:179-189 (1995).

Peterson, G., "Evaluation of the Biochemical Targets of Genistein in Tumor Cells," *Journal of Nutrition* 125(3 Suppl):784S-789S (1995).

Revankar, C.M. et al., "A transmembrane intracellular estrogen receptor mediates rapid cell signaling," *Science* 307:1625-30 (2005).

Rufer, C.E. et al., "Antioxidant activity of isoflavones and their major metabolites using different in vitro assays," *J. Agric. Food Chem.* 54(8):2926-31 (2006).

Sarkar, F.H., et al., "The role of genistein and synthetic derivatives of isoflavone in cancer prevention and therapy," *Mini Rev. Med. Chem.* 6(4):401-7 (2006).

Sethi, T. et al., "Galanin Stimulates $Ca^{2+}$Mobilization, Inositol Phosphate Accumulation, and Clonal Growth in Small Cell Lung Cancer Cells," *Cancer Research* 51:1674-1679 (1991).

Shively, C.A. et al., "Soy and social stress affect serotonin neurotransmission in primates," *Pharmacogenomics J.* 3(2):114-21 (2003).

Simon, N.G. et al., "Increased aggressive behavior and decreased affiliative behavior in adult male monkeys after long-term consumption of diets rich in soy protein and isoflavones," *Horm. Behav.* 45(4):278-84 (2004).

Stuehr, D.J. et al., "inhibition of macrophage and endothelial cell nitric oxide synthase by diphenylenelodonium and its analogs," *FASEB J.* 5:98-103 (1991).

Szkudelski, T. et al, "Genistein restricts leptin secretion from rat adipocytes," *J. Steroid Biochem. Mol. Biol.* 96(3-4):301-7 (2005).

Thomas, P. et al., "Identity of an estrogen membrane receptor coupled to a G protein in human breast cancer cells," *Endocrinology* 146(2):624-32 (2005).

Underwood, S.L. et al., "Association analysis of the chromosome 4p-located G protein-coupled receptor 78 (GPR78) gene in bipolar affective disorder and schizophrenia," *Mol. Psychiatry* 11(4):384-94 (2006).

Valachovicova, T. et al, "Cellular and physiological effects of soy flavonoids," *Mini Rev. Med. Chem.* 4(8):881-7 (2004).

Walterova, D. et al., "Benzo[c]phenanthridine alkaloids sanguinarine and chelerythrine: biological activities and dental care applications," *Acta Univ. Palacky Olomuc Fac. Med.* 139:7-16 (1995).

Wang, S., et al., "Differential intracellular Signaling of the GaIR1 and GaIR2 Galanin Receptor Subtypes", *Biochemistry* 37(19):6711-6717 (1998).

Wilcox, J., et al., "Thrombotic Mechanisms in Atherosclerosis: Potential Impact of Soy Proteins," *Journal of Nutrition*, 125(3 Suppl.)631S-638S (1995).

Xu, Y.L. et al, "Neuropeptide S: a neuropeptide promoting arousal and anxiolytic-like effects," *Neuron* 43(4):487-97 (2004).

Yanaihara, N., "Galanin analogues: agonist and antagonist", *Regulatory Peptides*, 46:93-101 (1993).

Yin, D., et al, "Probing. Receptor Structure/Function with Chimeric G-Protein-Coupled Receptors," *Molecular Pharmacology*, 65(6)1323-1332 (2004).

Zhang, F., et al., "ADP Is the Cognate Ligand for the Orphan G Protein-coupled Receptor SP1999." *J. of Biol, Chem.* 276(11):8608-8615 (2001).

"Quaternary isoquinoline alkaloids sanguinarine and chelerythrine. In vitro and in vivo effects," *Chemicke Listy* 100(1):30-41 (2006). (English Abstract attached).

* cited by examiner (A)

(B)

(A)

(B)

SEQUENCE LISTING

<160> NUMBER OF SEQ ID NOS: 8

<210> SEQ ID NO 1
<211> LENGTH: 363

```
<212> TYPE: PRT
<213> ORGANISM: Homo sapiens

<400> SEQUENCE: 1

Met Gly Pro Gly Glu Ala Leu Leu Ala Gly Leu Leu Val Met Val Leu
1               5                   10                  15

Ala Val Ala Leu Leu Ser Asn Ala Leu Val Leu Leu Cys Cys Ala Tyr
            20                  25                  30

Ser Ala Glu Leu Arg Thr Arg Ala Ser Gly Val Leu Leu Val Asn Leu
        35                  40                  45

Ser Leu Gly His Leu Leu Leu Ala Ala Leu Asp Met Pro Phe Thr Leu
    50                  55                  60

Leu Gly Val Met Arg Gly Arg Thr Pro Ser Ala Pro Gly Ala Cys Gln
65                  70                  75                  80

Val Ile Gly Phe Leu Asp Thr Phe Leu Ala Ser Asn Ala Ala Leu Ser
                85                  90                  95

Val Ala Ala Leu Ser Ala Asp Gln Trp Leu Ala Val Gly Phe Pro Leu
            100                 105                 110

Arg Tyr Ala Gly Arg Leu Arg Pro Arg Tyr Ala Gly Leu Leu Leu Gly
        115                 120                 125

Cys Ala Trp Gly Gln Ser Leu Ala Phe Ser Gly Ala Ala Leu Gly Cys
    130                 135                 140

Ser Trp Leu Gly Tyr Ser Ser Ala Phe Ala Ser Cys Ser Leu Arg Leu
145                 150                 155                 160

Pro Pro Glu Pro Glu Arg Pro Arg Phe Ala Ala Phe Thr Ala Thr Leu
                165                 170                 175

His Ala Val Gly Phe Val Leu Pro Leu Ala Val Leu Cys Leu Thr Ser
            180                 185                 190

Leu Gln Val His Arg Val Ala Arg Arg His Cys Gln Arg Met Asp Thr
        195                 200                 205

Val Thr Met Lys Ala Leu Ala Leu Leu Ala Asp Leu His Pro Ser Val
    210                 215                 220

Arg Gln Arg Cys Leu Ile Gln Gln Lys Arg Arg His Arg Ala Thr
225                 230                 235                 240

Arg Lys Ile Gly Ile Ala Ile Ala Thr Phe Leu Ile Cys Phe Ala Pro
                245                 250                 255

Tyr Val Met Thr Arg Leu Ala Glu Leu Val Pro Phe Val Thr Val Asn
            260                 265                 270

Ala Gln Trp Gly Ile Leu Ser Lys Cys Leu Thr Tyr Ser Lys Ala Val
        275                 280                 285

Ala Asp Pro Phe Thr Tyr Ser Leu Leu Arg Arg Pro Phe Arg Gln Val
    290                 295                 300

Leu Ala Gly Met Val His Arg Leu Leu Lys Arg Thr Pro Arg Pro Ala
305                 310                 315                 320

Ser Thr His Asp Ser Ser Leu Asp Val Ala Gly Met Val His Gln Leu
                325                 330                 335

Leu Lys Arg Thr Pro Arg Pro Ala Ser Thr His Asn Gly Ser Val Asp
            340                 345                 350

Thr Glu Asn Asp Ser Cys Leu Gln Gln Thr His
        355                 360

<210> SEQ ID NO 2
<211> LENGTH: 7512
<212> TYPE: PRT
<213> ORGANISM: Homo sapiens
```

-continued

<400> SEQUENCE: 2

```
Cys Gly Cys Cys Ala Thr Gly Gly Cys Gly Gly Cys Gly Cys Cys Gly
1               5                   10                  15

Gly Gly Thr Thr Gly Cys Gly Gly Ala Cys Cys Cys Thr Gly Ala Cys
            20                  25                  30

Gly Cys Cys Gly Gly Cys Gly Cys Gly Gly Gly Gly Cys Gly Cys Gly
        35                  40                  45

Cys Ala Cys Cys Ala Thr Gly Ala Ala Cys Thr Cys Gly Thr Gly Gly
    50                  55                  60

Gly Ala Cys Gly Cys Gly Gly Gly Cys Cys Thr Gly Gly Cys Gly Gly
65                  70                  75                  80

Gly Gly Cys Thr Ala Cys Thr Gly Gly Thr Gly Gly Gly Cys Ala Cys
                85                  90                  95

Gly Ala Thr Gly Gly Gly Cys Gly Thr Cys Thr Cys Gly Cys Thr Gly
            100                 105                 110

Cys Thr Gly Thr Cys Cys Ala Ala Cys Gly Cys Gly Cys Thr Gly Gly
        115                 120                 125

Thr Gly Cys Thr Gly Cys Thr Cys Thr Gly Cys Cys Thr Gly Cys Thr
    130                 135                 140

Gly Cys Ala Cys Ala Gly Cys Gly Cys Gly Gly Ala Cys Ala Thr Cys
145                 150                 155                 160

Cys Gly Cys Cys Gly Cys Cys Ala Gly Gly Cys Gly Cys Cys Gly Gly
                165                 170                 175

Cys Gly Cys Thr Cys Thr Thr Cys Ala Cys Cys Cys Thr Gly Ala Ala
            180                 185                 190

Cys Cys Thr Cys Ala Cys Gly Thr Gly Cys Gly Gly Gly Ala Ala Cys
        195                 200                 205

Cys Thr Gly Cys Thr Gly Thr Gly Cys Ala Cys Cys Gly Thr Gly Gly
    210                 215                 220

Thr Cys Ala Ala Cys Ala Thr Gly Cys Cys Gly Cys Thr Cys Ala Cys
225                 230                 235                 240

Gly Cys Thr Gly Gly Cys Cys Gly Gly Cys Gly Thr Cys Gly Thr Gly
                245                 250                 255

Gly Cys Gly Cys Ala Gly Cys Gly Gly Cys Ala Gly Cys Cys Gly Gly
            260                 265                 270

Cys Gly Gly Gly Cys Gly Ala Cys Cys Gly Cys Cys Thr Gly Thr Gly
        275                 280                 285

Cys Cys Gly Cys Cys Thr Gly Gly Cys Thr Gly Cys Cys Thr Thr Cys
    290                 295                 300

Cys Thr Cys Gly Ala Cys Ala Cys Cys Thr Thr Cys Cys Thr Gly Gly
305                 310                 315                 320

Cys Thr Gly Cys Cys Ala Ala Cys Thr Cys Cys Ala Thr Gly Cys Thr
                325                 330                 335

Cys Ala Gly Cys Ala Thr Gly Gly Cys Cys Gly Cys Gly Cys Thr Cys
            340                 345                 350

Ala Gly Cys Ala Thr Cys Gly Ala Cys Cys Gly Cys Thr Gly Gly Gly
        355                 360                 365

Thr Gly Gly Cys Cys Gly Thr Gly Gly Thr Cys Thr Thr Cys Cys Cys
    370                 375                 380

Gly Cys Thr Gly Ala Gly Cys Thr Ala Cys Cys Gly Gly Gly Cys Cys
385                 390                 395                 400

Ala Ala Gly Ala Thr Gly Cys Gly Cys Cys Thr Cys Cys Gly Cys Gly
```

-continued

```
                405                 410                 415
Ala Cys Gly Cys Gly Cys Gly Cys Thr Cys Ala Thr Gly Gly Thr
            420                 425                 430
Gly Gly Cys Cys Thr Ala Cys Ala Cys Gly Thr Gly Gly Cys Thr Gly
            435                 440                 445
Cys Ala Cys Gly Cys Gly Cys Thr Cys Ala Cys Cys Thr Thr Cys Cys
            450                 455                 460
Cys Ala Gly Cys Cys Gly Cys Gly Cys Gly Cys Thr Cys Thr Gly Cys
465                 470                 475                 480
Cys Cys Thr Gly Thr Cys Cys Thr Gly Gly Cys Thr Cys Gly Gly Cys
            485                 490                 495
Thr Thr Cys Cys Ala Cys Cys Ala Gly Cys Thr Gly Thr Ala Cys Gly
            500                 505                 510
Cys Cys Thr Cys Gly Thr Gly Cys Ala Cys Gly Cys Thr Gly Thr Gly
            515                 520                 525
Cys Ala Gly Cys Cys Gly Gly Cys Gly Gly Cys Cys Gly Gly Ala Cys
            530                 535                 540
Gly Ala Gly Cys Gly Cys Cys Thr Gly Cys Gly Cys Thr Thr Cys Gly
545                 550                 555                 560
Cys Cys Gly Thr Cys Thr Thr Cys Ala Cys Thr Gly Gly Cys Gly Cys
            565                 570                 575
Cys Thr Thr Cys Cys Ala Cys Gly Cys Thr Cys Thr Cys Ala Gly Cys
            580                 585                 590
Thr Thr Cys Cys Thr Gly Cys Thr Cys Thr Cys Thr Thr Cys Thr Gly
            595                 600                 605
Thr Cys Gly Thr Gly Cys Thr Cys Thr Gly Thr Gly Cys Ala Cys
            610                 615                 620
Gly Thr Ala Cys Cys Thr Cys Ala Ala Gly Gly Thr Gly Cys Thr Cys
625                 630                 635                 640
Ala Ala Gly Gly Thr Gly Gly Cys Cys Gly Cys Thr Thr Cys Cys
            645                 650                 655
Ala Thr Thr Gly Cys Ala Ala Gly Cys Gly Cys Ala Thr Cys Gly Ala
            660                 665                 670
Cys Gly Thr Gly Ala Thr Cys Ala Cys Ala Thr Gly Cys Ala Gly
            675                 680                 685
Ala Cys Gly Cys Thr Cys Gly Thr Gly Cys Thr Gly Cys Thr Gly Gly
            690                 695                 700
Thr Gly Gly Ala Cys Cys Thr Gly Cys Ala Cys Cys Cys Cys Ala Gly
705                 710                 715                 720
Thr Gly Thr Gly Cys Gly Gly Gly Ala Ala Cys Gly Cys Thr Gly Thr
                725                 730                 735
Cys Thr Gly Gly Ala Gly Gly Ala Gly Cys Ala Gly Ala Ala Gly Cys
            740                 745                 750
Gly Gly Ala Gly Gly Cys Gly Ala Cys Ala Gly Cys Gly Ala Gly Cys
            755                 760                 765
Cys Ala Cys Cys Ala Ala Gly Ala Ala Gly Ala Thr Cys Ala Gly Cys
            770                 775                 780
Ala Cys Cys Thr Thr Cys Ala Thr Ala Gly Gly Ala Cys Cys Thr
785                 790                 795                 800
Thr Cys Cys Thr Thr Gly Thr Gly Thr Gly Cys Thr Thr Cys Gly Cys
            805                 810                 815
Gly Cys Cys Cys Thr Ala Thr Gly Thr Gly Ala Thr Cys Ala Cys Cys
            820                 825                 830
```

-continued

```
Ala Gly Gly Cys Thr Ala Gly Thr Gly Gly Ala Gly Cys Thr Cys Thr
        835                 840                 845
Thr Cys Thr Cys Cys Ala Cys Gly Gly Thr Gly Cys Cys Ala Thr
        850                 855                 860
Cys Gly Gly Cys Thr Cys Cys Ala Cys Thr Gly Gly Gly Gly
865                 870                 875                 880
Gly Thr Gly Cys Thr Gly Thr Cys Cys Ala Ala Gly Thr Gly Cys Thr
                    885                 890                 895
Thr Gly Gly Cys Gly Thr Ala Cys Ala Gly Cys Ala Ala Gly Gly Cys
                900                 905                 910
Cys Gly Cys Ala Thr Cys Cys Gly Ala Cys Cys Cys Thr Thr Thr
        915                 920                 925
Gly Thr Gly Thr Ala Cys Thr Cys Cys Thr Thr Ala Cys Thr Gly Cys
        930                 935                 940
Gly Ala Cys Ala Cys Cys Ala Gly Thr Ala Cys Cys Gly Cys Ala Ala
945                 950                 955                 960
Ala Ala Gly Cys Thr Gly Cys Ala Ala Gly Gly Ala Gly Ala Thr Thr
                965                 970                 975
Cys Thr Gly Ala Ala Cys Ala Gly Gly Cys Thr Cys Thr Gly Cys
        980                 985                 990
Ala Cys Ala Gly Ala Cys Gly Cys Thr Cys Cys Ala Thr Cys Cys Ala
            995                 1000                1005
Cys Thr Cys Cys Thr Cys Thr Gly Gly Cys Cys Thr Cys Ala Cys
        1010                1015                1020
Ala Gly Gly Cys Gly Ala Cys Thr Cys Thr Cys Ala Cys Ala Gly
        1025                1030                1035
Cys Cys Ala Gly Ala Ala Cys Ala Thr Cys Thr Gly Cys Cys
        1040                1045                1050
Gly Gly Thr Gly Thr Cys Thr Gly Ala Gly Thr Gly Ala Ala Gly
        1055                1060                1065
Gly Ala Cys Cys Gly Cys Gly Cys Thr Cys Cys Thr Gly Cys Thr
        1070                1075                1080
Gly Ala Ala Gly Ala Gly Thr Thr Thr Ala Gly Ala Ala Thr Gly
        1085                1090                1095
Ala Gly Gly Cys Ala Gly Cys Gly Gly Thr Gly Ala Gly Ala Ala
        1100                1105                1110
Gly Ala Ala Gly Gly Gly Thr Gly Gly Gly Ala Gly Gly Gly Cys
        1115                1120                1125
Gly Thr Gly Gly Gly Gly Cys Cys Cys Cys Thr Gly Gly Gly
        1130                1135                1140
Thr Gly Gly Ala Cys Ala Cys Cys Ala Cys Cys Ala Gly Cys Cys
        1145                1150                1155
Ala Cys Cys Ala Gly Thr Cys Cys Cys Thr Gly Gly Cys Ala Thr
        1160                1165                1170
Gly Cys Cys Cys Ala Gly Thr Gly Ala Thr Cys Thr Gly Gly
        1175                1180                1185
Thr Thr Cys Cys Cys Thr Gly Gly Cys Thr Thr Gly Thr Ala Gly
        1190                1195                1200
Gly Gly Gly Cys Thr Cys Cys Ala Gly Ala Gly Cys Cys Thr Gly
        1205                1210                1215
Cys Thr Thr Cys Cys Thr Gly Gly Thr Thr Cys Cys Thr Cys Ala
        1220                1225                1230
```

```
Ala Gly Gly Gly Cys Ala Gly Ala Thr Ala Thr Thr Gly Gly Ala
    1235                1240                1245

Cys Ala Cys Thr Cys Cys Thr Thr Ala Thr Thr Thr Gly Thr Cys
    1250                1255                1260

Ala Cys Cys Ala Ala Gly Gly Ala Thr Gly Ala Cys Thr Gly
    1265                1270                1275

Thr Ala Gly Gly Cys Cys Thr Gly Thr Gly Cys Thr Gly Gly
    1280                1285                1290

Cys Cys Thr Thr Thr Cys Thr Thr Cys Thr Ala Ala Gly Ala
    1295                1300                1305

Ala Gly Cys Thr Gly Cys Thr Thr Gly Ala Gly Cys Thr Cys
    1310                1315                1320

Cys Thr Gly Gly Ala Cys Thr Cys Ala Cys Cys Thr Gly Ala Gly
    1325                1330                1335

Gly Cys Thr Cys Cys Thr Gly Gly Gly Gly Ala Thr Gly
    1340                1345                1350

Ala Cys Ala Cys Thr Cys Ala Gly Thr Thr Cys Thr Gly Thr Cys
    1355                1360                1365

Ala Cys Thr Gly Thr Cys Ala Ala Gly Gly Ala Thr Gly Cys Ala
    1370                1375                1380

Gly Ala Gly Ala Gly Cys Thr Gly Gly Thr Gly Gly Thr Ala Gly
    1385                1390                1395

Gly Thr Gly Gly Gly Ala Ala Gly Cys Ala Thr Gly Gly Thr Gly
    1400                1405                1410

Thr Cys Cys Ala Cys Cys Thr Gly Cys Cys Thr Gly Cys Thr Gly
    1415                1420                1425

Ala Cys Cys Ala Cys Thr Gly Gly Ala Cys Gly Cys Thr Gly Cys
    1430                1435                1440

Thr Cys Cys Ala Thr Gly Cys Thr Gly Ala Ala Gly Ala Ala Ala
    1445                1450                1455

Ala Gly Thr Gly Ala Cys Ala Gly Thr Cys Thr Cys Cys Ala Gly
    1460                1465                1470

Gly Gly Gly Ala Cys Ala Thr Thr Thr Cys Ala Gly Cys Cys Ala
    1475                1480                1485

Thr Gly Cys Thr Gly Ala Ala Ala Gly Gly Gly Ala Gly Gly Cys
    1490                1495                1500

Thr Gly Gly Cys Ala Gly Thr Gly Gly Thr Cys Ala Thr Thr Thr
    1505                1510                1515

Gly Gly Cys Cys Cys Gly Gly Ala Thr Cys Thr Ala Ala Cys Ala
    1520                1525                1530

Thr Gly Gly Cys Ala Cys Cys Thr Cys Gly Thr Cys Thr Cys Cys
    1535                1540                1545

Ala Cys Ala Gly Gly Gly Thr Ala Gly Thr Gly Gly Thr Gly Gly
    1550                1555                1560

Cys Thr Gly Cys Thr Thr Cys Ala Ala Cys Cys Cys Ala Ala Ala
    1565                1570                1575

Thr Ala Thr Thr Ala Thr Thr Cys Ala Gly Cys Thr Gly Gly Thr
    1580                1585                1590

Ala Cys Thr Ala Ala Cys Gly Ala Cys Ala Thr Gly Thr Gly
    1595                1600                1605

Cys Cys Cys Ala Gly Cys Thr Gly Gly Gly Ala Cys Thr Cys Thr
    1610                1615                1620

Thr Gly Gly Gly Cys Thr Cys Thr Gly Thr Gly Cys Cys Thr Gly
```

-continued

```
    1625                1630                1635

Ala Gly  Gly Gly Ala Ala Ala  Ala Thr Gly Thr Thr  Thr Cys Ala
    1640                1645                1650

Cys Ala  Ala Cys Thr Ala Gly  Thr Gly Gly Cys Thr  Gly Cys Cys
    1655                1660                1665

Cys Ala  Ala Thr Thr Gly Cys  Thr Gly Cys Thr Gly  Ala Cys Cys
    1670                1675                1680

Ala Gly  Thr Thr Gly Thr Cys  Thr Thr Ala Gly Ala  Ala Ala Thr
    1685                1690                1695

Gly Gly  Thr Cys Ala Ala Thr  Thr Gly Gly Ala Thr  Thr Cys Ala
    1700                1705                1710

Ala Cys  Thr Thr Thr Ala Gly  Thr Cys Cys Thr Cys  Thr Cys Cys
    1715                1720                1725

Thr Thr  Cys Cys Cys Cys Cys  Thr Ala Ala Ala Ala  Gly Cys Gly
    1730                1735                1740

Ala Ala  Thr Gly Thr Thr Thr  Gly Thr Gly Thr Gly  Thr Gly Cys
    1745                1750                1755

Ala Gly  Ala Cys Ala Ala Thr  Cys Thr Thr Ala Gly  Cys Ala Thr
    1760                1765                1770

Gly Ala  Ala Ala Ala Thr Gly  Gly Thr Thr Thr Ala  Ala Ala Thr
    1775                1780                1785

Ala Gly  Gly Cys Thr Gly Gly  Thr Cys Cys Thr Ala  Cys Ala Thr
    1790                1795                1800

Gly Thr  Ala Thr Thr Ala Gly  Gly Thr Thr Cys Thr  Thr Thr Cys
    1805                1810                1815

Ala Ala  Gly Thr Thr Thr Gly  Ala Cys Thr Gly Gly  Gly Ala Gly
    1820                1825                1830

Gly Thr  Cys Ala Cys Cys Thr  Thr Thr Thr Thr Cys  Thr Gly Ala
    1835                1840                1845

Thr Thr  Thr Ala Cys Ala Ala  Gly Thr Cys Cys Thr  Ala Ala Thr
    1850                1855                1860

Thr Gly  Thr Thr Gly Gly Ala  Gly Cys Thr Cys Ala  Gly Thr Ala
    1865                1870                1875

Ala Ala  Gly Gly Thr Ala Gly  Gly Ala Gly Gly Ala  Ala Gly Gly
    1880                1885                1890

Thr Gly  Gly Cys Thr Gly Gly  Thr Thr Gly Gly Thr  Cys Cys Thr
    1895                1900                1905

Cys Cys  Cys Thr Thr Cys Cys  Cys Cys Cys Thr Gly  Thr Thr Thr
    1910                1915                1920

Gly Thr  Gly Ala Cys Cys Thr  Gly Ala Ala Thr Thr  Thr Ala Cys
    1925                1930                1935

Ala Gly  Gly Ala Ala Gly Thr  Gly Thr Thr Thr Cys  Ala Ala Cys
    1940                1945                1950

Thr Thr  Gly Thr Cys Thr Thr  Ala Thr Gly Cys Ala  Thr Cys Thr
    1955                1960                1965

Thr Ala  Thr Cys Thr Gly Gly  Cys Ala Thr Gly Thr  Cys Cys Thr
    1970                1975                1980

Gly Gly  Gly Ala Gly Ala Thr  Gly Gly Ala Thr Gly  Gly Gly Cys
    1985                1990                1995

Ala Ala  Gly Ala Ala Cys Thr  Gly Gly Cys Cys Thr  Gly Ala Gly
    2000                2005                2010

Cys Ala  Gly Gly Gly Ala Thr  Thr Thr Thr Thr Gly  Cys Cys Thr
    2015                2020                2025
```

-continued

Thr Gly Ala Thr Thr Thr Thr Ala Ala Gly Thr Cys Ala Cys Thr
    2030                2035                2040

Gly Gly Gly Thr Thr Cys Cys Ala Thr Thr Gly Thr Cys Cys Thr
    2045                2050                2055

Gly Gly Cys Ala Cys Cys Thr Cys Cys Ala Thr Thr Thr Cys Cys
    2060                2065                2070

Thr Thr Ala Gly Thr Thr Thr Cys Thr Gly Thr Ala Ala Gly Cys
    2075                2080                2085

Cys Thr Gly Thr Thr Ala Ala Cys Ala Gly Ala Ala Ala Gly Thr
    2090                2095                2100

Ala Gly Ala Gly Gly Cys Thr Ala Thr Thr Cys Ala Ala Gly Gly
    2105                2110                2115

Thr Thr Ala Thr Cys Ala Ala Gly Ala Ala Ala Gly Thr Gly Cys
    2120                2125                2130

Cys Cys Thr Gly Thr Gly Cys Thr Ala Ala Thr Gly Ala Thr Gly
    2135                2140                2145

Ala Gly Ala Cys Ala Gly Thr Gly Ala Ala Thr Thr Thr Thr Thr
    2150                2155                2160

Thr Thr Thr Thr Thr Thr Thr Thr Thr Cys Gly Ala Gly Ala Thr
    2165                2170                2175

Gly Gly Gly Ala Gly Thr Thr Thr Cys Ala Cys Thr Cys Thr Thr
    2180                2185                2190

Ala Thr Thr Gly Cys Cys Cys Ala Gly Gly Cys Thr Ala Gly Ala
    2195                2200                2205

Gly Thr Gly Cys Ala Ala Thr Gly Gly Thr Gly Cys Gly Ala Thr
    2210                2215                2220

Cys Thr Ala Gly Gly Cys Thr Cys Ala Cys Cys Ala Cys Ala Ala
    2225                2230                2235

Cys Cys Thr Cys Thr Gly Cys Cys Thr Thr Cys Cys Ala Gly Gly
    2240                2245                2250

Thr Thr Cys Ala Ala Gly Thr Gly Ala Thr Thr Ala Gly Ala Gly
    2255                2260                2265

Ala Cys Ala Gly Thr Gly Ala Ala Ala Thr Thr Thr Thr Thr Ala
    2270                2275                2280

Thr Gly Gly Ala Ala Thr Ala Cys Thr Gly Cys Ala Cys Cys Thr
    2285                2290                2295

Ala Thr Ala Ala Ala Ala Cys Ala Cys Ala Thr Gly Cys Cys Ala
    2300                2305                2310

Ala Thr Cys Thr Gly Thr Thr Ala Gly Cys Ala Gly Thr Cys Cys
    2315                2320                2325

Thr Gly Ala Cys Thr Thr Gly Ala Thr Thr Thr Ala Ala Thr Ala
    2330                2335                2340

Ala Ala Ala Ala Cys Cys Ala Ala Gly Gly Ala Gly Ala Gly Cys
    2345                2350                2355

Cys Ala Cys Cys Cys Cys Thr Gly Cys Thr Thr Thr Cys Thr Gly
    2360                2365                2370

Gly Cys Cys Ala Thr Cys Thr Cys Thr Thr Cys Thr Thr Thr Gly
    2375                2380                2385

Thr Cys Thr Ala Cys Cys Ala Thr Thr Thr Cys Ala Ala Ala Thr
    2390                2395                2400

Thr Gly Ala Cys Thr Thr Gly Thr Gly Ala Ala Thr Ala Cys Thr
    2405                2410                2415

-continued

```
Cys Ala Gly Ala Gly Cys Ala Gly Thr Ala Thr Thr Thr
2420          2425              2430

Thr Cys Ala Ala Thr Cys Cys Thr Cys Cys Ala Cys Thr Cys Thr
2435          2440              2445

Ala Ala Gly Thr Gly Ala Thr Thr Cys Cys Thr Cys Cys Ala Gly
2450          2455              2460

Gly Gly Thr Gly Gly Gly Ala Ala Gly Cys Ala Cys Gly Gly Gly
2465          2470              2475

Gly Ala Gly Cys Ala Ala Thr Gly Gly Ala Ala Thr Cys Ala Gly
2480          2485              2490

Ala Thr Gly Gly Cys Thr Cys Ala Thr Thr Cys Thr Cys Thr Cys
2495          2500              2505

Cys Thr Thr Cys Cys Ala Gly Cys Thr Cys Thr Thr Ala Cys
2510          2515              2520

Ala Thr Cys Cys Thr Ala Ala Cys Thr Thr Thr Gly Gly Ala Gly
2525          2530              2535

Gly Thr Ala Thr Ala Gly Ala Ala Gly Gly Ala Ala Gly Gly Ala
2540          2545              2550

Thr Gly Thr Gly Gly Thr Cys Cys Ala Ala Cys Gly Gly Gly Ala
2555          2560              2565

Ala Gly Gly Ala Ala Gly Thr Gly Ala Ala Gly Ala Gly Thr Cys
2570          2575              2580

Thr Ala Thr Thr Gly Gly Thr Thr Thr Thr Ala Cys Thr Thr
2585          2590              2595

Cys Thr Ala Gly Gly Cys Ala Gly Thr Cys Cys Cys Ala Ala Thr
2600          2605              2610

Thr Thr Thr Ala Ala Ala Gly Gly Cys Ala Gly Ala Gly Ala
2615          2620              2625

Ala Gly Thr Ala Thr Cys Thr Gly Cys Ala Thr Cys Thr Thr Thr
2630          2635              2640

Ala Thr Thr Gly Ala Ala Ala Ala Gly Ala Cys Gly Thr Cys
2645          2650              2655

Thr Thr Ala Thr Thr Ala Ala Cys Thr Cys Thr Thr Ala Gly Cys
2660          2665              2670

Thr Cys Cys Thr Cys Ala Gly Thr Thr Ala Gly Ala Ala Ala Ala
2675          2680              2685

Cys Ala Ala Thr Thr Cys Ala Cys Cys Thr Gly Gly Cys Thr Thr
2690          2695              2700

Ala Gly Thr Cys Thr Thr Gly Thr Cys Thr Ala Gly Thr Thr Thr
2705          2710              2715

Cys Ala Ala Ala Gly Thr Thr Ala Cys Cys Ala Thr Gly Gly Ala
2720          2725              2730

Gly Ala Cys Thr Ala Gly Ala Ala Thr Gly Gly Ala Gly Ala Cys
2735          2740              2745

Ala Gly Gly Thr Gly Thr Ala Gly Cys Thr Thr Cys Cys Ala Ala
2750          2755              2760

Gly Gly Ala Gly Gly Cys Cys Thr Thr Gly Gly Cys Ala Thr Cys
2765          2770              2775

Thr Thr Gly Cys Ala Gly Thr Gly Cys Thr Gly Thr Cys Ala
2780          2785              2790

Gly Ala Gly Ala Thr Gly Gly Gly Cys Thr Cys Ala Thr Ala Thr
2795          2800              2805

Cys Thr Gly Cys Thr Thr Gly Gly Gly Gly Ala Ala Gly Cys Cys
```

-continued

```
              2810                2815               2820
Ala Ala Thr Gly Gly Gly Cys Ala Cys Ala Thr Cys Cys
       2825                2830               2835

Thr Thr Cys Cys Cys Ala Ala Thr Thr Thr Cys Ala Thr Gly Ala
       2840                2845               2850

Thr Cys Thr Gly Gly Gly Gly Cys Ala Thr Cys Ala Thr Gly Thr
       2855                2860               2865

Cys Gly Gly Thr Ala Gly Cys Thr Gly Ala Ala Gly Thr Cys Ala
       2870                2875               2880

Gly Cys Cys Ala Cys Gly Gly Thr Gly Gly Ala Gly Thr Gly
       2885                2890               2895

Thr Thr Thr Ala Thr Ala Cys Cys Ala Thr Gly Ala Ala Ala Ala
       2900                2905               2910

Thr Cys Ala Gly Cys Ala Ala Gly Thr Gly Cys Thr Gly Thr Ala
       2915                2920               2925

Ala Ala Thr Cys Ala Gly Gly Cys Cys Thr Thr Thr Thr Gly Cys
       2930                2935               2940

Cys Cys Cys Ala Cys Ala Gly Ala Gly Ala Gly Cys Thr Gly Ala
       2945                2950               2955

Thr Thr Gly Thr Gly Ala Ala Ala Cys Ala Thr Cys Thr Ala Cys
       2960                2965               2970

Thr Ala Gly Cys Ala Cys Ala Cys Cys Ala Cys Thr Gly Cys Cys
       2975                2980               2985

Ala Gly Ala Cys Ala Thr Gly Ala Cys Thr Gly Thr Gly Thr Gly
       2990                2995               3000

Thr Gly Thr Cys Cys Cys Thr Gly Ala Ala Ala Cys Ala Ala Ala
       3005                3010               3015

Ala Thr Thr Gly Cys Thr Cys Thr Gly Gly Cys Thr Cys Ala Gly
       3020                3025               3030

Ala Gly Cys Thr Cys Cys Thr Thr Thr Gly Gly Cys Cys Ala Cys
       3035                3040               3045

Thr Cys Ala Thr Ala Thr Thr Ala Cys Ala Ala Thr Ala Gly Cys
       3050                3055               3060

Ala Ala Cys Ala Gly Ala Cys Ala Thr Thr Thr Gly Cys Thr Thr
       3065                3070               3075

Cys Cys Thr Gly Gly Thr Gly Gly Cys Ala Ala Gly Thr Ala Ala
       3080                3085               3090

Cys Thr Gly Thr Gly Cys Ala Cys Cys Cys Thr Cys Cys Ala Ala
       3095                3100               3105

Cys Ala Thr Cys Cys Ala Ala Cys Cys Cys Ala Gly Ala
       3110                3115               3120

Gly Gly Ala Ala Cys Cys Ala Gly Thr Gly Gly Ala Thr Thr
       3125                3130               3135

Gly Ala Ala Ala Cys Cys Ala Gly Cys Ala Gly Ala Ala Gly
       3140                3145               3150

Cys Cys Ala Ala Gly Ala Cys Ala Gly Gly Ala Thr Gly Cys Ala
       3155                3160               3165

Cys Ala Gly Cys Thr Gly Ala Ala Thr Thr Gly Gly Ala Gly Gly
       3170                3175               3180

Ala Gly Ala Gly Thr Ala Gly Cys Thr Cys Cys Thr Thr Cys
       3185                3190               3195

Thr Cys Ala Cys Ala Cys Ala Ala Ala Cys Gly Cys Thr Thr Thr
       3200                3205               3210
```

```
Cys Ala Ala Ala Gly Thr Thr Gly Gly Cys Ala Ala Ala Ala
    3215                3220                3225
Gly Thr Gly Gly Cys Cys Cys Ala Gly Thr Gly Cys Gly Thr Gly
    3230                3235                3240
Ala Gly Gly Thr Cys Ala Gly Thr Cys Ala Ala Cys Ala Gly Cys
    3245                3250                3255
Cys Ala Ala Ala Thr Thr Cys Cys Ala Gly Cys Ala Gly Cys Ala
    3260                3265                3270
Ala Ala Ala Thr Ala Cys Ala Thr Thr Thr Thr Cys Ala Thr Cys
    3275                3280                3285
Ala Ala Thr Ala Thr Cys Ala Cys Thr Thr Thr Gly Gly Gly Ala
    3290                3295                3300
Gly Ala Ala Thr Ala Ala Cys Thr Gly Thr Gly Gly Cys Ala Cys
    3305                3310                3315
Ala Thr Gly Cys Thr Cys Thr Thr Thr Cys Thr Gly Cys Thr Thr
    3320                3325                3330
Thr Cys Thr Cys Thr Gly Thr Ala Cys Thr Gly Thr Ala Thr Ala
    3335                3340                3345
Gly Gly Cys Ala Ala Cys Ala Thr Gly Thr Thr Gly Thr Ala Cys
    3350                3355                3360
Thr Cys Cys Cys Ala Gly Thr Ala Gly Cys Ala Ala Cys Thr Ala
    3365                3370                3375
Gly Ala Thr Cys Thr Cys Thr Thr Thr Thr Ala Cys Cys Thr Cys
    3380                3385                3390
Thr Thr Cys Thr Thr Thr Ala Gly Cys Cys Ala Ala Gly Ala Ala
    3395                3400                3405
Gly Cys Ala Ala Gly Ala Thr Cys Thr Gly Thr Cys Ala Cys Cys
    3410                3415                3420
Cys Ala Cys Ala Ala Cys Ala Cys Cys Ala Cys Ala Thr Ala Thr
    3425                3430                3435
Cys Thr Thr Gly Ala Ala Ala Ala Gly Ala Thr Gly Cys Thr Thr
    3440                3445                3450
Thr Thr Cys Ala Thr Ala Ala Thr Thr Thr Thr Cys Ala Cys Thr
    3455                3460                3465
Ala Thr Ala Cys Cys Thr Cys Thr Ala Ala Ala Cys Cys Ala
    3470                3475                3480
Ala Thr Thr Gly Thr Ala Cys Cys Gly Ala Cys Ala Thr Cys Ala
    3485                3490                3495
Cys Gly Thr Ala Gly Ala Cys Ala Ala Ala Ala Cys Thr Cys
    3500                3505                3510
Cys Ala Gly Ala Thr Ala Ala Thr Cys Cys Ala Thr Thr Gly
    3515                3520                3525
Ala Thr Thr Gly Gly Gly Thr Ala Thr Thr Thr Thr Cys Ala Thr
    3530                3535                3540
Thr Ala Thr Thr Ala Thr Thr Gly Gly Ala Cys Ala Cys Ala
    3545                3550                3555
Thr Gly Ala Ala Thr Thr Ala Ala Ala Thr Cys Cys Cys Ala Ala
    3560                3565                3570
Gly Gly Gly Ala Ala Ala Gly Thr Gly Ala Gly Ala Ala Gly Ala
    3575                3580                3585
Ala Ala Ala Thr Thr Ala Ala Thr Gly Thr Ala Thr Thr Ala Gly
    3590                3595                3600
```

-continued

```
Cys Ala Ala Cys Cys Ala Gly Thr Gly Thr Ala Gly Cys Cys
3605                3610                3615

Ala Ala Cys Thr Cys Thr Gly Cys Thr Gly Thr Ala Ala Thr Thr
3620                3625                3630

Ala Cys Cys Thr Thr Thr Ala Gly Ala Thr Ala Ala Ala Thr Gly
3635                3640                3645

Thr Thr Thr Ala Thr Thr Thr Thr Cys Ala Thr Thr Cys Thr
3650                3655                3660

Ala Thr Ala Cys Ala Gly Thr Cys Thr Ala Thr Cys Ala Ala Ala
3665                3670                3675

Thr Thr Thr Gly Cys Cys Cys Cys Thr Gly Gly Cys Thr Thr
3680                3685                3690

Thr Ala Thr Thr Ala Cys Thr Cys Cys Cys Ala Ala Thr Thr Gly
3695                3700                3705

Ala Ala Thr Thr Ala Thr Cys Thr Ala Cys Cys Thr Cys Ala Thr
3710                3715                3720

Thr Thr Thr Gly Thr Thr Ala Ala Thr Thr Thr Ala Ala Thr Thr
3725                3730                3735

Thr Ala Thr Cys Ala Ala Ala Gly Gly Thr Ala Ala Cys Ala Thr
3740                3745                3750

Thr Gly Thr Thr Thr Thr Cys Thr Cys Ala Gly Gly Thr Ala Thr
3755                3760                3765

Ala Ala Cys Ala Cys Ala Thr Ala Gly Ala Ala Ala Cys Ala Cys
3770                3775                3780

Cys Ala Ala Gly Ala Thr Thr Thr Thr Cys Ala Gly Cys Ala Thr
3785                3790                3795

Cys Thr Gly Ala Ala Thr Cys Ala Ala Ala Cys Thr Ala Ala Ala
3800                3805                3810

Ala Thr Thr Ala Cys Thr Thr Gly Cys Thr Thr Gly Ala Cys Thr
3815                3820                3825

Thr Cys Ala Cys Thr Cys Cys Ala Gly Gly Gly Thr Gly Ala Gly
3830                3835                3840

Ala Cys Thr Thr Gly Ala Cys Cys Thr Thr Thr Ala Ala Gly Gly
3845                3850                3855

Cys Cys Cys Ala Ala Ala Cys Thr Cys Thr Gly Gly Thr Gly Ala
3860                3865                3870

Ala Cys Thr Gly Thr Thr Gly Gly Ala Cys Thr Gly Gly Gly Thr
3875                3880                3885

Ala Gly Ala Ala Ala Thr Cys Thr Thr Thr Cys Ala Ala Gly Ala
3890                3895                3900

Ala Gly Cys Thr Thr Gly Ala Ala Ala Ala Thr Ala Ala Gly Gly
3905                3910                3915

Cys Cys Ala Thr Ala Ala Ala Gly Gly Ala Gly Gly Gly Gly Cys
3920                3925                3930

Thr Thr Thr Cys Ala Ala Ala Thr Thr Cys Cys Thr Ala Ala Ala
3935                3940                3945

Thr Cys Cys Ala Cys Ala Thr Ala Thr Ala Gly Gly Gly Cys Thr
3950                3955                3960

Gly Ala Gly Thr Thr Cys Cys Thr Ala Gly Thr Cys Cys Thr Ala
3965                3970                3975

Cys Ala Cys Ala Ala Thr Cys Ala Gly Ala Ala Thr Thr Thr Gly
3980                3985                3990

Cys Cys Thr Thr Thr Thr Thr Ala Ala Gly Thr Cys Ala Cys Gly
```

-continued

```
                    3995                4000                4005
Cys Thr Gly Cys Ala Ala Cys Thr Ala Thr Thr Cys Cys Gly Gly
               4010                4015                4020
Cys Thr Thr Thr Thr Thr Ala Thr Ala Thr Gly Gly Cys Ala Cys
               4025                4030                4035
Cys Thr Thr Thr Cys Thr Gly Ala Gly Gly Ala Gly Gly Gly
               4040                4045                4050
Gly Ala Thr Thr Thr Thr Ala Cys Ala Gly Cys Cys Gly Ala Gly
               4055                4060                4065
Gly Gly Ala Cys Cys Thr Cys Cys Ala Ala Ala Gly Gly Gly Ala
               4070                4075                4080
Ala Cys Gly Thr Cys Cys Ala Thr Thr Thr Gly Cys Ala Thr Gly
               4085                4090                4095
Thr Gly Thr Gly Cys Cys Cys Thr Gly Gly Thr Ala Thr Thr Thr
               4100                4105                4110
Ala Gly Gly Gly Thr Thr Thr Gly Thr Cys Thr Cys Ala Thr Gly
               4115                4120                4125
Gly Thr Cys Ala Gly Cys Thr Cys Gly Cys Cys Thr Cys Thr Cys
               4130                4135                4140
Ala Ala Ala Gly Ala Thr Gly Gly Cys Thr Cys Ala Cys Cys Ala
               4145                4150                4155
Ala Thr Cys Ala Cys Cys Thr Gly Cys Cys Thr Gly Thr Thr Thr
               4160                4165                4170
Thr Thr Ala Cys Thr Thr Ala Gly Ala Ala Ala Gly Cys Ala Gly
               4175                4180                4185
Gly Cys Thr Thr Gly Gly Gly Cys Ala Gly Gly Ala Gly Gly Gly
               4190                4195                4200
Gly Ala Ala Ala Thr Gly Gly Ala Thr Thr Gly Ala Ala Cys
               4205                4210                4215
Cys Ala Thr Cys Thr Cys Ala Gly Ala Cys Cys Ala Ala Cys Thr
               4220                4225                4230
Cys Thr Ala Thr Cys Thr Cys Thr Thr Cys Thr Ala Gly Cys Ala
               4235                4240                4245
Cys Thr Cys Ala Gly Cys Thr Cys Ala Gly Cys Cys Thr Cys Cys
               4250                4255                4260
Thr Gly Thr Cys Cys Cys Ala Thr Gly Ala Gly Cys Ala Ala
               4265                4270                4275
Thr Ala Ala Ala Cys Thr Cys Thr Cys Thr Cys Cys Thr Thr
               4280                4285                4290
Ala Thr Gly Thr Cys Thr Gly Thr Gly Ala Ala Ala Thr Thr Cys
               4295                4300                4305
Gly Thr Thr Thr Cys Thr Thr Thr Thr Cys Ala Thr Gly
               4310                4315                4320
Gly Thr Gly Cys Cys Thr Thr Cys Thr Thr Thr Cys Thr Ala
               4325                4330                4335
Ala Gly Ala Ala Ala Ala Gly Ala Thr Ala Gly Ala Ala Gly
               4340                4345                4350
Ala Ala Thr Gly Gly Gly Gly Cys Cys Ala Gly Gly Thr Thr Cys
               4355                4360                4365
Ala Thr Gly Thr Cys Cys Cys Ala Gly Thr Thr Gly Thr Cys Ala
               4370                4375                4380
Cys Cys Cys Thr Thr Thr Thr Ala Cys Ala Thr Gly Cys Thr Thr
               4385                4390                4395
```

-continued

```
Gly Gly Gly Thr Gly Cys Ala Gly Gly Thr Ala Gly Ala Thr Gly
4400                4405                4410
Ala Gly Gly Cys Cys Thr Thr Cys Cys Ala Thr Gly Gly Cys
4415                4420                4425
Thr Ala Cys Ala Gly Thr Gly Thr Gly Ala Cys Cys Cys Thr Thr
4430                4435                4440
Gly Gly Ala Gly Gly Ala Ala Cys Cys Ala Ala Gly Gly Cys
4445                4450                4455
Thr Gly Thr Gly Cys Ala Thr Thr Gly Thr Thr Ala Gly Ala Ala
4460                4465                4470
Thr Thr Thr Ala Gly Cys Cys Cys Ala Gly Ala Thr Gly Cys Ala
4475                4480                4485
Gly Gly Ala Thr Ala Ala Ala Cys Thr Ala Gly Cys Thr Thr Gly
4490                4495                4500
Cys Cys Thr Gly Ala Gly Thr Thr Thr Ala Ala Thr Gly Ala Gly
4505                4510                4515
Gly Ala Thr Ala Thr Thr Ala Thr Ala Thr Cys Ala Gly Gly Thr
4520                4525                4530
Gly Cys Cys Ala Gly Gly Ala Ala Thr Cys Cys Thr Thr Gly
4535                4540                4545
Gly Gly Thr Cys Ala Gly Cys Thr Cys Cys Thr Ala Thr Cys Cys
4550                4555                4560
Thr Cys Thr Gly Gly Ala Cys Gly Gly Gly Gly Ala Gly Cys Ala
4565                4570                4575
Thr Cys Ala Thr Gly Gly Gly Ala Ala Ala Ala Gly Ala Gly
4580                4585                4590
Gly Thr Cys Cys Gly Ala Gly Thr Cys Ala Thr Ala Thr Thr Thr
4595                4600                4605
Ala Gly Gly Gly Cys Thr Thr Cys Ala Thr Gly Thr Gly Thr Cys
4610                4615                4620
Thr Gly Gly Ala Ala Gly Gly Ala Gly Cys Cys Ala Thr Thr
4625                4630                4635
Ala Gly Cys Thr Cys Thr Thr Ala Ala Ala Thr Thr Ala Thr Thr
4640                4645                4650
Cys Ala Cys Ala Gly Ala Ala Gly Thr Cys Ala Cys Cys Ala Cys
4655                4660                4665
Gly Gly Ala Ala Gly Gly Thr Thr Gly Thr Thr Ala Ala Gly
4670                4675                4680
Ala Thr Gly Cys Ala Gly Ala Thr Thr Cys Cys Ala Gly Cys Ala
4685                4690                4695
Thr Cys Cys Cys Thr Cys Cys Thr Cys Ala Gly Ala Gly Ala
4700                4705                4710
Thr Cys Ala Ala Thr Thr Cys Ala Gly Cys Ala Gly Gly Gly
4715                4720                4725
Cys Cys Ala Gly Gly Cys Ala Gly Gly Ala Cys Cys Thr Gly Gly
4730                4735                4740
Gly Thr Thr Thr Cys Cys Gly Cys Ala Cys Thr Thr Thr Ala
4745                4750                4755
Ala Thr Cys Ala Thr Cys Gly Ala Thr Gly Cys Cys Cys Ala Gly
4760                4765                4770
Gly Thr Ala Ala Cys Thr Gly Ala Thr Ala Gly Gly Ala Gly Thr
4775                4780                4785
```

-continued

```
Thr Thr Thr Cys Thr Thr Cys Ala Ala Ala Cys Cys Ala Thr Cys
    4790            4795                4800

Cys Cys Cys Thr Ala Ala Gly Gly Ala Gly Ala Ala Ala Thr Gly
    4805            4810                4815

Ala Thr Cys Thr Thr Ala Gly Ala Cys Ala Cys Thr Thr Gly Gly
    4820            4825                4830

Ala Thr Ala Ala Ala Cys Thr Cys Thr Ala Thr Ala Gly Ala Ala
    4835            4840                4845

Ala Ala Thr Thr Gly Ala Gly Thr Gly Thr Thr Cys Thr Ala
    4850            4855                4860

Thr Thr Ala Ala Thr Ala Ala Cys Thr Ala Thr Cys Thr Ala Gly
    4865            4870                4875

Gly Thr Thr Thr Cys Ala Ala Thr Thr Gly Thr Cys Thr Thr Gly
    4880            4885                4890

Thr Ala Thr Cys Thr Thr Thr Cys Cys Cys Thr Ala Ala Thr Thr
    4895            4900                4905

Cys Thr Cys Cys Ala Ala Ala Cys Ala Gly Thr Thr Cys Ala Ala
    4910            4915                4920

Thr Cys Thr Cys Cys Ala Gly Cys Thr Thr Thr Ala Thr Thr Cys
    4925            4930                4935

Ala Ala Thr Gly Gly Cys Thr Gly Gly Gly Cys Cys Ala Thr Thr
    4940            4945                4950

Thr Thr Gly Thr Thr Cys Thr Gly Gly Ala Gly Gly Gly Ala
    4955            4960                4965

Cys Ala Ala Ala Ala Thr Thr Gly Ala Cys Cys Thr Cys Thr Cys
    4970            4975                4980

Cys Ala Thr Gly Ala Ala Ala Thr Thr Gly Cys Ala Ala Ala Ala
    4985            4990                4995

Ala Cys Cys Cys Ala Thr Cys Thr Thr Cys Ala Thr Thr Cys Cys
    5000            5005                5010

Thr Thr Thr Thr Thr Ala Thr Gly Gly Gly Gly Cys Thr Cys Cys
    5015            5020                5025

Ala Gly Gly Thr Cys Ala Thr Ala Ala Gly Gly Ala Thr Gly Ala
    5030            5035                5040

Gly Ala Thr Ala Thr Ala Thr Thr Gly Gly Gly Gly Thr Ala
    5045            5050                5055

Cys Thr Gly Gly Cys Ala Gly Ala Gly Gly Ala Thr Gly Gly Cys
    5060            5065                5070

Ala Gly Ala Gly Cys Thr Gly Gly Cys Thr Gly Cys Thr Cys
    5075            5080                5085

Thr Gly Ala Gly Cys Cys Ala Gly Gly Ala Ala Gly Cys Cys Thr
    5090            5095                5100

Thr Gly Thr Thr Ala Gly Ala Gly Gly Ala Ala Gly Gly Ala Ala
    5105            5110                5115

Cys Thr Cys Thr Gly Gly Cys Ala Thr Cys Ala Gly Ala Gly
    5120            5125                5130

Gly Thr Gly Thr Cys Cys Cys Thr Thr Gly Gly Gly Gly
    5135            5140                5145

Cys Ala Cys Thr Thr Gly Cys Thr Thr Gly Gly Gly Thr Cys Thr
    5150            5155                5160

Thr Gly Gly Ala Thr Cys Ala Ala Ala Cys Thr Cys Thr Ala Cys
    5165            5170                5175

Thr Gly Gly Gly Gly Cys Ala Gly Cys Cys Thr Gly Gly Cys Thr
```

```
                5180                5185                5190
Gly Thr Gly Gly Gly Ala Gly Gly Thr Gly Ala Thr Gly Ala Cys
        5195                5200                5205
Ala Thr Cys Thr Gly Cys Cys Ala Cys Cys Thr Cys Thr Gly Cys
        5210                5215                5220
Cys Ala Cys Thr Ala Cys Cys Ala Gly Ala Gly Cys Thr Thr
        5225                5230                5235
Gly Thr Cys Cys Thr Gly Cys Cys Cys Thr Cys Thr Thr Cys Cys
        5240                5245                5250
Cys Ala Gly Cys Cys Ala Gly Cys Cys Thr Cys Ala Cys Ala Cys
        5255                5260                5265
Ala Cys Ala Gly Gly Ala Gly Cys Thr Gly Ala Gly Cys Cys Ala
        5270                5275                5280
Gly Gly Cys Thr Gly Ala Gly Gly Cys Ala Ala Gly Gly Thr Cys
        5285                5290                5295
Ala Gly Cys Gly Ala Gly Ala Gly Ala Cys Ala Gly Thr Thr Cys
        5300                5305                5310
Thr Cys Cys Ala Thr Gly Cys Cys Ala Gly Thr Ala Thr Cys Thr
        5315                5320                5325
Gly Gly Gly Thr Gly Thr Gly Gly Gly Thr Cys Thr Cys Thr Thr
        5330                5335                5340
Gly Thr Thr Gly Gly Cys Thr Cys Cys Cys Ala Gly Cys Thr Cys
        5345                5350                5355
Ala Thr Cys Cys Cys Gly Thr Gly Thr Gly Gly Cys Thr Gly Ala
        5360                5365                5370
Cys Cys Cys Thr Thr Cys Cys Ala Gly Gly Thr Cys Ala Cys Thr
        5375                5380                5385
Thr Gly Gly Ala Gly Cys Ala Gly Cys Cys Ala Gly Thr Ala Ala
        5390                5395                5400
Thr Gly Ala Cys Ala Gly Thr Gly Thr Cys Cys Thr Ala Ala Cys
        5405                5410                5415
Ala Gly Cys Thr Gly Gly Thr Gly Gly Gly Thr Ala Thr Gly Gly
        5420                5425                5430
Ala Gly Gly Ala Ala Ala Gly Ala Cys Thr Ala Gly Ala Cys Ala
        5435                5440                5445
Thr Cys Ala Gly Gly Cys Thr Ala Thr Gly Gly Ala Cys Thr Cys
        5450                5455                5460
Ala Cys Ala Thr Gly Gly Ala Gly Gly Gly Cys Cys Cys Thr Gly
        5465                5470                5475
Gly Thr Gly Thr Thr Gly Gly Cys Thr Cys Thr Gly Gly Gly Ala
        5480                5485                5490
Cys Cys Thr Gly Gly Gly Cys Thr Gly Gly Gly Cys Cys Gly Gly
        5495                5500                5505
Ala Cys Cys Thr Gly Gly Gly Ala Gly Ala Gly Gly Gly Thr
        5510                5515                5520
Gly Gly Gly Thr Gly Gly Ala Gly Cys Thr Thr Gly Gly Cys Cys
        5525                5530                5535
Thr Cys Thr Gly Cys Ala Gly Thr Thr Gly Cys Gly Cys Thr
        5540                5545                5550
Thr Gly Cys Ala Gly Gly Thr Thr Cys Ala Gly Gly Gly Ala
        5555                5560                5565
Gly Ala Ala Ala Gly Thr Thr Gly Thr Thr Thr Gly Ala Gly Ala
        5570                5575                5580
```

-continued

```
Thr Cys Ala Gly Gly Gly Thr Thr Thr Ala Gly Gly Gly Thr
    5585                5590                5595

Ala Gly Thr Gly Thr Thr Thr Cys Cys Cys Ala Thr Thr Ala Ala
    5600                5605                5610

Thr Cys Thr Thr Cys Ala Thr Cys Ala Thr Ala Thr Cys Thr
    5615                5620                5625

Thr Thr Thr Gly Ala Thr Gly Thr Ala Gly Gly Thr Gly Cys Thr
    5630                5635                5640

Gly Thr Thr Ala Thr Thr Ala Thr Cys Thr Cys Thr Ala Cys Gly
    5645                5650                5655

Thr Thr Ala Cys Ala Cys Ala Thr Cys Thr Gly Gly Ala Gly
    5660                5665                5670

Gly Ala Thr Thr Thr Gly Ala Ala Ala Gly Thr Cys Cys Thr Gly
    5675                5680                5685

Gly Ala Gly Ala Cys Ala Gly Gly Gly Ala Gly Gly Thr Thr Thr
    5690                5695                5700

Thr Gly Gly Gly Gly Ala Gly Ala Ala Thr Gly Cys Ala Ala Ala
    5705                5710                5715

Ala Cys Ala Gly Gly Gly Cys Ala Gly Gly Gly Cys Thr Cys Thr
    5720                5725                5730

Cys Ala Ala Gly Gly Ala Gly Gly Gly Thr Gly Gly Ala Cys Cys
    5735                5740                5745

Ala Gly Thr Gly Ala Cys Cys Ala Thr Gly Gly Gly Ala Ala
    5750                5755                5760

Ala Cys Thr Gly Gly Thr Gly Thr Thr Thr Cys Thr Ala Thr Thr
    5765                5770                5775

Ala Ala Thr Ala Ala Gly Thr Ala Thr Cys Thr Ala Ala Gly Thr
    5780                5785                5790

Thr Thr Cys Ala Ala Thr Thr Gly Thr Cys Thr Thr Gly Thr Ala
    5795                5800                5805

Thr Cys Thr Thr Thr Cys Cys Cys Thr Ala Ala Thr Thr Cys Thr
    5810                5815                5820

Cys Cys Ala Ala Ala Cys Gly Gly Thr Cys Ala Ala Thr Cys
    5825                5830                5835

Thr Cys Cys Ala Gly Thr Thr Thr Thr Ala Thr Thr Cys Ala Gly
    5840                5845                5850

Gly Gly Ala Cys Thr Gly Gly Gly Cys Cys Ala Thr Thr Thr Thr
    5855                5860                5865

Gly Thr Thr Cys Thr Cys Ala Gly Ala Gly Gly Gly Ala Cys Ala
    5870                5875                5880

Ala Ala Ala Cys Thr Gly Ala Thr Cys Thr Cys Thr Cys Cys Ala
    5885                5890                5895

Thr Gly Ala Ala Ala Thr Cys Cys Cys Thr Gly Cys Ala Cys
    5900                5905                5910

Cys Thr Cys Ala Cys Thr Cys Thr Gly Gly Gly Cys Ala Gly Cys
    5915                5920                5925

Thr Cys Thr Ala Gly Gly Cys Thr Cys Ala Gly Cys Ala Gly Ala
    5930                5935                5940

Thr Gly Thr Thr Thr Thr Thr Cys Thr Gly Cys Cys Ala Thr Thr
    5945                5950                5955

Ala Gly Gly Ala Ala Ala Cys Ala Gly Cys Cys Cys Cys Thr Thr
    5960                5965                5970
```

-continued

```
Ala Cys Thr Cys Thr Cys Ala Gly Cys Thr Cys Thr Gly Thr
    5975            5980            5985
Gly Cys Thr Ala Ala Cys Ala Cys Cys Cys Ala Thr Ala Cys Cys
    5990            5995            6000
Cys Ala Cys Cys Ala Gly Cys Thr Gly Gly Gly Cys Gly Thr Thr
    6005            6010            6015
Gly Gly Gly Ala Cys Cys Thr Cys Thr Cys Cys Cys Gly Thr Cys
    6020            6025            6030
Ala Thr Ala Thr Gly Gly Cys Thr Gly Cys Cys Ala Cys Thr Thr
    6035            6040            6045
Gly Cys Thr Thr Gly Gly Gly Ala Ala Gly Gly Ala Ala Thr Thr
    6050            6055            6060
Cys Thr Cys Cys Ala Gly Ala Cys Thr Cys Cys Thr Thr Thr Thr
    6065            6070            6075
Ala Cys Thr Thr Thr Gly Thr Ala Thr Gly Thr Gly Thr Thr Thr
    6080            6085            6090
Cys Thr Ala Gly Gly Gly Gly Ala Ala Thr Thr Cys Thr Gly Ala
    6095            6100            6105
Gly Gly Gly Ala Ala Gly Ala Ala Gly Cys Thr Thr Thr Gly Cys
    6110            6115            6120
Ala Gly Cys Ala Ala Cys Cys Thr Cys Thr Gly Thr Gly Cys Cys
    6125            6130            6135
Cys Ala Gly Ala Ala Cys Ala Thr Ala Cys Gly Gly Cys Thr Cys
    6140            6145            6150
Ala Cys Ala Ala Gly Thr Cys Cys Thr Thr Thr Gly Thr Gly Cys
    6155            6160            6165
Cys Gly Ala Cys Ala Gly Gly Gly Ala Ala Thr Cys Thr Ala Thr
    6170            6175            6180
Cys Thr Ala Ala Thr Thr Gly Thr Thr Thr Thr Ala Gly Thr Gly
    6185            6190            6195
Thr Gly Thr Gly Ala Gly Gly Cys Thr Cys Ala Thr Thr Gly Thr
    6200            6205            6210
Cys Ala Gly Cys Cys Thr Ala Gly Ala Thr Thr Thr Cys Cys Cys
    6215            6220            6225
Thr Gly Ala Ala Ala Cys Thr Cys Thr Gly Gly Gly Cys Cys Ala
    6230            6235            6240
Gly Cys Ala Gly Cys Cys Cys Cys Ala Gly Gly Ala Gly Cys
    6245            6250            6255
Ala Thr Cys Ala Gly Thr Ala Gly Gly Ala Cys Cys Cys Ala Gly
    6260            6265            6270
Cys Ala Thr Thr Thr Cys Cys Cys Cys Thr Gly Gly Cys Ala Cys
    6275            6280            6285
Cys Ala Ala Ala Gly Thr Gly Gly Ala Cys Cys Thr Cys Thr Thr
    6290            6295            6300
Thr Gly Cys Ala Cys Cys Thr Thr Gly Cys Ala Gly Cys Cys Gly
    6305            6310            6315
Gly Gly Ala Gly Ala Ala Cys Thr Gly Ala Cys Thr Thr Ala Gly
    6320            6325            6330
Ala Gly Gly Gly Cys Cys Cys Thr Gly Gly Thr Gly Thr Thr Gly
    6335            6340            6345
Gly Cys Thr Cys Thr Gly Gly Ala Ala Cys Cys Thr Gly Gly Gly
    6350            6355            6360
Cys Thr Gly Ala Gly Ala Thr Gly Gly Ala Thr Thr Cys Gly Gly
```

```
                   6365                 6370                 6375
Gly Gly  Ala Gly Ala Gly  Cys Thr Gly Gly   Thr Gly Gly
    6380                 6385                 6390
Ala Gly  Cys Thr Thr Gly  Gly Cys Cys Thr   Cys Thr Ala Cys Gly
    6395                 6400                 6405
Gly Thr  Cys Thr Gly Thr  Thr Cys Thr Thr Gly   Cys Ala Gly Ala
    6410                 6415                 6420
Thr Thr  Cys Ala Gly Gly  Ala Gly Ala Gly Ala   Ala Gly Thr
    6425                 6430                 6435
Gly Gly  Thr Ala Thr Gly  Ala Gly Ala Gly Cys Ala   Gly Thr Gly
    6440                 6445                 6450
Thr Gly  Gly Thr Thr Thr Gly   Thr Ala Ala Gly Thr   Thr Cys Cys
    6455                 6460                 6465
Cys Cys  Ala Ala Cys Thr Thr   Cys Cys Cys Cys Gly   Cys Thr Gly
    6470                 6475                 6480
Gly Cys  Thr Cys Ala Cys Ala   Cys Thr Gly Thr Cys   Thr Cys Cys
    6485                 6490                 6495
Cys Cys  Ala Gly Ala Cys Cys   Ala Ala Thr Gly Gly   Cys Cys Thr
    6500                 6505                 6510
Ala Thr  Thr Ala Gly Cys Cys   Cys Cys Cys Ala Ala   Ala Ala Ala
    6515                 6520                 6525
Gly Thr  Thr Ala Gly Thr Cys   Cys Ala Ala Cys Cys   Cys Cys Ala
    6530                 6535                 6540
Gly Gly  Cys Cys Ala Gly Cys   Thr Gly Cys Cys Thr   Thr Thr Gly
    6545                 6550                 6555
Cys Thr  Cys Thr Gly Cys Thr   Gly Thr Gly Gly Cys   Cys Thr Ala
    6560                 6565                 6570
Ala Gly  Thr Thr Cys Thr Gly   Gly Cys Cys Thr Gly   Gly Thr Cys
    6575                 6580                 6585
Ala Ala  Ala Gly Gly Ala Ala   Gly Gly Thr Gly Gly   Cys Ala Gly
    6590                 6595                 6600
Gly Ala  Ala Cys Thr Cys Cys   Ala Gly Gly Cys Thr   Thr Gly Cys
    6605                 6610                 6615
Thr Cys  Cys Thr Gly Cys Cys   Thr Cys Cys Thr Cys   Ala Cys Ala
    6620                 6625                 6630
Cys Cys  Thr Cys Ala Thr Thr   Cys Cys Ala Cys Ala   Ala Ala Thr
    6635                 6640                 6645
Gly Cys  Gly Gly Ala Gly Thr   Gly Ala Ala Ala Gly   Ala Gly Cys
    6650                 6655                 6660
Ala Gly  Gly Ala Gly Cys Cys   Ala Gly Ala Cys Ala   Cys Ala Thr
    6665                 6670                 6675
Thr Thr  Gly Gly Gly Gly Gly   Thr Thr Gly Ala Cys   Thr Gly Thr
    6680                 6685                 6690
Cys Thr  Ala Gly Ala Ala Ala   Gly Gly Ala Gly Gly   Ala Ala Thr
    6695                 6700                 6705
Cys Ala  Gly Ala Gly Gly Thr   Cys Cys Cys Ala Ala   Gly Gly Ala
    6710                 6715                 6720
Ala Cys  Ala Cys Ala Ala Thr   Cys Gly Thr Gly Cys   Ala Ala Cys
    6725                 6730                 6735
Thr Thr  Cys Cys Thr Ala Gly   Gly Gly Ala Ala Thr   Cys Thr Gly
    6740                 6745                 6750
Cys Ala  Thr Cys Ala Gly Gly   Ala Gly Ala Ala Ala   Gly Ala Ala
    6755                 6760                 6765
```

-continued

```
Gly Cys Gly Gly Cys Thr Ala Gly Gly Ala Cys Ala Cys Ala Cys
    6770                6775                6780
Ala Gly Thr Gly Gly Cys Thr Thr Cys Gly Cys Thr Cys Ala Gly
    6785                6790                6795
Cys Cys Thr Gly Gly Cys Cys Ala Cys Gly Ala Cys Ala Thr Cys
    6800                6805                6810
Ala Cys Thr Gly Thr Gly Cys Ala Gly Ala Ala Gly Ala Ala Gly
    6815                6820                6825
Ala Gly Ala Thr Cys Thr Gly Thr Cys Ala Gly Gly Gly Gly Thr
    6830                6835                6840
Cys Cys Ala Gly Ala Gly Gly Ala Gly Cys Gly Gly Ala Gly Thr
    6845                6850                6855
Cys Cys Thr Gly Gly Ala Gly Cys Cys Thr Cys Thr Gly Gly Gly
    6860                6865                6870
Ala Gly Gly Gly Thr Gly Gly Cys Ala Thr Gly Thr Gly Gly Cys
    6875                6880                6885
Ala Gly Cys Thr Gly Cys Ala Gly Gly Cys Thr Gly Thr Gly Gly
    6890                6895                6900
Thr Cys Cys Ala Gly Ala Ala Cys Thr Ala Thr Gly Ala Gly Cys
    6905                6910                6915
Ala Gly Ala Cys Thr Thr Gly Cys Cys Thr Gly Thr Cys Ala Cys
    6920                6925                6930
Thr Cys Thr Cys Cys Ala Ala Ala Cys Ala Thr Thr Ala Cys Ala Cys
    6935                6940                6945
Thr Gly Ala Ala Cys Ala Cys Cys Thr Ala Cys Thr Gly Thr Gly
    6950                6955                6960
Thr Gly Cys Cys Ala Gly Gly Cys Cys Cys Thr Gly Thr Gly Cys
    6965                6970                6975
Thr Thr Thr Gly Thr Cys Ala Gly Gly Cys Thr Cys Thr Gly Gly
    6980                6985                6990
Gly Gly Gly Ala Gly Ala Cys Ala Gly Gly Thr Cys Ala Thr Thr
    6995                7000                7005
Ala Cys Thr Cys Thr Gly Cys Ala Gly Thr Gly Thr Gly Gly Gly
    7010                7015                7020
Ala Ala Gly Cys Gly Gly Gly Gly Cys Thr Gly Cys Cys Cys Thr
    7025                7030                7035
Gly Gly Ala Ala Gly Thr Gly Thr Gly Thr Ala Cys Thr Cys Ala
    7040                7045                7050
Gly Thr Gly Cys Thr Gly Thr Gly Gly Gly Gly Thr Ala Cys
    7055                7060                7065
Ala Gly Ala Gly Gly Gly Ala Gly Gly Gly Cys Thr Gly Gly Ala
    7070                7075                7080
Gly Ala Ala Cys Thr Thr Ala Gly Cys Thr Gly Gly Thr Gly Gly
    7085                7090                7095
Gly Ala Ala Ala Gly Gly Ala Gly Gly Gly Thr Thr Cys Thr Gly
    7100                7105                7110
Gly Ala Ala Gly Gly Cys Thr Thr Cys Thr Cys Ala Gly Ala Gly
    7115                7120                7125
Gly Thr Ala Gly Thr Gly Gly Cys Ala Thr Thr Gly Gly Gly Cys
    7130                7135                7140
Cys Ala Gly Ala Ala Cys Thr Thr Ala Cys Ala Gly Thr Ala Gly
    7145                7150                7155
```

```
Gly Gly Ala Ala Gly Ala Gly Cys Ala Thr Thr Gly Gly Cys
    7160            7165                7170
Ala Ala Gly Gly Cys Ala Cys Ala Gly Ala Gly Ala Gly Ala
    7175            7180                7185
Thr Gly Gly Gly Ala Gly Cys Cys Thr Gly Cys Cys Thr Gly Gly
    7190            7195                7200
Thr Gly Ala Gly Gly Gly Thr Cys Cys Ala Gly Thr Gly Gly
    7205            7210                7215
Thr Gly Ala Cys Ala Gly Ala Gly Cys Thr Cys Ala Gly Thr Gly
    7220            7225                7230
Thr Gly Gly Gly Thr Cys Cys Ala Gly Ala Gly Ala Thr Gly Gly
    7235            7240                7245
Thr Gly Thr Cys Ala Gly Gly Thr Gly Ala Gly Gly Cys Thr
    7250            7255                7260
Gly Ala Gly Ala Gly Gly Gly Gly Ala Gly Gly Gly Cys Ala Ala
    7265            7270                7275
Gly Thr Gly Cys Cys Cys Cys Thr Thr Gly Ala Gly Ala Thr Gly
    7280            7285                7290
Gly Gly Cys Thr Gly Ala Ala Cys Gly Thr Gly Ala Thr Gly Ala
    7295            7300                7305
Thr Gly Ala Thr Cys Thr Gly Thr Gly Gly Cys Cys Ala Gly Thr
    7310            7315                7320
Gly Gly Gly Ala Gly Ala Thr Gly Ala Thr Ala Gly Ala Ala Gly
    7325            7330                7335
Thr Cys Thr Thr Gly Ala Gly Gly Thr Thr Gly Gly Gly Ala Ala
    7340            7345                7350
Thr Ala Thr Ala Ala Gly Ala Ala Thr Thr Ala Gly Gly Thr Cys
    7355            7360                7365
Thr Cys Thr Thr Thr Ala Gly Ala Ala Gly Ala Gly Ala
    7370            7375                7380
Gly Gly Ala Cys Ala Thr Gly Gly Ala Gly Ala Ala Ala Ala Thr
    7385            7390                7395
Cys Cys Ala Thr Ala Thr Thr Thr Thr Thr Ala Gly Cys
    7400            7405                7410
Thr Ala Cys Cys Ala Ala Ala Ala Ala Ala Gly Ala Gly Ala Ala
    7415            7420                7425
Gly Gly Ala Ala Gly Ala Ala Ala Gly Ala Ala Ala Gly Ala
    7430            7435                7440
Ala Ala Thr Ala Ala Gly Ala Ala Gly Ala Gly Ala Ala Gly Cys
    7445            7450                7455
Ala Ala Gly Ala Cys Ala Gly Ala Ala Ala Gly Ala Ala Gly
    7460            7465                7470
Gly Ala Ala Gly Ala Gly Ala Gly Ala Ala Gly Gly Ala Ala Gly
    7475            7480                7485
Ala Ala Thr Gly Gly Cys Ala Ala Ala Gly Gly Ala Ala Gly Gly
    7490            7495                7500
Ala Ala Gly Ala Ala Gly Gly Ala Gly
    7505            7510
```

<210> SEQ ID NO 3
<211> LENGTH: 337
<212> TYPE: PRT
<213> ORGANISM: Homo sapiens

<400> SEQUENCE: 3

```
Met Asn Ser Trp Asp Ala Gly Leu Ala Gly Leu Leu Val Gly Thr Met
1               5                   10                  15

Gly Val Ser Leu Leu Ser Asn Ala Leu Val Leu Leu Cys Leu Leu His
            20                  25                  30

Ser Ala Asp Ile Arg Arg Gln Ala Pro Ala Leu Phe Thr Leu Asn Leu
        35                  40                  45

Thr Cys Gly Asn Leu Leu Cys Thr Val Val Asn Met Pro Leu Thr Leu
    50                  55                  60

Ala Gly Val Val Ala Gln Arg Gln Pro Ala Gly Asp Arg Leu Cys Arg
65                  70                  75                  80

Leu Ala Ala Phe Leu Asp Thr Phe Leu Ala Ala Asn Ser Met Leu Ser
                85                  90                  95

Met Ala Ala Leu Ser Ile Asp Arg Trp Val Ala Val Phe Pro Leu
                100                 105                 110

Ser Tyr Arg Ala Lys Met Arg Leu Arg Asp Ala Ala Leu Met Val Ala
            115                 120                 125

Tyr Thr Trp Leu His Ala Leu Thr Phe Pro Ala Ala Ala Leu Ala Leu
130                 135                 140

Ser Trp Leu Gly Phe His Gln Leu Tyr Ala Ser Cys Thr Leu Cys Ser
145                 150                 155                 160

Arg Arg Pro Asp Glu Arg Leu Arg Phe Ala Val Phe Thr Gly Ala Phe
                165                 170                 175

His Ala Leu Ser Phe Leu Leu Ser Phe Val Val Leu Cys Cys Thr Tyr
                180                 185                 190

Leu Lys Val Leu Lys Val Ala Arg Phe His Cys Lys Arg Ile Asp Val
        195                 200                 205

Ile Thr Met Gln Thr Leu Val Leu Leu Val Asp Leu His Pro Ser Val
210                 215                 220

Arg Glu Arg Cys Leu Glu Glu Gln Lys Arg Arg Gln Arg Ala Thr
225                 230                 235                 240

Lys Lys Ile Ser Thr Phe Ile Gly Thr Phe Leu Val Cys Phe Ala Pro
                245                 250                 255

Tyr Val Ile Thr Arg Leu Val Glu Leu Phe Ser Thr Val Pro Ile Gly
                260                 265                 270

Ser His Trp Gly Val Leu Ser Lys Cys Leu Ala Tyr Ser Lys Ala Ala
            275                 280                 285

Ser Asp Pro Phe Val Tyr Ser Leu Leu Arg His Gln Tyr Arg Lys Ser
            290                 295                 300

Cys Lys Glu Ile Leu Asn Arg Leu Leu His Arg Arg Ser Ile His Ser
305                 310                 315                 320

Ser Gly Leu Thr Gly Asp Ser His Ser Gln Asn Ile Leu Pro Val Ser
                325                 330                 335

Glu

<210> SEQ ID NO 4
<211> LENGTH: 1955
<212> TYPE: PRT
<213> ORGANISM: Homo sapiens

<400> SEQUENCE: 4

Ala Cys Ala Gly Ala Ala Gly Cys Gly Cys Gly Cys Ala Gly Ala Gly
1               5                   10                  15

Thr Cys Cys Cys Ala Thr Cys Cys Thr Gly Cys Cys Ala Cys Gly Cys
            20                  25                  30
```

-continued

```
Cys Ala Cys Gly Ala Gly Gly Ala Gly Ala Gly Ala Ala Gly Ala Ala
        35                  40                  45

Gly Gly Ala Ala Ala Gly Ala Thr Ala Cys Ala Gly Thr Gly Thr Thr
    50                  55                  60

Ala Gly Gly Ala Ala Ala Gly Ala Gly Ala Cys Cys Thr Cys Cys Cys
65                  70                  75                  80

Thr Cys Gly Cys Cys Cys Cys Thr Ala Cys Gly Cys Cys Cys Cys Gly
                85                  90                  95

Cys Gly Cys Cys Cys Cys Thr Gly Cys Gly Cys Cys Thr Cys Gly Cys
            100                 105                 110

Thr Thr Cys Ala Gly Cys Cys Thr Cys Ala Gly Gly Ala Cys Ala Gly
        115                 120                 125

Thr Cys Cys Thr Gly Cys Cys Gly Gly Gly Ala Cys Gly Gly Thr Gly
    130                 135                 140

Ala Gly Cys Gly Cys Ala Thr Thr Cys Ala Gly Cys Ala Cys Cys Cys
145                 150                 155                 160
Thr Gly Gly Ala Cys Ala Gly Cys Ala Cys Cys Gly Cys Gly Gly Thr
                165                 170                 175

Thr Gly Cys Gly Cys Thr Gly Cys Cys Thr Cys Cys Ala Gly Gly Gly
            180                 185                 190

Cys Gly Gly Cys Cys Cys Cys Gly Gly Gly Cys Thr Gly Cys Thr Cys
        195                 200                 205

Cys Thr Gly Cys Thr Cys Cys Gly Cys Ala Gly Ala Gly Cys Thr Ala
    210                 215                 220

Cys Gly Cys Cys Cys Thr Cys Cys Cys Cys Cys Cys Gly Gly Gly Thr
225                 230                 235                 240

Gly Cys Cys Cys Cys Gly Gly Ala Cys Cys Cys Thr Gly Cys Ala Cys
                245                 250                 255

Thr Thr Gly Cys Cys Gly Cys Cys Gly Cys Thr Thr Thr Cys Cys Thr
            260                 265                 270

Cys Gly Cys Gly Cys Thr Gly Cys Thr Cys Thr Gly Gly Ala Cys Cys
        275                 280                 285

Thr Thr Gly Cys Thr Ala Gly Cys Cys Gly Gly Cys Thr Cys Thr Gly
    290                 295                 300

Cys Ala Cys Cys Thr Cys Cys Cys Ala Gly Ala Ala Gly Cys Cys Gly
305                 310                 315                 320
Thr Gly Gly Gly Cys Gly Cys Gly Cys Cys Gly Cys Thr Cys Ala Gly
                325                 330                 335

Cys Thr Gly Cys Thr Cys Cys Ala Thr Cys Gly Cys Cys Thr Cys Ala
            340                 345                 350

Cys Thr Thr Thr Cys Cys Cys Ala Gly Gly Cys Thr Cys Gly Cys Gly
        355                 360                 365

Cys Cys Cys Gly Ala Ala Gly Cys Ala Gly Ala Gly Cys Cys Ala Thr
    370                 375                 380

Gly Ala Gly Ala Ala Cys Cys Cys Cys Ala Gly Gly Gly Thr Gly Cys
385                 390                 395                 400

Cys Thr Gly Gly Cys Gly Ala Gly Cys Cys Gly Cys Thr Ala Gly Cys
                405                 410                 415

Gly Cys Cys Ala Thr Gly Gly Gly Cys Cys Cys Cys Gly Gly Cys Gly
            420                 425                 430

Ala Gly Gly Cys Gly Cys Thr Gly Cys Thr Gly Gly Cys Gly Gly Gly
        435                 440                 445
```

-continued

```
Thr Cys Thr Cys Cys Thr Gly Gly Thr Gly Ala Thr Gly Gly Thr Ala
    450                 455                 460
Cys Thr Gly Gly Cys Cys Gly Thr Gly Gly Cys Gly Cys Thr Gly Cys
465                 470                 475                 480
Thr Ala Thr Cys Cys Ala Ala Cys Gly Cys Ala Cys Thr Gly Gly Thr
            485                 490                 495
Gly Cys Thr Gly Cys Thr Thr Thr Gly Thr Thr Gly Cys Gly Cys Cys
            500                 505                 510
Thr Ala Cys Ala Gly Cys Gly Cys Thr Gly Ala Gly Cys Thr Cys Cys
        515                 520                 525
Gly Cys Ala Cys Thr Cys Gly Ala Cys Cys Thr Cys Ala Gly Gly
    530                 535                 540
Cys Gly Thr Cys Cys Thr Cys Cys Thr Gly Gly Thr Gly Ala Ala Thr
545                 550                 555                 560
Cys Thr Gly Thr Cys Thr Cys Thr Gly Gly Gly Cys Cys Ala Cys Cys
            565                 570                 575
Thr Gly Cys Thr Gly Cys Thr Gly Gly Cys Gly Gly Cys Gly Cys Thr
            580                 585                 590
Gly Gly Ala Cys Ala Thr Gly Cys Cys Thr Thr Cys Ala Cys Gly
        595                 600                 605
Cys Thr Gly Cys Thr Cys Gly Gly Thr Gly Thr Gly Ala Thr Gly Cys
    610                 615                 620
Gly Cys Gly Gly Gly Cys Gly Ala Cys Ala Cys Cys Gly Thr Cys
625                 630                 635                 640
Gly Gly Cys Gly Cys Cys Cys Gly Gly Cys Gly Cys Ala Thr Gly Cys
            645                 650                 655
Cys Ala Ala Gly Thr Cys Ala Thr Thr Gly Gly Cys Thr Thr Cys Cys
            660                 665                 670
Thr Gly Gly Ala Cys Ala Cys Cys Thr Thr Cys Cys Thr Gly Gly Cys
        675                 680                 685
Gly Thr Cys Cys Ala Ala Cys Gly Cys Gly Gly Cys Gly Cys Thr Gly
    690                 695                 700
Ala Gly Cys Gly Thr Gly Gly Cys Gly Gly Gly Cys Thr Gly Ala
705                 710                 715                 720
Gly Cys Gly Cys Ala Gly Ala Cys Cys Ala Gly Thr Gly Gly Cys Thr
            725                 730                 735
Gly Gly Cys Ala Gly Thr Gly Gly Cys Thr Thr Cys Cys Cys Ala
            740                 745                 750
Cys Thr Gly Cys Gly Cys Thr Ala Cys Gly Cys Cys Gly Gly Ala Cys
        755                 760                 765
Gly Cys Cys Thr Gly Cys Gly Ala Cys Cys Gly Cys Gly Cys Thr Ala
    770                 775                 780
Thr Gly Cys Cys Gly Gly Cys Cys Thr Gly Cys Thr Gly Cys Thr Gly
785                 790                 795                 800
Gly Gly Cys Thr Gly Thr Gly Cys Cys Thr Gly Gly Gly Ala Cys
            805                 810                 815
Ala Gly Thr Cys Gly Cys Thr Gly Cys Cys Thr Thr Thr Cys
        820                 825                 830
Ala Gly Gly Cys Gly Cys Thr Gly Cys Ala Cys Thr Gly Gly Cys
    835                 840                 845
Thr Gly Cys Thr Cys Gly Thr Gly Gly Cys Thr Thr Gly Gly Cys Thr
    850                 855                 860
Ala Cys Ala Gly Cys Ala Gly Cys Gly Cys Cys Thr Thr Cys Gly Cys
```

-continued

```
865                 870                 875                 880

Gly Thr Cys Cys Thr Gly Thr Thr Cys Gly Cys Thr Gly Cys Gly Cys
                885                 890                 895

Cys Thr Gly Cys Cys Gly Cys Cys Cys Gly Ala Gly Cys Cys Thr Gly
            900                 905                 910

Ala Gly Cys Gly Thr Cys Cys Gly Cys Gly Cys Thr Thr Cys Gly Cys
        915                 920                 925

Ala Gly Cys Cys Thr Thr Cys Ala Cys Cys Gly Cys Cys Ala Cys Gly
    930                 935                 940

Cys Thr Cys Cys Ala Thr Gly Cys Cys Gly Thr Gly Gly Gly Cys Thr
945                 950                 955                 960

Thr Cys Gly Thr Gly Cys Thr Gly Cys Cys Gly Cys Thr Gly Gly Cys
                965                 970                 975
Gly Gly Thr Gly Cys Thr Cys Thr Gly Cys Cys Thr Cys Ala Cys Cys
            980                 985                 990

Thr Cys Gly Cys Thr Cys Cys Ala  Gly Gly Thr Gly Cys  Ala Cys Cys
        995                 1000                1005

Gly Gly  Gly Thr Gly Gly Cys  Ala Cys Gly Cys Ala  Gly Ala Cys
    1010                1015                1020
Ala Cys  Thr Gly Cys Cys Ala  Gly Cys Gly Cys Ala  Thr Gly Gly
    1025                1030                1035

Ala Cys  Ala Cys Cys Gly Thr  Cys Ala Cys Cys Ala  Thr Gly Ala
    1040                1045                1050
Ala Gly  Gly Cys Gly Cys Thr  Cys Gly Cys Gly Cys  Thr Gly Cys
    1055                1060                1065
Thr Cys  Gly Cys Cys Gly Ala  Cys Cys Thr Gly Cys  Ala Cys Cys
    1070                1075                1080

Cys Cys  Ala Gly Thr Gly Thr  Gly Cys Gly Gly Cys  Ala Gly Cys
    1085                1090                1095

Gly Cys  Thr Gly Cys Cys Thr  Cys Ala Thr Cys Cys  Ala Gly Cys
    1100                1105                1110

Ala Gly  Ala Ala Gly Cys Gly  Gly Cys Gly Cys Cys  Gly Cys Cys
    1115                1120                1125

Ala Cys  Cys Gly Cys Gly Cys  Cys Ala Cys Cys Ala  Gly Gly Ala
    1130                1135                1140

Ala Gly  Ala Thr Thr Gly Gly  Cys Ala Thr Thr Gly  Cys Thr Ala
    1145                1150                1155

Thr Thr  Gly Cys Gly Ala Cys  Cys Thr Thr Cys Cys  Thr Cys Ala
    1160                1165                1170

Thr Cys  Thr Gly Cys Thr Thr  Thr Gly Cys Cys Cys  Cys Gly Thr
    1175                1180                1185

Ala Thr  Gly Thr Cys Ala Thr  Gly Ala Cys Cys Ala  Gly Gly Cys
    1190                1195                1200

Thr Gly  Gly Cys Gly Gly Ala  Gly Cys Thr Cys Gly  Thr Gly Cys
    1205                1210                1215

Cys Cys  Thr Thr Cys Gly Thr  Cys Ala Cys Cys Gly  Thr Gly Ala
    1220                1225                1230

Ala Cys  Gly Cys Cys Cys Ala  Gly Thr Gly Gly Gly  Gly Cys Ala
    1235                1240                1245

Thr Cys  Cys Thr Cys Ala Gly  Cys Ala Ala Gly Thr  Gly Cys Cys
    1250                1255                1260

Thr Gly  Ala Cys Cys Thr Ala  Cys Ala Gly Cys Ala  Ala Gly Gly
    1265                1270                1275
```

-continued

```
Cys Gly Gly Thr Gly Gly Cys Cys Gly Ala Cys Cys Cys Gly Thr
    1280                1285                1290
Thr Cys Ala Cys Gly Thr Ala Cys Thr Cys Thr Cys Thr Gly Cys
    1295                1300                1305
Thr Cys Cys Gly Cys Cys Gly Gly Cys Cys Gly Thr Thr Cys Cys
    1310                1315                1320
Gly Cys Cys Ala Ala Gly Thr Cys Cys Thr Gly Gly Cys Cys Gly
    1325                1330                1335
Gly Cys Ala Thr Gly Gly Thr Gly Cys Ala Cys Gly Gly Cys
    1340                1345                1350
Thr Gly Cys Thr Gly Ala Ala Gly Ala Gly Ala Ala Cys Cys Cys
    1355                1360                1365
Cys Gly Cys Gly Cys Cys Cys Ala Gly Cys Ala Thr Cys Cys Ala
    1370                1375                1380
Cys Cys Cys Ala Thr Gly Ala Cys Ala Gly Cys Thr Cys Thr Cys
    1385                1390                1395
Thr Gly Gly Ala Thr Gly Thr Gly Gly Cys Cys Gly Gly Cys Ala
    1400                1405                1410
Thr Gly Gly Thr Gly Cys Ala Cys Cys Ala Gly Cys Thr Gly Cys
    1415                1420                1425
Thr Gly Ala Ala Gly Ala Gly Ala Ala Cys Cys Cys Cys Gly Cys
    1430                1435                1440
Gly Cys Cys Cys Ala Gly Cys Gly Thr Cys Cys Ala Cys Cys Cys
    1445                1450                1455
Ala Cys Ala Ala Cys Gly Gly Cys Thr Cys Thr Gly Thr Gly Gly
    1460                1465                1470
Ala Cys Ala Cys Ala Gly Ala Gly Ala Ala Thr Gly Ala Thr Thr
    1475                1480                1485
Cys Cys Thr Gly Cys Cys Thr Gly Cys Ala Gly Cys Ala Gly Ala
    1490                1495                1500
Cys Ala Cys Ala Cys Thr Gly Ala Gly Gly Cys Cys Thr Gly
    1505                1510                1515
Gly Cys Ala Gly Gly Gly Cys Thr Cys Ala Thr Cys Gly Cys Cys
    1520                1525                1530
Cys Cys Cys Ala Cys Cys Thr Cys Thr Ala Ala Gly Ala Ala
    1535                1540                1545
Gly Cys Cys Cys Thr Gly Thr Gly Gly Ala Ala Ala Gly Gly Gly
    1550                1555                1560
Cys Ala Cys Thr Gly Gly Cys Cys Thr Gly Cys Cys Ala Cys
    1565                1570                1575
Ala Gly Ala Gly Ala Thr Gly Cys Cys Ala Cys Thr Gly Gly Gly
    1580                1585                1590
Gly Ala Cys Cys Cys Cys Ala Gly Ala Cys Ala Cys Cys Ala
    1595                1600                1605
Gly Thr Gly Gly Cys Thr Thr Gly Ala Cys Thr Thr Thr Gly Ala
    1610                1615                1620
Gly Cys Thr Ala Ala Gly Gly Cys Thr Gly Ala Ala Gly Thr Ala
    1625                1630                1635
Cys Ala Gly Gly Ala Gly Gly Ala Gly Gly Ala Gly Gly Ala Gly
    1640                1645                1650
Gly Ala Gly Ala Gly Gly Gly Cys Cys Gly Gly Ala Thr Gly Thr
    1655                1660                1665
```

-continued

Gly Gly Gly Thr Gly Thr Gly Gly Ala Cys Ala Gly Cys Ala Gly
1670            1675                1680

Thr Ala Gly Thr Gly Gly Cys Gly Gly Ala Gly Ala Gly Ala
1685            1690                1695

Gly Cys Thr Cys Gly Gly Gly Cys Thr Gly Gly Cys Thr
1700            1705                1710

Gly Cys Cys Thr Gly Gly Cys Thr Gly Cys Thr Gly Gly Thr
1715            1720                1725

Gly Gly Cys Cys Cys Gly Gly Gly Ala Cys Ala Gly Thr Gly
1730            1735                1740

Gly Cys Thr Thr Thr Thr Cys Cys Thr Cys Thr Cys Thr Gly Ala
1745            1750                1755

Ala Cys Cys Thr Thr Ala Gly Cys Thr Thr Cys Cys Thr Cys Ala
1760            1765                1770

Cys Cys Cys Thr Thr Gly Thr Thr Cys Thr Gly Gly Gly Gly Thr
1775            1780                1785

Cys Ala Thr Gly Gly Cys Gly Ala Thr Gly Cys Thr Thr Cys Gly
1790            1795                1800

Ala Gly Ala Cys Ala Gly Thr Gly Gly Gly Thr Ala Gly Gly Gly
1805            1810                1815

Ala Ala Gly Thr Gly Cys Cys Cys Thr Gly Thr Gly Thr Gly Gly
1820            1825                1830

Cys Ala Thr Ala Thr Gly Gly Thr Ala Cys Thr Cys Gly Thr Gly
1835            1840                1845

Gly Gly Cys Gly Thr Gly Cys Thr Ala Thr Ala Ala Gly Thr Gly
1850            1855                1860

Ala Cys Thr Gly Cys Thr Gly Thr Thr Cys Ala Thr Gly Thr Gly
1865            1870                1875

Gly Gly Thr Gly Ala Gly Gly Thr Gly Gly Thr Cys Ala Cys Thr
1880            1885                1890

Cys Thr Thr Gly Cys Thr Cys Ala Gly Gly Thr Cys Thr Gly
1895            1900                1905

Thr Thr Gly Thr Gly Cys Ala Gly Cys Cys Cys Ala Gly Ala Thr
1910            1915                1920

Gly Gly Ala Cys Ala Cys Cys Thr Gly Thr Thr Cys Thr Cys
1925            1930                1935

Cys Ala Ala Ala Ala Ala Ala Ala Ala Ala Ala Ala
1940            1945                1950

Ala Ala
1955

<210> SEQ ID NO 5
<211> LENGTH: 33
<212> TYPE: DNA
<213> ORGANISM: Artificial
<220> FEATURE:
<223> OTHER INFORMATION: primer

<400> SEQUENCE: 5
gccgccacca tgggccccgg cgaggcgctg ctg                             33

<210> SEQ ID NO 6
<211> LENGTH: 24
<212> TYPE: DNA
<213> ORGANISM: Artificial
<220> FEATURE:
<223> OTHER INFORMATION: primer

```
<400> SEQUENCE: 6
tcagtgtgtc tgctgcaggc agga                                              24

<210> SEQ ID NO 7
<211> LENGTH: 32
<212> TYPE: DNA
<213> ORGANISM: Artificial
<220> FEATURE:
<223> OTHER INFORMATION: primer

<400> SEQUENCE: 7
gccgccacca tgaactcgtg ggacgcgggc ct                                     32

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
ccttcaagac accggcagaa t                                                 21
```

MODULATORS OF THE ORPHAN G PROTEIN-COUPLED RECEPTORS GPR78 AND GPR26

RELATED APPLICATIONS

This application claims the benefit of priority under 35 U.S.C. §119(e) to U.S. Provisional Patent Application No. 60/872,124, filed Dec. 1, 2006, the contents of which are hereby incorporated by reference in its entirety.

BACKGROUND OF THE INVENTION

Genistein is an isoflavone found abundantly in soy products and other plants. Genistein has been reported to have beneficial effects in preventing cardiovascular disorders, hormone-related disorders, and cancers ([1-5]). Genistein has also been reported to induce apoptosis and inhibit activation of NF-kappaB and Akt signaling pathways ([6-8]), act as an antioxidant ([9, 10]), manifest biological effects through interaction with the estrogen receptor ([7, 11]), and inhibit protein tyrosine kinase ([12, 13]) and cellular proliferation in vascular endothelium and smooth muscle ([14, 15]). In addition, genistein has been found to stimulate insulin secretion in pancreatic beta cells through a cAMP-mediated protein kinase pathway ([16]), suggesting involvement of genistein in metabolic processes. Incubation of genistein with endothelial cells has also been reported to result in the accumulation of intracellular cAMP and to lead to activation of cAMP-dependent protein kinase A ([17]). Involvement of genistein in metabolic processes has also been implied in a publication reporting the regulation of leptin secretion from adipocytes by genistein ([18]).

Diphenyleneiodonium Cl is known as a potent and irreversible inhibitor of NO synthase (NOS). It has been shown to inhibit NOS in cultured peritoneal macrophages (IC50=30 nM), as well as block acetylcholine-induced relaxation of rabbit aortic rings (IC50=0.3 μM) ([40]). It also inhibits other NADPH-utilizing flavoproteins such as NADPH oxidase of human neutrophils ([41]) and macrophages ([42]). Diphenyleneiodonium Cl has the following structure:

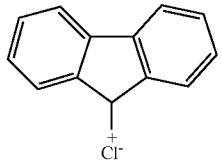

Sanguinarine is an alkaloid obtained from the bloodroot plant, Sanguinaria canadensis, which is used to treat and remove dental plaque. Sanguinarine is known to have anti-microbial, anti-inflammatory and anti-oxidant properties. It also has anti-proliferative, pro-apoptosis effects in some cancer cell lines ([43, 44, 45, 46]). Sanguinarine Cl has the following structure:

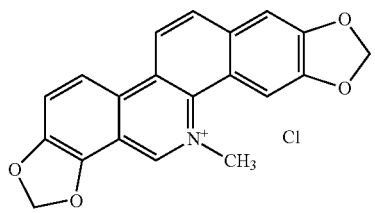

The sanguinarine family of plant alkaloids also includes structurally related amphipathic cations such as berberine and palmatine.

G protein-coupled receptors ("GPCRs") are a family of cell surface receptors that upon activation by their endogenous ligands transmit extracellular signal into cells to control a variety of cellular functions. The most commonly recognized signaling transduction pathways are those mediated by the G protein families including Gq, Gs, Gi, and Go. Recently other pathways independent of G proteins are also found such as beta-arrestin-mediated signal transduction.

GPR78 has been cloned and found to be expressed mainly in pituitary and placenta ([19]), and has been implicated in a genetic linkage study in bipolar affective disorder and schizophrenia ([20]). There have been no reports on the identification of ligands for GPR78 to date.

GPR78 has also cloned and found to be expressed mainly in the brain. There have been no reports on the identification of ligands for GPR26 to date.

SUMMARY OF THE INVENTION

The invention is based, in part, on the identification of certain isoflavones, including genistein and daidzein, as ligands for the GPR78 and GPR26 polypeptides. The invention is also based, in part, on the identification of diphenyleneiodonium Cl, sanguinarine Cl, and analogs thereof as antagonists of the GPR78 and GPR26 polypeptides. The invention relates to the use of the interaction between the GPR78 polypeptide or the GPR26 polypeptide, and their identified ligands and/or antagonists, as the basis for screening methods for the identification of agents that modulate (for example by agonizing or antagonizing) the activity of these receptors, and for diagnostic and therapeutic purposes. The agents identified by the screening methods of the invention have use in the treatment of GPR78- and/or GPR26-mediated disorders, including, but not limited to, neurological disorders (such as anxiety disorders), metabolic disorders, cardiovascular disorders, hormone-related disorders, vascular disorders and hyperproliferative disorders (such as cancer).

The invention encompasses the use of isoflavones or analogs thereof, including the use of genistein and daidzein, for the treatment of GPR78- and/or GPR26-mediated disorders. The invention also encompasses the use of diphenyleneiodonium Cl, sanguinarine Cl, analogs of diphenyleneiodonium Cl or analogs of sanguinarine Cl for the treatment of GPR78- and/or GPR26-mediated disorders.

The invention encompasses compositions and kits comprising: a GPR78 polypeptide and a ligand and/or antagonist for this polypeptide; a GPR26 polypeptide and a ligand and/or antagonist for this polypeptide; or a GPR78 polypeptide, a GPR26 polypeptide and one or more ligands and/or antagonists for these polypeptides.

In one embodiment, the invention encompasses a method for identifying a modulator of a GPR78 or GPR26 polypeptide, comprising: (a) contacting a GPR78 or GPR26 polypeptide or a fragment thereof with a ligand of the GPR78 or GPR26 polypeptide in the presence and absence of a test sample, under conditions permitting the binding of the ligand to the GPR78 or GPR26 polypeptide; and (b) measuring the amount of the ligand that is bound to the GPR78 or GPR26 polypeptide, wherein a modulator of the GPR78 or GPR26 polypeptide in the test sample is identified by measuring a change in binding of the ligand to the GPR78 or GPR26 polypeptide in the presence and absence of the test sample. In one embodiment, the ligand is labeled, and the binding of the ligand to the GPR78 or GPR26 polypeptide is measured by detecting the label. The label may be any detectable label. In one embodiment, the label is selected from the group consisting of a radioisotope, a fluorophore, a quencher of fluorescence, an enzyme, a dye, a luminophore, and an affinity tag.

The invention also encompasses a method for identifying a modulator of a GPR78 or GPR26 polypeptide, comprising: (a) contacting a GPR78 or GPR26 polypeptide or a fragment thereof with a ligand of the GPR78 or GPR26 polypeptide in the presence and absence of a test sample; and (b) measuring the activity of the GPR78 or GPR26 polypeptide, wherein a modulator of the GPR78 or GPR26 polypeptide in the test sample is identified by measuring a change in the activity of the GPR78 or GPR26 polypeptide in the presence and absence of the test sample.

The invention also encompasses a method for identifying a modulator of a GPR78 or GPR26 polypeptide, comprising: (a) contacting a GPR78 or GPR26 polypeptide or a fragment thereof with a test sample in the presence and absence of a ligand of the GPR78 or GPR26 polypeptide; and (b) measuring the activity of the GPR78 or GPR26 polypeptide, wherein a modulator of the GPR78 or GPR26 polypeptide in the test sample is identified by measuring a change in the activity of the GPR78 or GPR26 polypeptide in the presence and absence of the known ligand.

The invention also encompasses a method for identifying a modulator of a GPR78 or GPR26 polypeptide, comprising: (a) contacting a GPR78 or GPR26 polypeptide or a fragment thereof with a test sample; and (b) measuring the activity of the GPR78 or GPR26 polypeptide, wherein a modulator of the GPR78 or GPR26 polypeptide in the test sample is identified by comparing the activity of the GPR78 or GPR26 polypeptide in the presence of the test sample to a standard value, wherein the standard value is based on the activity of the GPR78 or GPR26 polypeptide in the presence of a ligand of the GPR78 or GPR26 polypeptide.

The invention also encompasses a method for identifying a modulator of a GPR78 or GPR26 polypeptide, comprising: (a) contacting a GPR78 or GPR26 polypeptide or a fragment thereof with a ligand and a test sample; and (b) measuring the activity of the GPR78 or GPR26 polypeptide, wherein a modulator of the GPR78 or GPR26 polypeptide in the test sample is identified by comparing the activity of the GPR78 or GPR26 polypeptide in the presence of the ligand and the test sample to a standard value, wherein the standard value is based on the activity of the GPR78 or GPR26 polypeptide in the presence of the ligand and an antagonist of the GPR78 or GPR26 polypeptide.

In any of the above-described, methods for identifying a modulator of a GPR78 or GPR26 polypeptide, the ligand may be an isoflavone or an analog thereof, or a phytoestrogen or an analog thereof. In one embodiment, the ligand is genistein or an analog thereof. In another embodiment, the ligand is daidzein or an analog thereof. In another embodiment, the ligand is biochanin A or an analog thereof. In another embodiment, the ligand is formononetin or an analog thereof. In one embodiment, the antagonist is diphenyleneiodonium Cl or an analog thereof. In another embodiment, the antagonist is sanguinarine Cl or an analog thereof.

In any of the above-described methods for identifying a modulator of a GPR78 or GPR26 polypeptide, the modulator is suitable to treat a GPR78- or GPR26-mediated disorder. In one embodiment, the GPR78- or GPR26-mediated disorder is an anxiety disorder. In another embodiment, the GPR78- or GPR26-mediated disorder is a metabolic disorder.

In any of the above-described methods for identifying a modulator of a GPR78 or GPR26 polypeptide, the modulator may be an agonist or an antagonist. In one embodiment, the modulator is an agonist of GPR78 or GPR26. In another embodiment, the modulator is an antagonist of GPR78 or GPR26.

In any of the above-described methods for identifying a modulator of a GPR78 or GPR26 polypeptide, the GPR78 or GPR26 polypeptide or fragment thereof may be: on the surface of a mammalian cell, on a cell membrane preparation, on a lipid vesicle, immobilized to a solid surface, or substantially purified.

In any of the above-described methods for identifying a modulator of a GPR78 or GPR26 polypeptide, the test sample may comprise an agent selected from the group consisting of: a peptide, a polypeptide, an antibody or antigen-biding fragment thereof, a lipid, a carbohydrate, a nucleic acid, and a small organic molecule.

In any of the above-described methods for identifying a modulator of a GPR78 or GPR26 polypeptide, the activity of the GPR78 or GPR26 polypeptide may be measured by measuring a change in the level of a second messenger. In one embodiment, the second messenger is cAMP. In one embodiment, the change in the level of cAMP is measured using a luciferase reporting system. In one embodiment, the change in the level of cAMP is measured using a cell that has been stably transformed with a cAMP-responsive luciferase reporter gene.

The invention also encompasses a method for identifying an agent to treat a GPR78- or GPR26-mediated disorder, comprising screening for modulators of the GPR78 or GPR26 polypeptide. In one embodiment, the GPR78- or GPR26-mediated disorder is an anxiety disorder. In another embodiment, the GPR78- or GPR26-mediated disorder is a metabolic disorder.

The invention also encompasses a method of treating a GPR78- or GPR26-mediated disorder, comprising administering to a subject in need thereof, an effective amount of a composition comprising a modulator of a GPR78 or GPR26 polypeptide. In one embodiment, the subject is human. In one embodiment, the modulator is an agonist of the GPR78 or GPR26 receptor. In another embodiment, the modulator is an antagonist of the GRP78 or GPR26 receptor. In one embodiment, the modulator is an isoflavone or an analog thereof. In one embodiment, the modulator is a phytoestrogen or an analog thereof. In another embodiment, the modulator is genistein or an analog thereof. In another embodiment, the modulator is daidzein or an analog thereof. In another embodiment, the modulator is biochanin A or an analog thereof. In another embodiment, the modulator is formononetin or an analog thereof. In another embodiment, the modulator is not an isoflavone or an analog thereof. In another embodiment, the modulator is not genistein or an analog thereof. In another embodiment, the modulator is not daidzein or an analog thereof. In another embodiment, the modulator is diphenyleneiodonium Cl or an analog thereof. In another embodiment, the modulator is sanguinarine Cl or an analog thereof.

In one embodiment, the GPR78- or GPR26-mediated disorder is a neurological disorder. In one embodiment, the neurological disorder is an anxiety disorder such as a generalized anxiety disorder, an obsessive-compulsive disorder (OCD), a panic disorder, a post-traumatic stress disorder (PTSD) or a social phobia (also referred to as social anxiety disorder). In one embodiment, the neurological disorder is bipolar affective disorder or schizophrenia. In another embodiment, the neurological disorder is Alzheimer's disease. In one embodiment, the GPR78- or GPR26-mediated disorder is a neurological disorder and the modulator is: an isoflavone or an analog thereof, a phytoestrogen or an analog thereof, genistein or an analog thereof, daidzein or an analog thereof, biochanin A or an analog thereof, formononetin or an analog thereof, diphenyleneiodonium Cl or an analog thereof, or sanguinarine Cl or an analog thereof.

In one embodiment, the GPR78- or GPR26-mediated disorder is a metabolic disorder. In one embodiment, the metabolic disorder is obesity or diabetes.

In one embodiment, the disorder is a GPR26-mediated disorder, and the invention encompasses the use of a GPR26 agonist to treat the GPR26-mediated disorder. In one embodiment, the GPR26-mediated disorder is a metabolic disorder such as obesity or diabetes. In one embodiment, the GPR26 agonist is an antibody or an antigen-binding fragment thereof that binds to and activates GPR26.

In one embodiment, the disorder is a GPR26-mediated disorder, and the invention encompasses the use of a GPR26 antagonist to treat the GPR26-mediated disorder. In one embodiment, the GPR26-mediated disorder is an anxiety disorder such as a generalized anxiety disorder, an obsessive-compulsive disorder (OCD), a panic disorder, a post-traumatic stress disorder (PTSD) or a social phobia (also referred to as social anxiety disorder). In one embodiment, the GPR26 antagonist is an antibody or an antigen-binding fragment thereof that binds to and inactivates GPR26.

In one embodiment, the GPR78- or GPR26-mediated disorder is a CNS-mediated disorder.

In one embodiment, the GPR78- or GPR26-mediated disorder is a cardiovascular disorder. In one embodiment, the cardiovascular disorder is coronary heart disease. In one embodiment, the cardiovascular disorder is selected from the group consisting of arteriosclerosis, angina, high blood pressure, high cholesterol, heart attack, stroke or arrhythmia.

In one embodiment, the GPR78- or GPR26-mediated disorder is a hyperproliferative disorder. In one embodiment, the hyperproliferative disorder is cancer. In one embodiment, the cancer is breast cancer or prostate cancer.

In one embodiment, the GPR78- or GPR26-mediated disorder is a hormone-mediated disorder. In one embodiment, the hormone-mediated disorder is menopause or pre-menopause, or any of the symptoms related to menopause or pre-menopause such as hot-flashes and bone loss.

In one embodiment, the GPR78- or GPR26-mediated disorder is a condition resulting in bone loss. In one embodiment, the condition resulting in bone loss is osteoporosis.

In one embodiment, the GPR78- or GPR26-mediated disorder is an inflammatory disorder. In one embodiment, the inflammatory disorder involves the digestive system.

In one embodiment, the GPR78- or GPR26-mediated disorder is a disorder of the digestive system.

In one embodiment, the GPR78- or GPR26-mediated disorder is a disorder of the urethra.

In one embodiment, the GPR78- or GPR26-mediated disorder is an angiogenesis-related disorder.

The invention also encompasses a method of modulating angiogenesis comprising administering to a subject in need thereof, an effective amount of pharmaceutical composition comprising a modulator of a GPR78 or GPR26 polypeptide. In one embodiment, the subject suffers from, or is at risk of developing, a hyperproliferative disorder, diabetic blindness, age-related macular degeneration, rheumatoid arthritis or psoriasis, and the modulator is an agonist of the GPR78 or GPR26 polypeptide. In one embodiment, the agonist of the GPR78 or GPR26 polypeptide is not genistein or daidzein. In one embodiment, the subject suffers from, or is at risk of developing, coronary artery disease, stroke or delayed wound healing, and wherein the modulator of the GPR78 or GPR26 polypeptide is an antagonist of the GPR78 or GPR26 polypeptide.

The invention also encompasses a method of modulating the activity of the GPR78 or GPR26 polypeptide comprising administering to a subject having or at risk of developing a GPR78- or GPR26-mediated disorder an effective amount of a composition comprising a modulator of a GPR78 or GPR26 polypeptide.

The invention also encompasses a method of modulating the activity of the GPR78 or GPR26 polypeptide comprising contacting a cell with a composition comprising a modulator of a GPR78 or GPR26 polypeptide.

The invention also encompasses a pharmaceutical composition comprising: (a) an agonist or antagonist of GPR78 or GPR26; and (b) a pharmaceutically acceptable carrier. In one embodiment, the agonist or antagonist of GPR78 or GPR26 is a small molecule that binds to GPR78 or GPR26. In one embodiment, the small molecule is genistein or an analog thereof. In one embodiment, the small molecule is daidzein or an analog thereof. In one embodiment, the small molecule is diphenyleneiodonium Cl or an analog thereof. In one embodiment, the small molecule is sanguinarine Cl or an analog thereof. In another embodiment, the agonist or antagonist of GPR78 or GPR26 is an antibody or antigen-binding fragment thereof that specifically binds to a GPR78 or GPR26 polypeptide and blocks the binding of GPR78 or GPR26 to its ligand.

The invention also encompasses a kit comprising: (a) a GPR78 polypeptide and a ligand for this polypeptide; (b) a GPR26 polypeptide and a ligand for this polypeptide; or (c) a GPR78 polypeptide, a GPR26 polypeptide and one or more ligands for these polypeptides. The invention also encompasses kits comprising: (a) a GPR78 polypeptide, a ligand for this polypeptide and an antagonist for this polypeptide; (b) a GPR26 polypeptide, a ligand for this polypeptide and an antagonist for this polypeptide; or (c) a GPR78 polypeptide, a GPR26 polypeptide, one or more ligands for these polypeptides, and one or more antagonists for these polypeptides.

In one embodiment of any of the kits described above, the ligand of the GPR78 or GPR26 polypeptide is an isoflavone or an analog thereof. In another embodiment, the ligand is a phytoestrogen or an analog thereof. In another embodiment, the ligand is genistein or an analog thereof. In another embodiment, the ligand is daidzein or an analog thereof. In another embodiment, the ligand is biochanin A or an analog thereof. In another embodiment, the ligand is formononetin or an analog thereof. In one embodiment, the antagonist of the GPR78 or GPR26 polypeptide is diphenyleneiodonium Cl or an analog thereof. In another embodiment, the antagonist of the GPR78 or GPR26 polypeptide is sanguinarine Cl or an analog thereof. In one embodiment, the kit comprises a cell expressing a GPR78 or GPR26 polypeptide. In one embodiment, the kit further comprises a container. In one embodiment, the kit further comprises instructions for use.

The invention also encompasses a knockout mouse whose genome comprises a disruption of the endogenous GPR26 gene, wherein the knockout mouse exhibits reduced anxiety. The invention also encompasses a knockout mouse whose genome comprises a disruption of the endogenous GPR26 gene, wherein the knockout mouse exhibits reduced metabolic activity.

In one embodiment of the knockout mouse described above, one of the alleles of the endogenous GPR26 gene has been inactivated. In another embodiment of the knockout mouse described above, both alleles of the endogenous GPR26 gene have been inactivated.

The invention further encompasses a descendant of any of the knockout mice described above, obtained by breeding with animals of the same or another genotype. The invention also encompasses a primary cell culture or a secondary cell line derived from any of the knockout mice described above. The invention also encompasses a tissue explant, a culture of a tissue explant, an organ explant, or a culture of an organ explant derived from any of the knockout mice described above. The invention also encompasses a tissue extract or a cell extract derived from any of the knockout mice described above.

Also within the scope of the present invention is a method of producing any of the knockout mice described above, comprising the step of replacing at least a portion of the GPR26 gene in an embryonic stem cell by homologous recombination with a DNA sequence comprising at least a portion of one exon of the GPR26 coding sequence. In one embodiment, the method further comprises the steps of: (a) providing a knockout construct for GPR26; (b) introducing the knockout construct into mouse embryonic stem cells; (c) selecting embryonic stem cells that have integrated the knockout construct by homologous recombination; (d) introducing the embryonic stem cells containing the knockout construct into mouse blastocysts; (e) transplanting the blastocysts into a pseudopregnant mouse; and (f) allowing the blastocysts to develop to a chimeric mouse to enable germline transmission of the disrupted GPR26 gene.

The invention also encompasses a method of screening a test agent for anxiolytic or anxiety-inducing activity, comprising the steps of: (a) administering the test agent to any of the knockout mice described above; (b) determining the effect of the test agent on the knockout mouse; and (c) relating the effect of the test agent on the knockout mouse to the anxiolytic or anxiety-inducing activity of said agent. In one embodiment, step (b) comprises comparing the knockout mouse to a second knockout mouse, e.g., a control knockout mouse, not administered the test agent.

The invention also encompasses a method of screening a test agent for metabolic activity, comprising the steps of: (a) administering the test agent to any of the knockout mice described above; (b) determining the effect of the test agent on the knockout mouse; and (c) relating the effect of the test agent on the knockout mouse to the metabolic activity of said agent. In one embodiment, wherein step (b) comprises comparing the knockout mouse to a second knockout mouse, e.g., a control knockout mouse, not administered the test agent.

Also within the scope of the present invention is the use of any of the knockout mice described above as a model for an anxiety disorder. The invention further encompasses the use of any of the knockout mice described above as a model for a metabolic disorder. In one embodiment, the metabolic disorder is obesity.

The invention also encompasses a method of determining whether an individual is susceptible to a metabolic disorder, comprising the steps of: (a) determining the level of expression of a GPR26 polypeptide in a sample isolated from the individual, and (b) determining, compared to a control, whether the individual from which the sample was isolated has or is susceptible to a metabolic disorder. In one embodiment, the metabolic disorder is obesity.

The invention also encompasses a method of determining whether an individual is susceptible to a metabolic disorder, comprising the steps of: (a) determining the level of biological activity of a GPR26 polypeptide in a sample isolated from the individual, and (b) determining, compared to a control, whether the individual from which the sample was isolated has or is susceptible to a metabolic disorder. In one embodiment, the metabolic disorder is obesity.

DETAILED DESCRIPTION OF THE INVENTION

Figure 1:
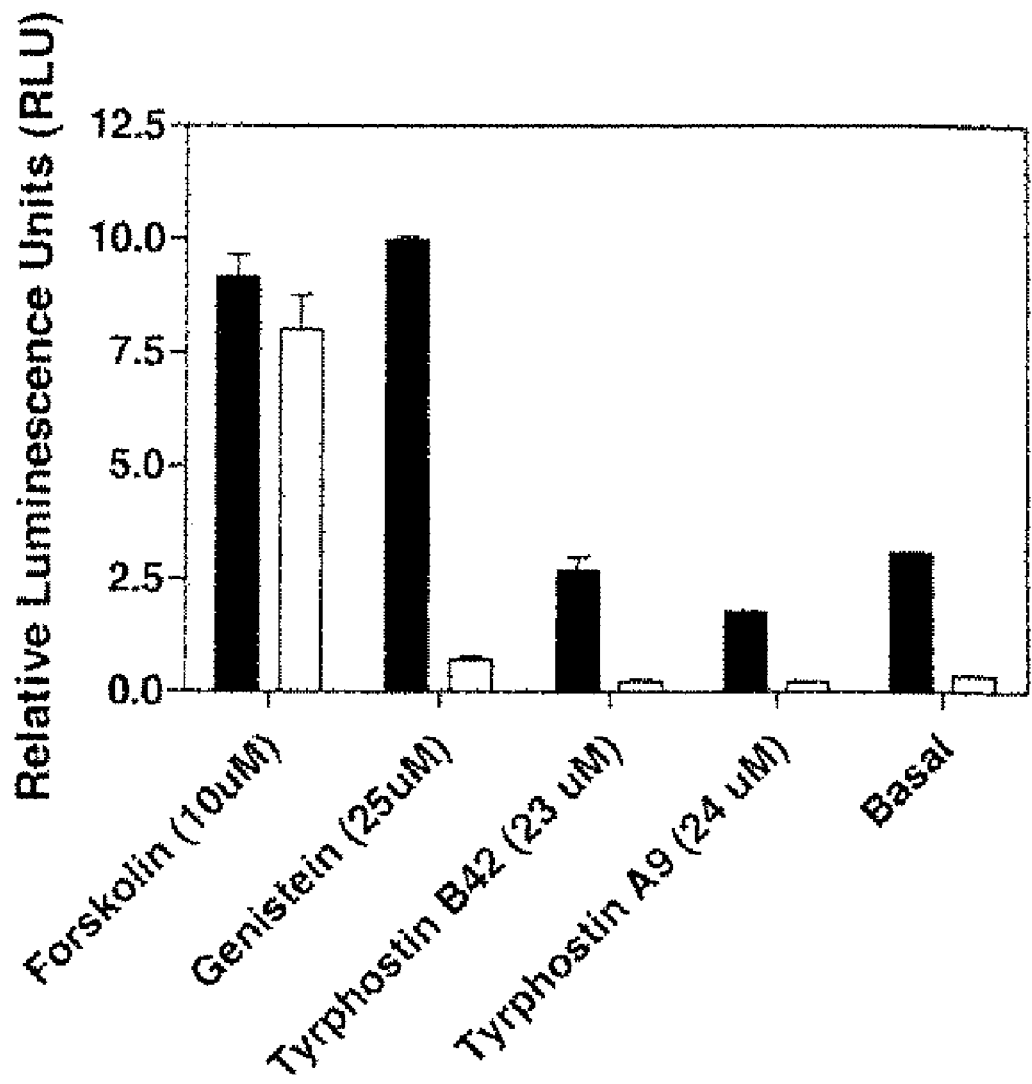
FIG. 1. Genistein stimulates cAMP accumulations in GPR78-expressing HEK293/cre-luc cells (filled bars) and vector control HEK293 cells (empty bars). Genistein, Tyrphostin B42, Tyrphostin A9, and buffer were incubated with cells to stimulate intracellular cAMP production. Forskolin at 10 μM was used as control as it stimulates adenylyl cyclase directly in both GPR78 cells and mock cells. Data is expressed as arbitrary unit, mean±SD.

As used herein, including the appended claims, the singular forms of words such as "a," "an," and "the" include their corresponding plural references unless the context clearly dictates otherwise.

All references cited herein are incorporated herein by reference to the same extent as if each individual publication, patent, or published patent application was specifically and individually indicated to be incorporated by reference.

GPR78 Polypeptides and GPR26 Polypeptides

As used herein, the term "GPR78 polypeptide" refers to the G protein-coupled receptor 78, and to variants and fragments of this receptor. In one embodiment, the GPR78 polypeptide comprises the amino acid sequence of SEQ ID NO: 1 (GenBank Accession No. NP_543009) or a subsequence thereof.

As used herein, the term "GPR26 polypeptide" refers to the G protein-coupled receptor 26, and to variants and fragments of this receptor. In another embodiment, the GPR26 polypeptide comprises the amino acid sequence of SEQ ID NO: 3 (GenBank Accession No. NP_703143) or a subsequence thereof.

Fragments of the GPR78 polypeptide or the GPR26 polypeptide preferably comprise at least about 4, 5, 6 or 7 (e.g., 8, 9, 10 or 11), preferably at least about 12 (e.g., 13, 14, 15, 16, 17, 18 or 19), more preferably at least about 20 (e.g., 21, 22, 23, 24, 25, 26, 27, 28 or 29), and most preferably at least about 30 (e.g., 31, 32, 33, 34, 35, 36, 37, 38, 39, 40, 50, 60, 70, 80, 90, 100, 124 or 136) or more contiguous amino acid residues. In one embodiment, fragments of the GPR78 polypeptide comprise at least about 4, 5, 6 or 7, preferably at least about 12, more preferably at least about 20, and most preferably at least about 30 or more contiguous amino acid residues from SEQ ID NO: 1 (GenBank Accession No. NP_543009). In another embodiment, fragments of the GPR26 polypeptide comprise at least about 4, 5, 6 or 7, preferably at least about 12, more preferably at least about 20, and most preferably at least about 30 or more contiguous amino acid residues from SEQ ID NO: 3 (GenBank Accession No. NP_703143). In some preferred embodiments, fragments of the GPR78 polypeptide substantially retain the ability to bind to a natural ligand of the GPR78 polypeptide; and fragments of the GPR26 polypeptide substantially retain the ability to bind to a natural ligand of the GPR26 polypeptide. In other embodiments, variants of the GPR78 polypeptide substantially retain the ability to activate the intracellular response initiated by the binding of a ligand to the GPR78 polypeptide; and variants of the GPR26 polypeptide substantially retain the ability to activate the intracellular response that initiated by the binding of a ligand to the GPR26 polypeptide.

"Variant(s)", as the term is used herein, refers to polypeptides that differ from a reference polypeptide, but which retain one or more of the biological functions or activities of the reference polypeptides. In the one embodiment, the reference GPR78 polypeptide will comprise the amino acid sequence disclosed at SEQ ID NO: 1 (GenBank Accession No. NP_543009). In another embodiment, the reference GPR26 polypeptide will comprise the amino acid sequence disclosed at SEQ ID NO: 3 (GenBank Accession No. NP_703143). In some embodiments, variants of the GPR78 polypeptide substantially retain the ability to bind to a natural ligand of the GPR78 polypeptide. In other embodiments, variants of the GPR78 polypeptide substantially retain the ability to activate the intracellular response initiated by the binding of a ligand to the GPR78 polypeptide. In some embodiments variants of the GPR26 polypeptide substantially retain the ability to bind to a natural ligand of the GPR26 polypeptide. In other embodiments variants of the GPR26 polypeptide substantially retain the ability to activate the intracellular response that initiated by the binding of a ligand to the GPR26 polypeptide.

Variants of the GPR78 polypeptide or the GPR26 polypeptide include variants that are closely similar overall and, in many regions, identical to the reference polypeptides. For example, the variant and the reference polypeptides may differ in amino acid sequence by one or more amino acid substitutions, one or more amino acid additions, one or more amino acid deletions, or combinations of any of the above. Some amino acid substitutions are preferably "conservative", with residues replaced with physically or chemically similar residues, such as Gly/Ala, Asp/Glu, Val/Ile/Leu, Lys/Arg, Asn/Gln and Phe/Trp/Tyr.

The variants of the GPR78 polypeptide or the GPR26 polypeptide also include variants in which one or more of the amino acid residues have been modified and/or include a substituent group. Modifications of amino acid residues may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine.

Other variants of the GPR78 polypeptide or the GPR26 polypeptides may contain modifications, such as incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those that have molecular shapes similar to phosphate groups.

Variants of the GPR78 polypeptide or the GPR26 polypeptide also include variants in which a GPR78 polypeptide, a GPR26 polypeptide, or a fragment of either one of these polypeptides is fused or joined to another polypeptide to create a chimeric polypeptide. In one embodiment a fragment of a GPR78 polypeptide or a fragment of a GPR26 polypeptide is fused to a fragment of another GPCR polypeptide, to create a chimeric GPCR protein. See, e.g., Gupte et al., *Proc. Wad. Acad. Sci. USA* 101(6):1508-13 (2004).)

Variants of the GPR78 polypeptide or the GPR26 polypeptide also include variants in which a GPR78 polypeptide, a GPR26 polypeptide, or a fragment of either one of these polypeptides, is fused with another compound, such as a compound that increases the half-life of the polypeptide (for example, polyethylene glycol).

Variants of the GPR78 polypeptide or the GPR26 polypeptide also include variants in which the GPR78 polypeptide, the GPR26 polypeptide, or a fragment of either one of these polypeptides, is fused to a leader or secretory sequence or a sequence which is employed for purification of the mature polypeptide or a pro-protein sequence.

In one embodiment, the variant of the GPR78 polypeptide will have at least 80% amino acid identity, preferably 85%, 90%, 95%, or higher, up to and including 100% identity, to a GPR78 polypeptide comprising the amino acid sequence of SEQ ID NO:1 or to a fragment thereof. In another embodiment, the polynucleotide encoding this variant polypeptide will have at least 80% nucleic acid identity, preferably 85%, 90%, 95%, or higher, up to and including 100% identity, to a polynucleotide comprising SEQ ID NO: 2 or to a fragment thereof. In another embodiment, the variant of the GPR78 polypeptide will have at least 50% amino acid homology (similarity), preferably at least 60%, 70%, 80%, 90%, 95%, or higher, up to and including 100% homology, a GPR78 polypeptide comprising the amino acid sequence of SEQ ID NO:1 or to a fragment thereof. In yet another embodiment, the polynucleotide encoding this variant polypeptide will have at least 50% nucleic acid homology, preferably 60%, 70%, 80%, 90%, 95%, or higher, up to and including 100% homology, to a polynucleotide comprising SEQ ID NO: 2 or to a fragment thereof.

In another embodiment, the variant of the GPR26 polypeptide will have at least 80% amino acid identity, preferably 85%, 90%, 95%, or higher, up to and including 100% identity, to a GPR26 polypeptide comprising the amino acid sequence of SEQ ID NO:3 or to a fragment thereof. In another embodiment, the polynucleotide encoding this variant polypeptide will have at least 80% nucleic acid identity, preferably 85%, 90%, 95%, or higher, up to and including 100% identity, to a polynucleotide comprising SEQ ID NO: 4 or to a fragment thereof. In another embodiment, the variant of the GPR26 polypeptide will have at least 50% amino acid homology (similarity), preferably 60%, 70%, 80%, 90%, 95%, or higher, up to and including 100% homology, to a GPR26 polypeptide comprising the amino acid sequence of SEQ ID NO:3 or to a fragment thereof. In yet another embodiment, the polynucleotide encoding this variant polypeptide will have at least 50% nucleic acid homology, preferably 60%, 70%, 80%, 90%, 95%, or higher, up to and including 100% homology, to a polynucleotide comprising SEQ ID NO: 4 or to a fragment thereof.

Sequence "identity" refers to exact matches between the nucleotides or amino acids of two sequences which are being compared.

Sequence "similarity" or "homology" refers to both exact matches between the amino acids of two polypeptides which are being compared in addition to matches between nonidentical, biochemically related amino acids. Biochemically related amino acids share similar properties and may be interchangeable. Amino acids with similar properties which may be interchangeable are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, praline, tyrosine, phenylalanine, tryptophan and methionine; acidic amino acids which may be interchangeable include aspartic acid and glutamic acid and basic amino acids which may be interchangeable include histidine, lysine and arginine.

Sequence "identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A.M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., et al. (1988), *SIAM J. Applied Math*, 48:1073. Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., (1984) *Nucleic Acids Research* 12 (1): 387), BestFit, BLASTP, BLASTN, and FASTA (Altschul, S. F., et al., (1990) *J. Mol. Biol.* 215:403-410. The BLASTX program is publicly available from NCBI and other sources (BLAST Manual, Altschul, S., et al., NCBI NLM NIH Bethesda, Md. 20894; Altschul, S., et al., (1990) *J. Mol. Biol.* 215:403-410. The well-known Smith Waterman algorithm may also be used to determine identity.

Preferred parameters for polypeptide sequence comparison include the following: 1) Algorithm: Needleman and Wunsch, *J. Mol. Biol.* 48:443-453 (1970):

Comparison matrix: BLOSSUM62 from Hentikoff and Hentikoff, Proc. Natl. Acad. Sci. USA. 89:10915-10919 (1992)

Gap Penalty: 12

Gap Length Penalty: 4

A program useful with these parameters is publicly available as the "GAP" program from Genetics Computer Group, located in Madison, Wis. The aforementioned parameters are the default parameters for peptide comparisons (along with no penalty for end gaps).

Preferred parameters for polynucleotide comparison include the following: 1) Algorithm: Needleman and Wunsch, *J. Mol. Biol.* 48:443-453 (1970):

Comparison matrix: matches=+10, mismatch=0

Gap Penalty: 50

Gap Length Penalty: 3

A program useful with these parameters is publicly available as the "GAP" program from Genetics Computer Group, located in Madison, Wis.

Variants of the GPR78 polypeptide or the GPR26 polypeptide also include polypeptides encoded by polynucleotides which hybridize to the polynucleotides encoding the reference polypeptides or to their complementary sequences. Thus, in one embodiment, a variant of the GPR78 polypeptide is encoded by a polynucleotide that hybridizes to the complement of SEQ ID NO: 2. In another embodiment, a variant of the GPR26 polypeptide is encoded by a polynucleotide that hybridizes to the complement of SEQ ID NO: 4. Preferably, the nucleic acids hybridize under low stringency conditions, more preferably under moderate stringency conditions and most preferably under high stringency conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., *Molecular Cloning: A Laboratory Manual*). The conditions of temperature and ionic strength determine the "stringency" of the hybridization. Typical, low stringency, hybridization conditions may be 55° C., 5×SSC, 0.1% SDS, 0.25% milk, and no formamide; or 30% formamide, 5×SSC, 0.5% SDS. Typical, moderate stringency hybridization conditions are similar to the low stringency conditions except the hybridization is carried out in 40% formamide, with 5× or 6×SSC. High stringency hybridization conditions are similar to low stringency conditions except the hybridization conditions may be carried out in 50% formamide, 5× or 6×SSC and, optionally, at a higher temperature (e.g., 57° C., 59° C., 60° C., 62° C., 63° C., 65° C. or 68° C.). Typically, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. Typical, selective hybridization conditions occur when there is at least about 55% identity over a stretch of at least about 30 nucleotides, preferably at least about 65% over at least about 25 nucleotides, more preferably at least about 75% to about 95%, or more, over about 20 nucleotides or more. For hybrids of greater than 100 nucleotides in length, equations for calculating the melting temperature have been derived (see Sambrook, et al., supra). For hybridization with shorter nucleic acids, i.e., oligonucleotides, the position of mismatches becomes more important, and the length of the oligonucleotide determines its specificity (see Sambrook, et al., supra).

Typically, selective hybridization will occur when there is at least about 55% homology over a stretch of at least about 30 nucleotides, preferably at least about 65% over a stretch of at least about 25 nucleotides, more preferably at least about 75%, and most preferably at least about 90% over about 20 nucleotides. See, e.g., Kanehisa, *Nucleic Acids Res.* 12:203 (1984). The lengths of such homology comparisons may encompass longer stretches and in certain embodiments may cover a sequence of at least about 17, preferably at least about 25, more preferably at least about 50, and most preferably at least about 75 nucleotide residues.

An indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

Variants of the GPR78 polypeptide or the GPR26 polypeptide (or fragments of these polypeptides) may comprise various modifications resulting from the method of making the polypeptide. For polypeptides made by expressing a cloned gene in a host, for instance, the nature and extent of the modifications in large part will be determined by the host cell's post-translational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cells often carry out the same post-translational glycosylations as mammalian cells do and, for this reason, insect cell expression systems have been developed to express efficiently mammalian proteins having the native patterns of glycosylation, inter alia. Similar considerations apply to other modifications.

Variants of the GPR78 polypeptide or the GPR26 polypeptide (or fragments of these polypeptides) include glycosylation variants. Glycosylation variants include, e.g., analogs made by modifying glycosylation patterns during synthesis and processing in various alternative eukaryotic host expression systems, or during further processing steps. Particularly preferred methods for producing glycosylation modifications include exposing the GPR78 polypeptide or the GPR26 polypeptide to glycosylating enzymes derived from cells that normally carry out such processing, such as mammalian glycosylation enzymes. Alternatively, deglycosylation enzymes can be used to remove carbohydrates attached during production in eukaryotic expression systems.

Variants of the GPR78 polypeptide or the GPR26 polypeptide may or may not occur naturally.

Variants of the GPR78 polypeptide or the GPR26 polypeptide can be prepared by chemical synthesis or by using site-directed mutagenesis (Gillman et al., *Gene* 8:81 (1979); Roberts et al., *Nature*, 328:731 (1987) or Innis (Ed.), 1990, *PCR Protocols: A Guide to Methods and Applications*, Academic Press, New York, N.Y.) or the polymerase chain reaction method (PCR) (Saiki et al., *Science* 239:487 (1988)), as exemplified by Daugherty et al. (*Nucleic Acids Res.* 19:2471 (1991) to modify nucleic acids encoding the complete receptors. Adding epitope tags for purification or detection of recombinant products is envisioned.

General techniques for nucleic acid manipulation and expression that can be used to make the variants discussed above are described generally, e.g., in Sambrook, et al., *Molecular Cloning: A Laboratory Manual* (2d ed.), 1989, Vols. 1-3, Cold Spring Harbor Laboratory. Techniques for the synthesis of polypeptides are described, for example, in Merrifield, *J. Amer. Chem. Soc.* 85:2149 (1963); Merrifield, *Science* 232:341 (1986); and Atherton et al., *Solid Phase Peptide Synthesis: A Practical Approach*, 1989, IRL Press, Oxford.

Still other variants of the GPR78 polypeptide or GPR26 polypeptide are prepared by the use of agents known in the art for their usefulness in cross-linking proteins through reactive side groups. Preferred derivatization sites with cross-linking agents are free amino groups, carbohydrate moieties and cysteine residues.

Nucleic Acids and Expression Vectors

The terms "oligonucleotide", "polynucleotide", "DNA" and "nucleic acid" are used interchangeably in this application.

As used herein, the term "isolated nucleic acid" means a nucleic acid such as an RNA or DNA molecule, or a mixed polymer, which is substantially separated from other components that are normally found in cells or in recombinant DNA expression systems. These components include but are not limited to ribosomes, polymerases, serum components, and flanking genomic sequences. The term thus embraces a nucleic acid that has been removed from its naturally occurring environment, and includes recombinant or cloned DNA isolates and chemically synthesized analogs or analogs biologically synthesized by heterologous systems. A substantially pure molecule includes isolated forms of the molecule.

An isolated nucleic acid will generally be a homogeneous composition of molecules but may, in some embodiments, contain minor heterogeneity. Such heterogeneity is typically found at the ends of nucleic acid coding sequences or in regions not critical to a desired biological function or activity.

A "recombinant nucleic acid" is defined either by its method of production or structure. Some recombinant nucleic acids are thus made by the use of recombinant DNA techniques which involve human intervention, either in manipulation or selection. Others are made by fusing two fragments that are not naturally contiguous to each other. Engineered vectors are encompassed, as well as nucleic acids comprising sequences derived using any synthetic oligonucleotide process.

This invention further encompasses recombinant DNA molecules and fragments having sequences that are identical or highly homologous to those described herein. The nucleic acids of the invention may be operably linked to DNA segments that control transcription, translation, and DNA replication.

Nucleic acids encoding the GPR78 polypeptide or the GPR26 polypeptide (or fragments of these polypeptides) can be prepared by standard methods. For example, DNA can be chemically synthesized using, e.g., the phosphoramidite solid support method of Matteucci et al. (*J. Am. Chem. Soc.* 103:3185 (1981)), the method of Yoo et al. (*J. Biol. Chem.* 764:17078 (1989)), or other well known methods. This can be done by sequentially linking a series of oligonucleotide cassettes comprising pairs of synthetic oligonucleotides, as described below.

Of course, due to the degeneracy of the genetic code, many different nucleotide sequences can encode the GPR78 polypeptide or the GPR26 polypeptide (or fragments of these polypeptides). The codons can be selected for optimal expression in prokaryotic or eukaryotic systems. Such degenerate variants are of course also encompassed by this invention.

Moreover, nucleic acids encoding the GPR78 polypeptide or the GPR26 polypeptide (or fragments of these polypeptides) can readily be modified by nucleotide substitutions, nucleotide deletions, nucleotide insertions, and inversions of nucleotide stretches. Such modifications result in novel DNA sequences that encode antigens having immunogenic or antigenic activity in common with the wild-type receptors. These modified sequences can be used to produce wild type or mutant receptors, or to enhance expression in a recombinant DNA system.

Insertion of the DNAs encoding the GPR78 polypeptide or the GPR26 polypeptide (or fragments of these polypeptides) into a vector is easily accomplished when the termini of both the DNAs and the vector comprise compatible restriction sites. If this cannot be done, it may be necessary to modify the of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, desired sites may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., *Science* 239:487 (1988). The cleaved vector and the DNA fragments may also be modified if required by homopolymeric tailing.

Recombinant expression vectors used in this invention are typically self-replicating DNA or RNA constructs comprising nucleic acids encoding the GPR78 polypeptide or the GPR26 polypeptide (or fragments of these polypeptides), usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also may contain an origin of replication that allows the vector to replicate independently of the host cell.

Vectors that could be used in this invention include microbial plasmids, viruses, bacteriophage, integratable DNA fragments, and other vehicles that may facilitate integration of the nucleic acids into the genome of the host. Plasmids are the most commonly used form of vector but all other forms of vectors which serve an equivalent function and which are, or become, known in the art are suitable for use herein. See, e.g., Pouwels et al., *Cloning Vectors: A Laboratory Manual,* 1985 and Supplements, Elsevier, N.Y., and Rodriguez et al. (eds.), *Vectors: A Survey of Molecular Cloning Vectors and Their Uses,* 1988, Buttersworth, Boston, Mass.

Expression of nucleic acids encoding the GPR78 polypeptide or the GPR26 polypeptide (or fragments of these polypeptides) can be carried out by conventional methods in either prokaryotic or eukaryotic cells. Although strains of *E. coli* are employed most frequently in prokaryotic systems, many other bacteria such as various strains of *Pseudomonas* and *Bacillus* are know in the art and can be used as well.

Prokaryotic expression control sequences typically used include promoters, including those derived from the B-lactamase and lactose promoter systems (Chang et al., *Nature,* 198:1056 (1977)), the tryptophan (tip) promoter system (Goeddel et al., *Nucleic Acids Res.* 8:4057 (1980)), the lambda $P_L$ promoter system (Shimatake et al., *Nature,* 292:128 (1981)) and the tac promoter (De Boer et al., *Proc. Natl. Acad. Sci. USA* 292:128 (1983)). Numerous expression vectors containing such control sequences are known in the art and available commercially.

Suitable host cells for expressing nucleic acids encoding the GPR78 polypeptide or the GPR26 polypeptide (or fragments of these polypeptides) include prokaryotes and higher eukaryotes. Prokaryotes include both gram negative and positive organisms, e.g., *E. coli* and *B. subtilis*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the GPR78 polypeptide or the GPR26 polypeptide (or fragments of these polypeptides) include but are not limited to those containing the lac promoter (pUC-series); trp promoter (pBR322-trp); Ipp promoter (the pIN-series); lambda-pP or pR promoters (pOTS); or hybrid promoters such as ptac (pDR540). See Brosius et al., "Expression Vectors Employing Lambda-, trp-, lac-, and Ipp-derived Promoters", in Rodriguez and Denhardt (eds.) *Vectors: A Survey of Molecular Cloning Vectors and Their Uses,* 1988, Buttersworth, Boston, pp. 205-236.

Higher eukaryotic tissue culture cells are preferred hosts for the recombinant production of the GPR78 polypeptide or the GPR26 polypeptide (or fragments of these polypeptides). Although any higher eukaryotic tissue culture cell line might be used, including insect baculovirus expression systems, mammalian cells are preferred. Transformation or transfection and propagation of such cells have become a routine procedure. Examples of useful cell lines include HeLa cells, HEK293 cells (human embryonic kidney 293 cell line), Chinese hamster ovary (CHO) cell lines, baby rat kidney (BRK) cell lines, insect cell lines, bird cell lines, and monkey (COS) cell lines.

Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Representative examples of suitable expression vectors include pCR.RTM.3.1, pcDNA1, pCD (Okayama et al., *Mol. Cell. Biol.* 5:1136 (1985)), pMClneo Poly-A (Thomas et al., *Cell* 51:503 (1987)), pUC19, pREP8, pSVSPORT and derivatives thereof, and baculovirus vectors such as pAC 373 or pAC 610.

Protein Purification

The proteins and polypeptides of this invention can be purified by standard methods, including but not limited to salt or alcohol precipitation, preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in *Guide to Protein Purification, Methods in Enzymology*, Vol. 182, M. Deutscher, Ed., 1990, Academic Press, New York, N.Y.

Purification steps can be followed by carrying out assays for ligand binding activity as described below. Particularly where a receptor is being isolated from a cellular or tissue source, it is preferable to include one or more inhibitors of proteolytic enzymes is the assay system, such as phenylmethanesulfonyl fluoride (PMSF).

Screening Methods

The GPR78 polypeptide, the GPR26 polypeptide, or fragments of the GPR78 or GPR26 polypeptide can be employed in screening assays to identify modulators (agonists and antagonists) of the GPR78 polypeptide or GPR26 polypeptide.

As used herein, a "modulator" refers to a natural ligand, an agonist or an antagonist of a receptor.

As used herein, an "agonist" refers to an agent that binds to a receptor and triggers a response that mimics the action of the natural ligand on the receptor. An agonist may be an antibody, or an antigen-binding fragment thereof, that binds to a receptor and triggers a response that mimics the action of the natural ligand on the receptor. An agonist may be a also be a small molecule.

As used herein, an "antagonist" refers to an agent that binds to the receptor and blocks or inhibits the response induced by the action of the natural ligand on the receptor. (The blocking or inhibition of the response induced by the action of the natural ligand on the receptor may be total or partial.) An antagonist may be an antibody, or an antigen-binding fragment thereof, that binds to a receptor and blocks or inhibits the response induced by the action of the natural ligand on the receptor. An antagonist may be a also be small molecule.

As used herein, a "ligand" refers to an agent that is capable of associating or binding to a receptor. For example, as disclosed herein, genistein and daidzein are ligands of the GPR78 and GPR26 polypeptides.

As used herein, an "analog" refers to a chemical with a similar structure to another chemical but differing slightly in composition (as in the replacement of one atom by an atom of a different element or the presence of a particular functional group). Analogs according to the invention share similar biologic functions.

In one embodiment, the modulator may be an agonist of the GPR78 polypeptide, an agonist of the GPR26 polypeptide, or an agonist of both the GPR78 polypeptide and the GPR26 polypeptide. In another embodiment, the modulator may be an antagonist of the GPR78 polypeptide, an antagonist of the GPR26 polypeptide, or an antagonist of both the GPR78 polypeptide and the GPR26 polypeptide Generally, the invention comprises methods for bringing together a GPR78 polypeptide or GPR26 polypeptide (including fragments and variants thereof), an appropriate ligand (or an analogue thereof), and a sample to be tested for the presence of a modulator of the GPR78 polypeptide or the GPR26 polypeptide. In one embodiment, the ligand is an isoflavone or an analog thereof. In one embodiment, the ligand is a phytoestrogen or an analog thereof. In another embodiment, the ligand is genistein or an analog thereof. In another embodiment, the ligand is daidzein or an analog thereof. In another embodiment, the ligand is biochanin A or an analog thereof. In another embodiment, the ligand is formononetin or an analog thereof.

In one embodiment, the GPR78 polypeptide or the GPR26 polypeptide (or a fragment of either one of these polypeptides) to be used in the screening methods is in soluble form. In another embodiment, the GPR78 polypeptide or the GPR26 polypeptide (or a fragment of either one of these polypeptides) to be used in the screening methods is substantially purified. In another embodiment, the GPR78 polypeptide or the GPR26 polypeptide to be used in the screening methods is: on the surface of a mammalian cell, on a cell membrane preparation, on a lipid vesicle, or immobilized to a solid surface.

As used herein, the term "substantially pure" or "substantially purified" refers to a polypeptide, nucleic acid or other material that is substantially free from other contaminating proteins, nucleic acids, and other biologicals derived from an original source organism or recombinant DNA expression system. Purity may be assayed by standard methods and will typically exceed at least about 50%, preferably at least about 75%, more preferably at least about 90%, and most preferably at least about 95% purity. Purity evaluation may be made on a mass or molar basis.

In one embodiment, the test sample comprises any agent. As used herein, an "agent" refers to any molecule including, for example, a polypeptide, an antibody or antigen binding fragment thereof, a nucleic acid (e.g., an antisense, ribozyme, siRNA or the like) or a small molecule. In one embodiment, the agent is selected from the group consisting of: a peptide, a polypeptide, an antibody or antigen-biding fragment thereof, a lipid, a carbohydrate, a nucleic acid, and a small organic molecule.

Preferably, the GPR78 polypeptide or fragment comprises the amino acid sequence of SEQ ID NO: 1 (GenBank Accession No. NP_543009) or a subsequence thereof; or in encoded by a polynucleotide comprising SEQ ID NO: 2 (GenBank Accession No. NM_08019) or a subsequence thereof.

Preferably, the GPR26 polypeptide or fragment thereof comprises the amino acid sequence of SEQ ID NO: 3 (GenBank Accession No. NP_703143) or a subsequence thereof; or in encoded by a polynucleotide comprising SEQ ID NO: 4 (GenBank Accession No. NM_153442) or a subsequence thereof.

Two basic types of screening systems can be used: binding assays or functional assays. Binding assays may involve the use of a labeled ligand. Ligands may be labeled using any known methods and any known labels.

Binding Assays

Typically for binding assays, a given amount of a GPR78 polypeptide or GPR26 polypeptide (or a fragment of either one of these polypeptides) is contacted with increasing amounts of a ligand, and the amount of the bound ligand is measured after removing unbound labeled ligand by washing. As the amount of the ligand is increased, a point is eventually reached at which all receptor binding sites are occupied or saturated. In a preferred embodiment, the ligand is labeled. When the ligand is labeled, specific receptor binding of the labeled ligand is abolished by a large excess of unlabeled ligand.

Preferably, an assay system is used in which non-specific binding of the labeled ligand to the receptor is minimal. Non-specific binding is typically less than 50%, preferably less than 15%, and more preferably less than 10% of the total binding of the labeled ligand.

In principle, a binding assay of the invention could be carried out using a soluble receptor of the invention, e.g., following production and refolding by standard methods from an *E. coli* expression system, and the resulting receptor-labeled ligand complex could be precipitated, e.g., using an antibody against the receptor. The precipitate could then be washed and the amount of the bound labeled ligand could be measured.

Preferably, however, a nucleic acid encoding a GPR78 polypeptide or GPR26 polypeptide is transfected into an appropriate host cell, whereby the receptor will become incorporated into the membrane of the cell. The transfected cell, or a membrane fraction thereof, can be used as a source of the receptor for assay. Preferably, specific binding of the labeled ligand to a membrane fraction from the untransfected host cell will be negligible.

The binding assays of this invention can be used to identify both GPR78 polypeptide and GPR26 polypeptide agonists and antagonists, because both agonists and antagonists of a receptor will compete for binding to the receptor with the ligand.

In the basic binding assay, the method for identifying a modulator of a GPR78 polypeptide or GPR26 polypeptide (either a modulator or antagonist) comprises: (a) contacting a GPR78 or GPR26 polypeptide or a fragment thereof with a ligand of the GPR78 or GPR26 polypeptide in the presence and absence of a test sample, under conditions permitting the binding of the ligand to the GPR78 or GPR26 polypeptide; and (b) measuring the amount of the ligand that is bound to the GPR78 or GPR26 polypeptide, wherein a modulator of the GPR78 or GPR26 polypeptide in the test sample is identified by measuring a change in binding of the ligand to the GPR78 or GPR26 polypeptide in the presence and absence of the test sample. In one embodiment, the ligand is labeled and the binding of the ligand to the GPR78 or GPR26 polypeptide is measured by detecting the label. The ligand may be labeled with any label, for example, the label may be a radioisotope, a fluorophore, a quencher of fluorescence, an enzyme, a dye, a luminophore, an affinity tag, or any other suitable label. In one embodiment, the ligand is an isoflavone or an analog thereof. In one embodiment, the ligand is a phytoestrogen or an analog thereof. In another embodiment, the ligand is genistein or an analog thereof. In another embodiment, the ligand is daidzein or an analog thereof. In another embodiment, the ligand is biochanin A or an analog thereof. In another embodiment, the ligand is formononetin or an analog thereof.

As used herein, the terms "change", "difference", "decrease" or "increase", as applied to e.g., binding, biological function or signaling activity, refer to at least 10% increase or decrease in binding or activity in a given assay.

The amount of ligand that is bound to the GPR78 polypeptide or the GPR26 polypeptide may be measured using any method known in the art. For example, binding or displacement of binding can be monitored by surface plasmon resonance, fluorescence resonance energy transfer (FRET), fluorescence polarization, biosensor assays, or any other method. In one embodiment, a decrease of at least 10% in the amount of the labeled ligand bound in the presence of the test sample indicates the presence of a modulator in the test sample. In another embodiment, a decrease of at least 20% in the amount of the labeled ligand bound in the presence of the test sample indicates the presence of a modulator in the test sample. In other embodiments, a decrease of at least 30% in the amount of the labeled ligand bound in the presence of the test sample indicates the presence of a modulator in the test sample.

Determination of whether a particular molecule inhibiting binding of the ligand to the receptor is an antagonist or a modulator can be determined in a second, functional assay.

Functional Assays

The invention comprises various functional assays for identifying modulators of a GPR78 polypeptide or a GPR26 polypeptide. Functional assays may also be used to determine whether an agent that binds the GPR78 or GPR26 polypeptide is an agonist or an antagonist of the GPR78 or GPR26 polypeptide.

In one embodiment, the invention comprises a method for identifying a modulator of a GPR78 or GPR26 polypeptide, comprising: (a) contacting a GPR78 or GPR26 polypeptide or a fragment thereof with a ligand of the GPR78 or GPR26 polypeptide in the presence and absence of a test sample; and (b) measuring the activity of the GPR78 or GPR26 polypeptide, wherein a modulator of the GPR78 or GPR26 polypeptide in the test sample is identified by measuring a change in the activity of the GPR78 or GPR26 polypeptide in the presence and absence of the test sample.

In another embodiment, the invention comprises a method for identifying a modulator of a GPR78 or GPR26 polypeptide, comprising: (a) contacting a GPR78 or GPR26 polypeptide or a fragment thereof with a test sample in the presence and absence of a ligand of the GPR78 or GPR26 polypeptide; and (b) measuring the activity of the GPR78 or GPR26 polypeptide, wherein a modulator of the GPR78 or GPR26 polypeptide in the test sample is identified by measuring a change in the activity of the GPR78 or GPR26 polypeptide in the presence and absence of the known ligand.

In another embodiment, the invention comprises a method for identifying a modulator of a GPR78 or GPR26 polypeptide, comprising: (a) contacting a GPR78 or GPR26 polypeptide or a fragment thereof with a test sample; and (b) measuring the activity of the GPR78 or GPR26 polypeptide, wherein a modulator of the GPR78 or GPR26 polypeptide in the test sample is identified by comparing the activity of the GPR78 or GPR26 polypeptide in the presence of the test sample to a standard value, wherein the standard value is based on the activity of the GPR78 or GPR26 polypeptide in the presence of a ligand of the GPR78 or GPR26 polypeptide.

In any of the above mentioned methods, an increase in the activity of the GPR78 or GPR26 polypeptide in the presence of the test sample indicates the presence of an agonist of the GPR78 or GPR26 polypeptide in the test sample. In one embodiment, a decrease of at least 10% in the activity of the GPR78 or GPR26 polypeptide in the presence of the test sample indicates the presence of an agonist in the test sample. In another embodiment, a decrease of at least 20% in the presence of the test sample indicates the presence of an agonist in the test sample. In other embodiments, a decrease of at least 30% in the presence of the test sample indicates the presence of an agonist in the test sample.

In any of the above mentioned methods, a decrease in the activity of the GPR78 or GPR26 polypeptide in the presence of the test sample indicates the presence of an antagonist of the GPR78 or GPR26 polypeptide in the test sample. In one embodiment, an increase of at least 10% in the activity of the GPR78 or GPR26 polypeptide in the presence of the test sample indicates the presence of an antagonist in the test sample. In another embodiment, an increase of at least 20% in the presence of the test sample indicates the presence of an antagonist in the test sample. In other embodiments, an increase of at least 30% in the presence of the test sample indicates the presence of an antagonist in the test sample.

In any of the above mentioned methods, the ligand of the GPR78 or GPR26 polypeptide may be an isoflavone or an analog thereof, or a phytoestrogen or an analog thereof. In another embodiment, the ligand is genistein or an analog thereof. In another embodiment, the ligand is daidzein or an analog thereof. In another embodiment, the ligand is biochanin A or an analog thereof. In another embodiment, the ligand is formononetin or an analog thereof.

Skilled workers are aware of a variety of approaches that could be used for measuring the activity of GPCR polypeptide. Any of these approaches could be used in the claimed methods.

For example, the activity of the GPR78 polypeptide or the GPR26 polypeptide may be measured by measuring any of the intracellular activities mediated by the GPR78 polypeptide or GPR26 polypeptide. Such parameters include but are not limited to intracellular second messenger pathways activated by the GPR78 polypeptide or GPR26 polypeptide, changes in cell growth rate, secretion of hormones, etc., using published methods.

In one embodiment, the activity of the GPR78 polypeptide or GPR26 polypeptide may be detected by measuring the signaling activity of the GPR78 or GPR26 polypeptide. The signaling activity of the GPR78 or GPR26 polypeptide may be measured by detecting a change in the level of a second messenger. As used herein, the term "second messenger" refers to a molecule, generated or caused to vary in concentration by the activation of a G-Protein Coupled Receptor (GPCR), that participates in the transduction of a signal from that GPCR. Non-limiting examples of second messengers include cAMP, diacylglycerol, inositol triphosphate, arachidonic acid release, inositol triphosphates and intracellular calcium. The term "change in the level of a second messenger" refers to an increase or decrease of at least 10% in the detected level of a given second messenger relative to the amount detected in an assay performed in the absence of a test sample.

Thus, for example, the activity of the GPR78 or GPR26 polypeptide may be detected by measuring: the effects of the ligands on receptor-mediated inhibition of forskolin-stimulated intracellular cAMP production (Parker et al., *Mol Brain Res*, 34:179-189 (1995)), receptor-stimulated Ca$^{++}$ mobilization and mitogenic effects (Sethi et al., *Cancer Res*. 51:1674-1679 (1991)), inositol phosphate production and mitogen activated protein kinase (MAP kinase) induction (Wang et al., *Biochemistry* 37:6711-17 (1998)) and receptor-mediated glucose-stimulated insulin release (Yanaihara et al., *Regulatory Peptides* 46:93-101 (1993)).

In one embodiment, the activity of the GPR78 or GPR26 polypeptide is measured by measuring a change in level of a cAMP. A change in the level of cAMP may be measured using any method known in the art. A number of kits for directly or indirectly measuring cAMP are commercially available. In one embodiment, the change in the level of cAMP is measured using a luciferase reporting system. In another embodiment, the change in the level of cAMP is measured using an adenylyl cyclase kit, such as the FlashPlate™ Adenylyl Cyclase kit from New England Nuclear (Cat. No. SMP004A).

Calcium mobilization in cells expressing the GPR78 polypeptide or the GPR26 polypeptide can be determined using a Fluorometric Imaging Plate Reader (FLIPR) assay, for example, as described in Zhang, et al., (2001) *J. of Biol. Chem.* 276(11):8608-8615. In general, the FLIPR assay includes the steps of: (a) contacting a cell (e.g., HEK293 cell or CHO cell) expressing the GPR78 polypeptide or the GPR26 polypeptide or a fragment thereof, in the presence of a known ligand with a test sample; and (b) measuring calcium mobilization by the cell. Calcium mobilization can be measured by exposing the cell to a calcium indicator such as Fluor-3-Am (Molecular Probes; Eugene, O R; 1-[2-Amino-5-(2,7-dichloro-6-hydroxy-3-oxy-9-xanthenyl) phenoxy]-2-(2'-amino-5'-methylphenoxy)ethane-N,N,N',N'-tetraacetic acid, pentaacetoxymethyl ester). In the presence of Ca$^{2+}$, the indicator fluoresces. The fluorescence can be detected by analyzing the cells, for example, with a fluorometric imaging plate reader. The sample can be identified as containing an antagonist by measuring substantially reduced calcium mobilization, compared to what would be measured in the absence of the sample and the sample can be identified as containing a modulator by measuring substantially increased calcium mobilization, compared to what would be measured in the absence of the sample. In one embodiment, the GPR78 or GPR26 polypeptide used in the calcium mobilization assay is a chimeric GPCR polypeptide.

In one embodiment, the activity of the GPR78 polypeptide or GPR26 polypeptide may be measured by measuring the binding of GTP by cell membranes containing receptors. The non-hydrolyzable GTP analog, [$^{35}$S]GTPγS, can be utilized to demonstrate enhanced binding of [$^{35}$S]GTPγS to membranes expressing activated receptors.

In another embodiment, the activity of the GPR78 or GPR26 polypeptide may be measured using a chimeric G protein. Exemplary methods are described in Kostenis et al., *Trends Pharmacol. Sci.* 26(11):595-602 (2005); New et al., *Assay Drug Dev. Technol.* 2( )3):269-80 (2004).

As mentioned above, a variety of approaches are available for measuring the activity of GPRC polypeptides. The methods recited herein are illustrative; those of ordinary skill in the art are credited with the ability to determine other suitable techniques.

Uses of Modulators of GPR78 and/or GPR26

In one embodiment, the invention comprises a method of modulating the activity of the GPR78 or GPR26 polypeptide comprising contacting a cell with a composition comprising a modulator of a GPR78 or GPR26 polypeptide.

In another embodiment, the invention comprises a method of modulating the activity of the GPR78 or GPR26 polypeptide comprising administering to a subject having or at risk of developing a GPR78- or GPR26-mediated disorder an effective amount of a composition comprising a modulator of a GPR78 or GPR26 polypeptide.

Modulators of GPR78 and/or GPR26 may be used to treat any GPR78- or GPR26-mediated disorders. In another embodiment, the invention comprises a method of treating a GPR78- or GPR26-mediated disorder, comprising administering to a subject in need thereof, an effective amount of composition comprising a modulator of a GPR78 or GPR26 polypeptide. As used herein, a "GPR78-mediated disorder" refers to any disease, disorder or condition that is dependent, mediated, regulated, or responsive, directly or indirectly, to the level of expression or activity of the GPR78 polypeptide. As used herein, a "GPR26-mediated disorder" refers to any disease, disorder or condition that is dependent, mediated, regulated, or responsive, directly or indirectly, to the level of expression or activity of the GPR26 polypeptide. As used herein, a "GPR78- or GPR26-mediated disorder" refers to either a GPR78-mediated disorder or a GPR26-mediated disorder.

Exemplary GPR78- or GPR26-mediated disorders include, without limitation, neurological disorders (such as anxiety disorders, including generalized anxiety disorders, obsessive-compulsive disorders (OCD), panic disorders, post-traumatic stress disorders (PTSD) and social phobias (also referred to as social anxiety disorders); bipolar affective disorder; schizophrenia; and Alzheimer's disease), cardiovascular disorders (such as coronary heart disease, arteriosclerosis, angina, high blood pressure, high cholesterol, heart attack, stroke and arrhythmia), hyperproliferative disorders (such as cancer, including, but not limited to, breast cancer and prostate cancer), metabolic disorders (such as obesity, diabetes, hypercholesterolemia, hyperlipidemia, dyslipidemia, hypertriglyceridemia, hyperglycemia, hypertension, insulin resistance and hyperinsulinemia), hormone-related conditions (such as menopause or pre-menopause, including any of the symptoms related to menopause or pre-menopause such as hot-flashes and bone loss), conditions resulting in bone loss (such as osteoporosis), diabetes, angiogenesis-related disorders, and urologic conditions.

As used herein, to "treat" refers to alleviating, preventing or delaying a particular disorder, disease or condition.

The term "subject" or "patient" refers to any organism, preferably an animal, more preferably a mammal (e.g., mouse, rat, rabbit, cow, dog, cat, cow, chimpanzee, gorilla) and most preferably a human.

In one embodiment, the modulator of GPR78 and/or GPR26 is an agonist of the GPR78 and/or GPR26 polypeptide. In one embodiment, the agonist of the GPR78 and/or GPR26 polypeptide is an isoflavone or an analog thereof, or a phytoestrogen or an analog thereto. In one embodiment, the agonist of the GPR78 and/or GPR26 polypeptide is genistein or an analog thereof. In one embodiment, the agonist of the GPR78 and/or GPR26 polypeptide is daidzein or an analog thereof. In one embodiment, the agonist of the GPR78 and/or GPR26 polypeptide is biochanin or an analog thereof. In one embodiment, the agonist of the GPR78 and/or GPR26 polypeptide is formononetin or an analog thereof. In another embodiment, the agonist of the GPR78 or GPR26 polypeptide is not isoflavone or an analog thereof. In another embodiment, the agonist of the GPR78 or GPR26 polypeptide is not genistein or an analog thereof. In one embodiment, the agonist of the GPR78 and/or GPR26 polypeptide is an antibody, or an antigen-binding fragment thereof, that binds to the receptor and triggers a response that mimics the action of the natural ligand on the receptor.

In another embodiment, the modulator of GPR78 and/or GPR26 is an antagonist of the GPR78 or GPR26 polypeptide. In one embodiment, the antagonist of the GPR78 and/or GPR26 polypeptide is diphenyleneiodonium Cl or an analog thereof. In one embodiment, the antagonist of the GPR78 and/or GPR26 polypeptide is sanguinarine Cl or an analog thereof. In one embodiment, the antagonist of the GPR78 polypeptide is an antibody, or antigen-binding fragment thereof, that binds to the GPR78 polypeptide and blocks or inhibits the response induced by the action of the natural ligand on the receptor. In another embodiment, the antagonist of the GPR78 polypeptide is an antisense molecule that acts on a nucleic acid encoding the GPR78 polypeptide. In one embodiment, the antagonist of the GPR26 polypeptide is an antibody, or antigen-binding fragment thereof, that binds to the GPR26 polypeptide and blocks or inhibits the response induced by the action of the natural ligand on the receptor. In another embodiment, the antagonist of the GPR26 polypeptide is an antisense molecule that acts on a nucleic acid encoding the GPR26 polypeptide.

In one embodiment, the invention provides a method to treat a neurological disorder comprising administering to a subject in need thereof a therapeutically effective amount of a composition comprising a modulator of the GPR78 or GPR26 polypeptide.

In one embodiment, the invention provides a method to treat an anxiety disorder comprising administering to a subject in need thereof a therapeutically effective amount of a composition comprising a modulator of the GPR78 or GPR26 polypeptide.

In one embodiment, the invention provides a method to treat a metabolic disorder comprising administering to a subject in need thereof a therapeutically effective amount of a composition comprising a modulator of the GPR78 or GPR26 polypeptide.

In one embodiment, the invention provides a method to treat a cardiovascular disorder comprising administering to a subject in need thereof a therapeutically effective amount of a composition comprising a modulator of the GPR78 or GPR26 polypeptide.

In one embodiment, the invention provides a method to treat a hyperproliferative disorder comprising administering to a subject in need thereof a therapeutically effective amount of a composition comprising a modulator of the GPR78 or GPR26 polypeptide.

In one embodiment, the invention provides a method to treat a hormone-related condition comprising administering to a subject in need thereof a therapeutically effective amount of a composition comprising a modulator of the GPR78 or GPR26 polypeptide.

In one embodiment, the invention provides a method to treat conditions resulting in bone loss comprising administering to a subject in need thereof a therapeutically effective amount of a composition comprising a modulator of the GPR78 or GPR26 polypeptide.

In one embodiment, the invention provides a method to treat diabetes comprising administering to a subject in need thereof a therapeutically effective amount of a composition comprising a modulator of the GPR78 or GPR26 polypeptide.

In one embodiment, the invention provides a method to decrease angiogenesis comprising administering to a subject in need thereof a therapeutically effective amount of a composition comprising a modulator of the GPR78 or GPR26 polypeptide.

Modulators of the GPR78 polypeptide and/or the GPR26 polypeptide may also be used to modulate angiogenesis. For example, disorders associated with increased angiogenesis (such as hyperproliferative disorders, diabetic blindness, age-related macular degeneration, rheumatoid arthritis and psoriasis) may be treated with an agonist of the GPR78 polypeptide or the GPR26 polypeptide. Similarly, disorders associated with decreased angiogenesis (such as stroke or delayed wound healing) may be treated with an agonist of the GPR78 polypeptide or the GPR26 polypeptide.

In one embodiment, the invention provides a method to treat a neurological disorder comprising administering to a subject in need thereof a therapeutically effective amount of a composition comprising: a phytoestrogen or an analog thereof, an isoflavone or an analog thereof, genistein or an analog thereof, daidzein or an analog thereof, biochanin A or an analog thereof, formononetin or an analog thereof. In a preferred embodiment, the invention provides a method to treat a neurological disorder comprising administering to a subject in need thereof a therapeutically effective amount of genistein, daidzein or analogs thereof.

In one embodiment, the invention provides a method to treat a schizophrenia comprising administering to a subject in need thereof a therapeutically effective amount of a composition comprising: a phytoestrogen or an analog thereof, an isoflavone or an analog thereof, genistein or an analog thereof, daidzein or an analog thereof, biochanin A or an analog thereof, formononetin or an analog thereof. In a preferred embodiment, the invention provides a method to treat a neurological disorder comprising administering to a subject in need thereof a therapeutically effective amount of genistein, daidzein or analogs thereof.

In one embodiment, the invention provides a method to treat a bipolar affective disorder comprising administering to a subject in need thereof a therapeutically effective amount of a composition comprising: a phytoestrogen or an analog thereof, an isoflavone or an analog thereof, genistein or an analog thereof, daidzein or an analog thereof, biochanin A or an analog thereof, formononetin or an analog thereof. In a preferred embodiment, the invention provides a method to treat a neurological disorder comprising administering to a subject in need thereof a therapeutically effective amount of genistein, daidzein or analogs thereof.

Agonists of the GPR78 polypeptide and/or the GPR26 polypeptide may also be used as antioxidants, to diminish blood leptin concentration and to improve memory.

Pharmaceutical Compositions

The modulators (agonists and antagonists) of the GPR78 polypeptide or GPR26 polypeptide, such as, for example, small organic molecules, peptides, inhibitory ligand analogs, agonistic or antagonistic antibodies or binding fragments thereof, as well as other types of agonists and antagonists, identified using the methods of the invention, may be used therapeutically to modulate the activity of the GPR78 polypeptide or GPR26 polypeptide, and thereby to treat any medical condition caused or mediated by the GPR78 polypeptide or GPR26 polypeptide.

The dosage regimen involved in therapeutic application will be determined by the attending physician, considering various factors which may modify the action of the modulator of the GPR78 polypeptide or GPR26 polypeptide, e.g., the condition, body weight, sex and diet of the patient, the severity of any infection, time of administration, and other clinical factors.

Although the compositions of this invention could be administered in simple solution, they are more typically used in combination with other materials such as carriers, preferably pharmaceutical carriers. Useful pharmaceutical carriers can be any compatible, non-toxic substance suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g. *Remington's Pharmaceutical Science*, 17th Ed. (Mack Publishing Company, Easton, Pa., 1990). Alternatively, compositions of the invention may be introduced into a patient's body by implantable drug delivery systems (Urquhart et al., *Ann. Rev. Pharmacol Toxicol.* 24:199 (1984)).

Therapeutic formulations may be administered in many conventional dosage formulation. Formulations typically comprise at least one active ingredient, together with one or more pharmaceutically acceptable carriers. Formulations may include those suitable for oral, rectal, nasal, or parenteral (including subcutaneous, intramuscular, intravenous and intradermal) administration.

The formulations may conveniently be presented in unit dosage form and may be prepared by any methods well known in the art of pharmacy. See, e.g., Gilman et al. (eds.) (1990), *The Pharmacological Bases of Therapeutics*, 8th Ed., Pergamon Press; and *Remington's Pharmaceutical Sciences*, supra, Easton, Pa.; Avis et al. (eds.) (1993) *Pharmaceutical Dosage Forms: Parenteral Medications* Dekker, N.Y.; Lieberman et al. (eds.) (1990) *Pharmaceutical Dosage Forms Tablets* Dekker, New York; and Lieberman et al. (eds.) (1990), *Pharmaceutical Dosage Forms Disperse Systems* Dekker, N.Y.

For therapeutic use, the antibodies to the GPR78 polypeptide or GPR26 polypeptide (or fragments of said antibodies) are preferably chimeric or humanized to reduce antigenicity and human anti-mouse antibody (HAMA) reactions. The methodology involved is disclosed, e.g., in U.S. Pat. No. 4,816,397 to Boss et al. and in U.S. Pat. No. 4,816,567 to Cabilly et al. Further refinements on antibody humanization are described in European Patent 451 216 B1.

Typical protocols for the therapeutic administration of antibodies are well known in the art and have been disclosed, e.g., by Elliott et al., *The Lancet* 344:1125 (1994); Isaacs et al., *The Lancet* 340:748 (1992); Anasetti et al., *Transplantation* 54:844 (1992); Anasetti et al., *Blood* 84:1320 (1994); Hale et al., *The Lancet* 2:1394 (1988); Queen, *Scrip* 1881:18 (1993); and Mathieson et al., *N. Eng. J. Med.* 323:250 (1990).

Often, treatment dosages are titrated upward from a low level to optimize safety and efficacy. For example, daily antibody dosages will fall within a range of about 0.01 to 20 mg protein per kilogram of body weight. Typically, the dosage range will be from about 0.1 to 5 mg protein per kilogram of body weight.

Dosages of antigen binding fragments from the antibodies will be adjusted to account for the smaller molecular sizes and possibly decreased half-lives (clearance times) following administration. Various modifications or derivatives of the antibodies or fragments, such as addition of polyethylene glycol chains (PEGylation), may be made to influence their pharmacokinetic and/or pharmacodynamic properties.

Knockout Animals

The present invention further encompasses knockout animals that express less or no functional GPR26 receptor ("GPR26 knockouts") as a result of one or more loss-of-function mutations. In particular, the present invention comprises a GPR26 knockout mouse that exhibits reduced anxiety and/or reduced metabolic activity. In one embodiment, one of the alleles of the endogenous GPR26 gene has been inactivated. In another embodiment, both alleles of the endogenous GPR26 gene have been inactivated. These animals are said to have a disrupted endogenous GPR26 gene. Preferably, such an animal expresses no GPR26 polypeptide. A non-human animal that does not express any functional GPR26 polypeptide is often referred to as having a "null" mutation.

Preferably, the knockout animal is a non-human mammal, such as a pig, a sheep or a rodent. Most preferably, the knockout animal is a mouse or a rat.

The GPR26 knockout mouse may exhibit reduced anxiety as demonstrated by one or more anxiety measurement assays, e.g., an Elevated Plus Maze Test, an Open Field Test, a Novel Environment-Induced Feeding Suppression Assay, a Tail Suspension Test, or a Comprehensive Cage Monitoring System, as described in Examples 13-16 and 23 below.

The GPR26 knockout mouse may exhibit reduced metabolic activity as demonstrated by one or more metabolism measurement assays, e.g., a Comprehensive Cage Monitoring System, as described in Example 23 below.

The present invention also provides for descendants of the GPR26 knockout mouse, which may be obtained by breeding with animals of the same or another genotype. Primary cell cultures, secondary cell lines, tissue explants, cultures of tissue explants, organ explants, cultures of organ explants, tissue extracts, and cell extracts derived from the GPR26 knockout mouse are also within the scope of the present invention.

Methods of Producing Knockout Animals

Methods for generating a non-human knockout animal are well known in the art, and any suitable method may be used.

In one embodiment, the GPR26 knockout mouse of the present invention is produced by the introduction of a knockout construct into murine embryonic stem (ES) cells. At least a portion of the GPR26 gene in the ES cell is replaced by, e.g., homologous recombination with the knockout construct, which comprises at least a portion of one exon of the GPR26 coding sequence.

ES cells are grown on an appropriate fibroblast-feeder layer or grown in the presence of appropriate growth factors, such as leukemia inhibiting factor (LIF). Knockout constructs can be efficiently introduced into the ES cells by DNA transfection using a variety of methods known to the art, including electroporation, calcium phosphate co-precipitation, protoplast or spheroplast fusion, lipofection and DEAE-dextran-mediated transfection. Knockout constructs may also be introduced into ES cells by retrovirus-mediated transduction or by micro-injection. Cells containing the knockout construct may be detected by employing a selective medium. After sufficient time for the colonies to grow, they are picked and analyzed for the occurrence of homologous recombination or integration of the knockout construct using, e.g., Southern blot or PCR.

Those colonies that are positive may then be used for embryo manipulation and blastocyst injection. Blastocysts are obtained from four- to six-week-old superovulated females. The ES cells are trypsinized, and the modified cells are injected into the blastocoel of the blastocyst. After injection, the blastocysts are returned to each uterine horn of pseudopregnant females. Females are then allowed to go to term, and the resulting litters are screened for cells that have incorporated the knockout construct. For a review, see Jaenisch, R., *Science* 240:1468-1474 (1988).

By providing for a different phenotype of the blastocyst and the ES cells, chimeric progeny that carry the GPR26 gene disruption can be readily detected. The chimeric animals are screened for the presence of the knockout construct. Chimeric animals that carry the GPR26 gene disruption (normally chimeric males) are mated with wildtype animals to produce heterozygotes, and the heterozygotes are mated to produce homozygotes for the GPR26 gene disruption if desired.

In another embodiment, the GPR26 knockout mouse of the invention is produced by introducing knockout constructs into the germline of the mouse. One or several copies of the knockout construct may be incorporated into the genome. Embryonal target cells at various developmental stages can be used to introduce knockout constructs. Different methods are used depending on the stage of development of the embryonal target cell. Introduction of the knockout construct into the embryo can be accomplished by any means known in the art such as, for example, microinjection, electroporation, or lipofection. Following introduction of the knockout construct into the fertilized egg, the egg may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes.

The number of copies of the knockout constructs that are added to the zygote is dependent upon the total amount of exogenous genetic material added and will be the amount that enables the genetic transformation to occur. Theoretically only one copy is required; however, generally, numerous copies are utilized, for example, 1,000-20,000 copies of the knockout construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of offspring the species naturally produces.

Knockout offspring of the surrogate host may be screened for the presence and/or expression of the knockout construct by any suitable method. Screening is often accomplished by Southern blot or Northern blot analysis, using a probe that is complementary to at least a portion of the knockout construct. Western blot analysis using an antibody against a protein encoded by the knockout construct may be employed as an alternative or additional method for screening for the presence of the knockout construct product. Alternative or additional methods for evaluating the presence of the knockout construct include, without limitation, suitable biochemical assays such as enzyme and/or immunological assays, histological stains for particular marker or enzyme activities, flow cytometric analysis, and the like. Analysis of the blood may also be useful to detect the presence of the knockout construct product in the blood, as well as to evaluate the effect of the knockout construct on the levels of various types of blood cells and other blood constituents.

Progeny of the knockout animals may be obtained by mating the knockout animal with a suitable partner, or by in vitro fertilization of eggs and/or sperm obtained from the knockout animal. Where mating with a partner is to be performed, the partner may or may not be a knockout. Alternatively, the partner may be a parental line. Where in vitro fertilization is used, the fertilized embryo may be implanted into a surrogate host, or incubated in vitro, or both. Using either method, the progeny may be evaluated for the presence of the knockout construct using methods described above, or other appropriate methods.

Uses of Knockout Animals

The GPR26 knockout mice of this invention will have a variety of uses. The different uses of the GPR26 knockout mice according to the invention include not only the whole animal per se, but also parts of the animal for use in vitro, such as a cell, tissue, organ and bone.

The GPR26 knockout mouse of the present invention has utility as a model for the development of therapies for anxiety disorders or metabolic disorders. Because the GPR26 knockout mouse exhibits reduced anxiety and reduced metabolism, this knockout provides a setting to investigate related disorders.

The GPR26 knockout mouse of the present invention may be used to screen an agent for activity in stimulating, preventing, inhibiting, alleviating or reversing activity in different diseases or disorders. Such an agent may be a chemical compound, a drug, or a pharmaceutical compound. It may also be nucleic acid, such as DNA, RNA, a protein or fragments thereof; an antibody or fragments thereof; a peptide, such as a polypeptide or oligopeptide; or a mixture thereof. Also, the agent may be an agent or a mixture of agents retrieved as a natural extract from the vegetable kingdom, or the animal kingdom.

Screening for useful drugs or agents would involve administering the candidate drug or agent over a range of doses to the GPR26 knockout animal and assaying at various time points for a modulating effect(s) of the drug on the disorder being evaluated. A knockout animal of the present invention could be used to screen a variety of agents, either alone or in combination, to determine, e.g., whether partial or total restoration or activation of a certain activity will occur. Screening methods involving GPR26 knockout animals are of particular use for determining the specificity and action of potential therapies for anxiety disorders or metabolic disorders.

Test agents could also be evaluated in vitro. For instance, primary cultures or cell lines could be established in vitro from GPR26 knockout animals using standard protocols. Test compounds could be administered to the cultured cells in various doses and the effects evaluated.

In one embodiment, a GPR26 knockout mouse and its progeny according to the invention may be used to screen an agent for activity in preventing, inhibiting, alleviating or reversing activity in an anxiety disorder.

Thus, the present invention provides methods for screening agents for anxiolytic or anxiety-inducing activity, and particularly for GPR26 anxiolytic or anxiety-inducing activity. In these screening methods of the present invention, a test anxiolytic or anxiety-inducing agent is administered to an animal model of reduced anxiety, and the effect of the test compound on the animal model is determined and related to the anxiolytic or anxiety-inducing properties of the test agent. A feature of the subject invention is that the reduced anxiety animal model is generally a GPR26 knockout mouse.

In a preferred embodiment of these screening methods, the candidate agent is administered to the animal model, and the animal model is then subjected to one or more anxiety measurement assays, e.g., an Elevated Plus Maze Test, an Open Field Test, a Novel Environment-Induced Feeding Suppression Assay, a Tail Suspension Test, or a Comprehensive Cage Monitoring System, as described in Examples 13-16 and 23 below. Aspects of the anxiety-like behavior of the animal model in the assays are then determined and related to the anxiolytic or anxiety-inducing activity of the test agent, e.g., through comparison with a control. In some embodiments, the control is a second GPR26 knockout mouse that has not been administered the test agent.

In another embodiment, a GPR26 knockout mouse and its progeny according to the invention may be used to screen an agent for activity in preventing, inhibiting, alleviating or reversing activity in a metabolic disorder.

Thus, the present invention provides methods for screening agents for metabolic activity, and particularly for GPR26 metabolic activity. In these screening methods of the present invention, a test metabolic agent is administered to an animal model of reduced metabolism, and the effect of the test compound on the animal model is determined and related to the metabolic properties of the test agent. A feature of the subject invention is that the reduced metabolism animal model is generally a GPR26 knockout mouse.

In a preferred embodiment of these screening methods, the candidate agent is administered to the animal model, and the animal model is then subjected to one or more metabolism measurement assays, e.g., a Comprehensive Cage Monitoring System, as described in Example 23 below. For example, changes in indicators of metabolic rate, such as oxygen levels, carbon dioxide levels, heat production and blood levels of thyroxine can be evaluated. Body weight pre- and post-treatment may also be assessed. Aspects of the metabolism of the animal model in the assays are then determined and related to the metabolic activity of the test agent, e.g., through comparison with a control. In some embodiments, the control is a second GPR26 knockout mouse that has not been administered the test agent.

The GPR26 knockout mouse of the present invention may also be used as a model for GPR26 receptor function. For example, the GPR26 knockout mice of the invention may be utilized to evaluate specific modulators of GPR26 pathways, e.g., for a stimulatory or inhibitory effect. Test compounds, e.g., from compound libraries, can be applied to the animals and the effect of the compounds evaluated, e.g., by comparison with placebo-treated animals.

Diagnostic Methods

GPR26 is implicated in metabolic disorders. Therefore, detecting the presence and/or activity of GPR26 in an individual, or preferably in a sample isolated from an individual, allows a diagnosis to be made on the presence of or susceptibility to metabolic disorders, as will be appreciated by one skilled in the art. In a preferred embodiment, the diagnosis is performed in vitro, i.e. it is not performed on the body of a person or animal that is being diagnosed.

Thus, the present invention provides a method of determining whether an individual (e.g., a patient) is susceptible to a metabolic disorder, comprising the steps of (a) determining the expression level of a GPR26 polypeptide in a sample isolated from the individual, and (b) determining, compared to a control, whether the individual from which the sample was isolated has or is susceptible to a metabolic disorder.

The present invention, also provides a method of determining whether an individual is susceptible to a metabolic disorder, comprising the steps of (a) determining the level of biological activity of a GPR26 polypeptide in a sample isolated from the individual, and (b) determining, compared to a control, whether the individual from which the sample was isolated has or is susceptible to a metabolic disorder.

The sample may comprise a cell or tissue sample from an organism suffering or suspected to be suffering from a disorder associated with increased, reduced or otherwise abnormal GPR26 expression, including spatial or temporal changes in level or pattern of expression. The expression level of a GPR26 polypeptide in the sample may be determined by, e.g., measuring levels of GPR26 polypeptide or GPR26 mRNA. The level or pattern of expression of GPR26 polypeptide in an organism suffering from or suspected to be suffering from such a disorder may be usefully compared with the level or pattern of expression in a normal organism as a means of diagnosis of disease.

The presence of a nucleic acid comprising a GPR26 nucleic acid in a sample may be determined by contacting the sample with at least one nucleic acid probe specific for said nucleic acid and monitoring said sample for the presence of the nucleic acid. The nucleic acid probe may specifically bind to the GPR26 nucleic acid, or a portion of it, and any binding between the two detected; the presence of the complex itself may also be detected. The presence of a GPR26 polypeptide in a sample may be determined by contacting the sample with an antibody capable of binding the polypeptide and monitoring the sample for the presence of the polypeptide. This may conveniently be achieved by monitoring the presence of a complex formed between the antibody and the polypeptide, or by monitoring the binding between the polypeptide and the antibody. Methods of detecting binding between two entities are known in the art, and include FRET (fluorescence resonance energy transfer), surface plasmon resonance, etc.

Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as a GPR26 polypeptide, in a sample derived from a host are well-known to those of skill in the art. Such assay methods include radioimmunoassays, competitive-binding assays, Western Blot analysis and ELISA assays.

The present invention further provides a kit for diagnosis of susceptibility to a GPR26-associated metabolic disorder comprising one or more of: a GPR26 polypeptide or a fragment thereof, an antibody against such a polypeptide or fragment (or fragment of it), a GPR26 polynucleotide or a fragment thereof, and a complementary nucleotide sequence.

Individuals identified as susceptible to a GPR26-associated disorder according to the methods provided above can be treated to prevent the occurrence of the disorder. Similarly, individuals so identified can be treated in the early stages of a GPR26-associated disorder to prevent the further occurrence or development of the disorder.

Example 1

Cloning, Expression and Functional Analysis of the GPR78 and GPR26 Polypeptides

Molecular Cloning

Full length open reading frames (ORFS) of GPR78 and GPR26 were obtained with PCR. Specific sense and antisense oligonucleotide primers were synthesized to cover the initiating ATG and the stop codons. Primers for GPR78 were J606 (GCC GCC ACC ATG GGC CCC GGC GAG GCG CTG CTG (SEQ ID NO: 5)) and J607 (TCA GTG TGT CTG CTG CAG GCA GGA (SEQ ID NO: 6)). Primers for GPR26 were J686 (GCC GCC ACC ATG AAC TCG TGG GAC GCG GGC CT (SEQ ID NO: 7)) and J687 (CCT TCA AGA CAC CGG CAG AAT (SEQ ID NO: 8)). PCR was run to amplify by using Marathon-Ready™ cDNA obtained from Clontech as template. The PCR conditions were: 95° C., 3 min; 35 cycles of 95° C., 30 s, 62° C., 30 s, 68° C., 2 min; and 68° C., 7 min. The resulting PCR products of 1023 bp and 1011 bp respectively were gel-purified using a gel extraction kit from QIAGEN, and cloned into a PCR3.1 vector (from Invitrogen) to form two expression constructs designated PCR3.1-GPR78 and PCR3.1-GPR26.

Expression Analysis

The expression patterns of GPR78 and GPR26 mRNA in human tissues were analyzed with using TAQMAN® detection as described previously ([21]).

HEK293/Cre-Luc Cell Line and Cell Culture

HEK293 cells (Invitrogen "H" strain) were co-transfected with the cAMP-responsive luciferase reporter plasmid pCREluc from Stratagene (La Jolla, Calif.; Catalog No. 219075-51) and plasmid harboring the hygromycin resistance gene, pTKhyg, from Clontech. Briefly, transfection was carried out by suspending 20×10⁶ HEK293 cells/mL of complete medium DMEM, 10% FBS, non-essential amino acids, penicillin-streptomycin-glutamine. In 0.4 mL of cell suspension, 4 µg of each plasmid were electroporated at 500 µF and 0.2 kV in a 4 mm electroporation cuvette using the GenePulser instrument from Bio-Rad (Hercules, Calif.). Transfected cells were plated at approximately 1000 cells/10 cm dish in 10 mL complete medium and incubated at 37° C., 5% $CO_2$. After 48 hours, the medium was replaced with fresh medium containing 200 µg/mL hygromycin. Cell colonies resisting hygromycin were picked and expanded for screening for luciferase activity. Colonized cells were plated into 96-well plates at 50,000 cells/100 µL medium/well using 8-well replicates per cell line. After overnight incubation at 37° C., 5% $CO_2$, additions of forskolin at final concentrations of 0, 1, 5 and 10 µM in duplicate were done in the presence of 10 µM 4-(3-butoxy-4-methoxy-benzyl) imidazolidin-2-one (Sigma B-8279, RO20-1724). After 6 hours of incubation at 37° C., 5% $CO_2$, 100 µL of Bright-Glo™ obtained from Promega (Madison, Wis.) was added. Luciferase activity was measured in relative light units (RLU) using a luminometer (Luminoskan Ascent®, Thermo-Electron Corp.) at 100 ms exposure per well. CREluc cell line #8 had highest fold activation of firefly luciferase and was used in the studies (referred to as HEK293/cre-luc).

HEK293-cre-luc stable cell line was grown in Dulbecco's modified eagle medium supplemented with 10% FSB, 10 mM MEM non essential amino acid solution, 100 U/ml penicillin, 0.1 mg/ml streptomycin and 100 µg/ml hygromycin B and incubated at 37° C. in a 5% $CO_2$-95% air environment. 100 µg/ml hygromycin B was included in HEK293/cre-luc cell medium for maintenance of CRE luciferase in stable cell line.

Transient Transfection

HEK293/cre-luc cells were harvested by 0.05% trypsin EDTA buffer, cells re-suspended in complete culture medium 20 million in 0.4 µl transfection cuvette, 1 microgram receptor plasmid was transfected into reporter cells by electroporation method. The parameter of the GenePulser (Bio-Rad Laboratories, Hercules, Calif.) was set at: voltage 200 volts and capacity 500 microfarads. After electroporation, cells were re-suspended at a density of 25,000 cells in 25 µl complete medium, placed in 384-well plate. After 24 hours of transfection, the transfection medium was replaced with fresh complete medium. Empty plasmid vector was transfected as a negative control (mock transfection).

Cre Luciferase cAMP Assay

Forty hours after transfection, cells were stimulated by adding 5 µl of ligand in 60 µM 4-(3-butoxy-4-methoxy-benzyl)-2-Imidazolidinone in 293 SFM II serum-free media obtained from Gibco (Gaithersburg, Md.), and incubated for 6 hours at 37° C. in a 5% $CO_2$-95% air incubator. When inhibitors were used in the assay, they were added 30 minutes before cell stimulation. At the end of incubation, 25 µl of Bright-Glo™ obtained from Promega (Madison, Wis.) was added into each well. Luciferase activity was determined with a luminometer (Luminoskan Ascent®, Thermo-Electron Corp.), at a speed of 100 milliseconds per well.

Stable Transfection of GPR78 and GPR26

Constructs PCR3.1-GPR78 and PCR3.1-GPR26 were transfected into HEK293/cre-luc cells with use of Lipofectamine™ 2000 and cells were selected for G418 resistance. Cells resistant to G418 were further diluted and selected for individual colonies. Cell lines grown from the G418-resistant colonies were screened for positive response with genistein in the Cre-Luciferase cAMP assay.

cAMP Measurements

Intracellular cAMP was measured directly with a cAMP kit purchased from Meso Scale Discovery (Gaithersburg, Md., Ma6000 cAMP 384-well Kit, Catalog number K210FDD-2). The assay was preformed by following the manufacturer's protocol. Briefly, stable HEK293/cre-luc cells expressing GPR78 or GPR26 were harvested, washed with PBS and resuspended at 300,000/10 µl of assay buffer (from the kit) containing 0.5 mM IBMX. Genistein at appropriate concentrations was diluted in the cAMP assay buffer and 5 µl was added into wells of the assay plate. The mixture was then incubated at room temperature for 30 minutes. Light intensity in assay wells was measured using a MSD SI6000 instrument obtained from Meso Scale Discovery.

Reagents and Materials

The NIH 3T3 cell line was obtained from the ATCC. Culture media and supplements were from Gibco (Gaithersburg, Md.); Bright-Glo™ luciferase assay system was obtained from Promega (Madison, Wis.); Cyclic AMP assay kits were purchased from Meso Scale Discovery; forskolin, genistein, SQ22536, MDL-1233a, H89 were from Sigma-Aldrich Chemical Co (St. Louis, Mo.); 4-(3-butoxy-4-methoxy benzyl)-2-imidazolidinone was from ICN Biomedical Inc. (Aurora, Ohio). The Library of Pharmacologically Active Compounds (LOPAC) collection was obtained from Sigma.

Example 2

Activation of GPR78 by Isoflavones

To find ligands for GPR78, a number of molecules including the RBI LOPAC collection that contains a total of 640 compounds in eight 96-well plates were screened. The RBI LOPAC collection is a collection of molecules of known receptor agonists and antagonists, enzyme inhibitors, and signal transduction agents.

Response of cells with the expressed receptor to test ligand stimulation was subject to two types of detection: intracellular cAMP accumulation and intracellular Ca2+ flux monitored with fluorescent intensity using a Fluorimetric Image Plate Reader (FLIPR). For cAMP measurement, a HEK293 cell line that had been stably transfected with luciferase reporter gene, was used as a host cell transiently transfected with the pCR3.1-GPR78 construct described in Example 1.

In this screening, it was found that 25 µM of genistein significantly stimulated cAMP production, showing an increased luciferase activity, as compared to the mock transfection control (more than 8-fold increase, FIG. 1). Forskolin, at 10 µM as a positive control, stimulated cellular cAMP at comparable levels between cells that expressed GPR78 and did not express GPR78 (FIG. 1). Ten µM of forskolin was used because forskolin stimulated luciferase signal in a concentration range between 0 and 10 µM in a linear fashion. Cyclic AMP level stimulated with use of 10 µM of forskolin was used as a reference as maximum forskolin-stimulated cAMP production in each experiment.

Genistein is known to inhibit protein tyrosine kinase with IC50 at 1-22 µM, depending on the substrates used ([12]; [22]). To test if the increased cAMP production was caused by the protein tyrosine kinase (PTK)-inhibiting activity of genistein, two other PTK inhibitors were examined and compared with genistein. PTK inhibitors Tyrphostin B42 and Tyrphostin A9 at 23 µM and 24 µM respectively, stimulated cAMP at a level not higher than the level in GPR78-expressing cells stimulated with buffer ("Basal" level in FIG. 1). The IC50's of these two compounds at inhibiting PTK were 20 µM ([23]) and 0.04-9 µM ([24]), respectively, and are comparable or well below the concentrations used in the experiment. Cells transfected with GPR78 cDNA had a higher cAMP level than the mock cells when stimulated with only buffer (FIG. 1); this data suggests existence of a constitutive activity of the receptor.

Figure 2A:
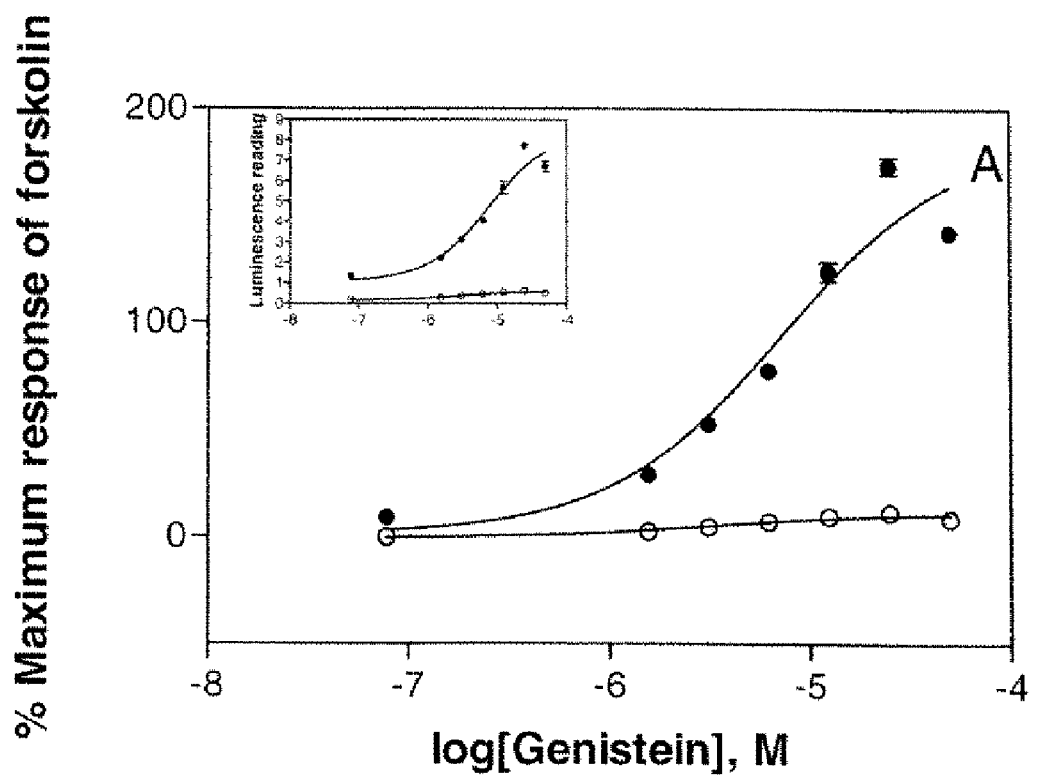
FIG. 2. Dose response curve of genistein stimulation of intracellular cAMP accumulations on transiently transfected GPR78 (●) and vector control (○) HEK/cre-luc cells. (A) Luciferase cAMP assay for genistein stimulation. Data is expressed as percentage of maximum response of the forskolin at 10 μM, and un-normalized luminescence readings are shown in inset. (B) Forskolin control in luciferase cAMP assay, and luminescence reading value in small figure inset. (C) cAMP quantitative assay measured by a direct cAMP assay (the Meso-Scale Discovery Kit from Meso-Scale Discovery (Gaithersburg, Md.)). Data are expressed as percentage of maximum response of 10 μM forskolin. (10 μM forskolin stimulated 194 nM cAMP with 20,000 cells and used as 100% stimulation). Data is mean±SD. n=3.
Figure 2B:
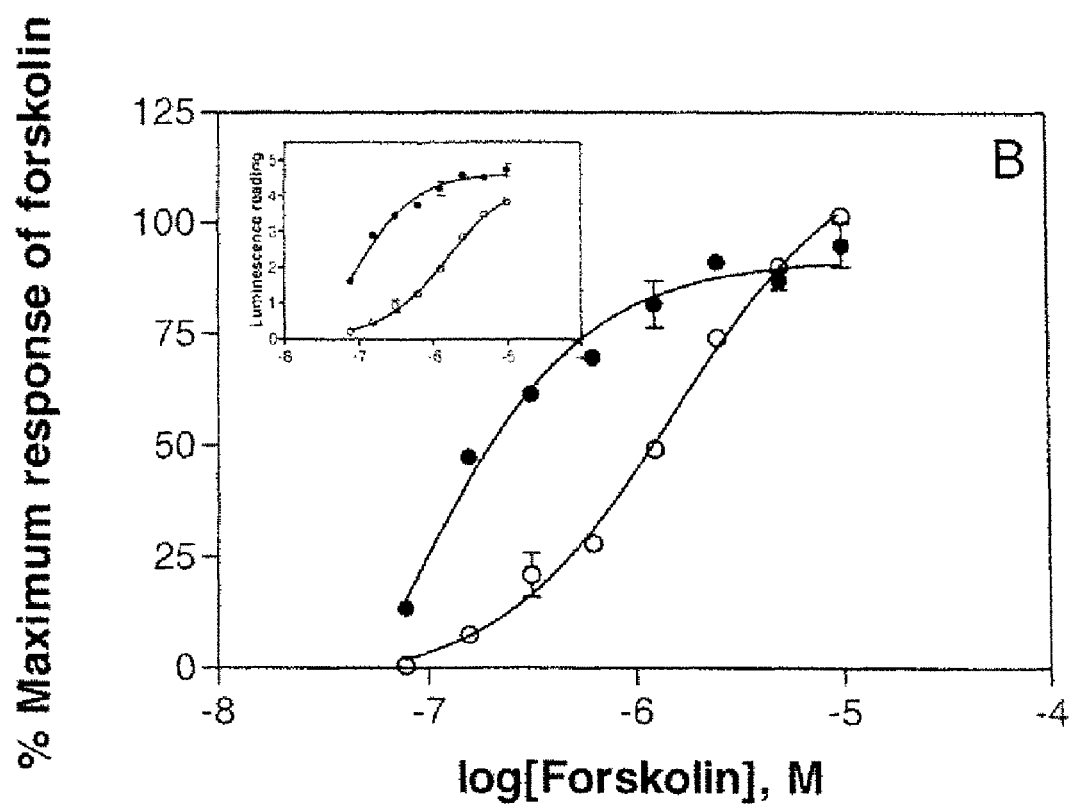
Figure 2C:
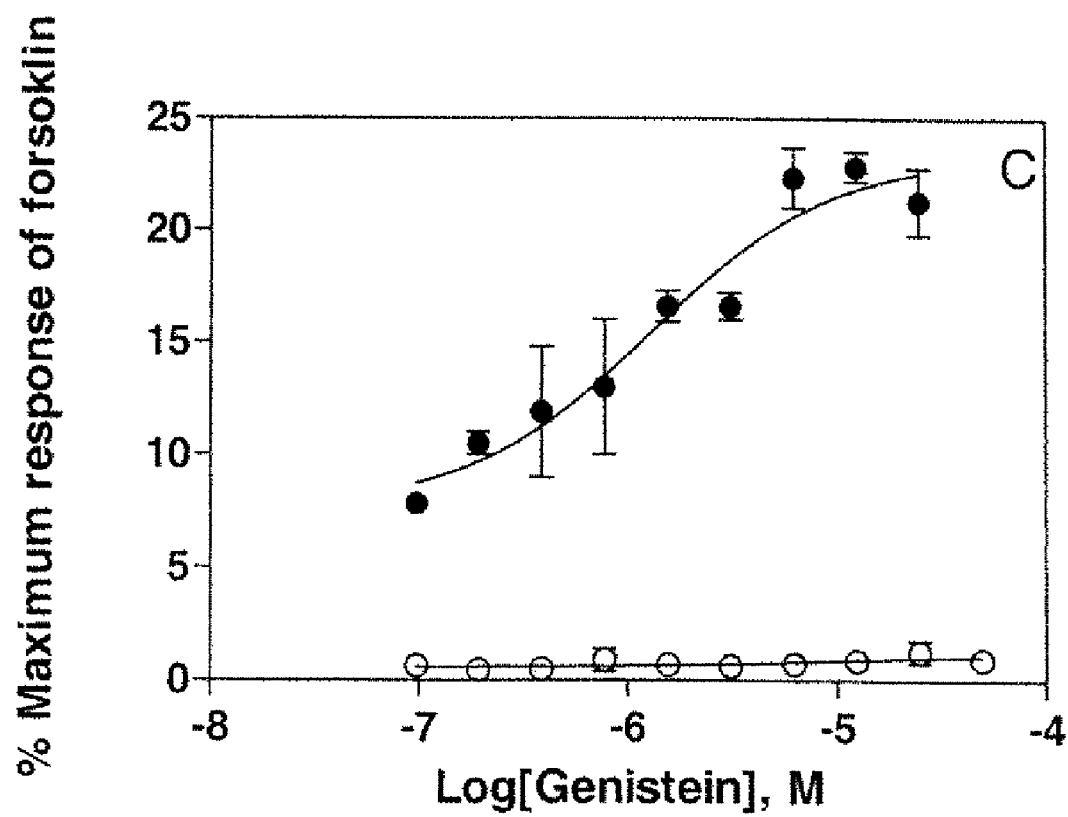

The potency of genistein in induction of cAMP in GPR78 expressing-293HEK/cre-luc cells ($EC_{50}$=7 µM in FIG. 2A) was determined. Multiple independent measurements yielded an EC50 range of 6 to 10 µM, n=6. Again, only GPR78-cells responded to genistein stimulation while mock transected cells showed much lower cAMP response when incubated with genistein (FIG. 2A). Forskolin as control elevated cAMP levels in both GPR78-cells and mock-cells (FIG. 2B), but that for GPR78-cells was higher than control cell expressing no GPR78 at each forskolin concentration except in higher concentration region where effect of forskolin was saturated (FIG. 2B), indicating the existence of constitutive activity of GPR78. To directly measure the cAMP concentration in the cells, HEK293/cre-luc cells stably transfected with GPR78 cDNA were incubated with genistein and cAMP was measured. Again, there was an elevated level of cAMP in the cells at lower concentration of genistein; further increase genistein concentration resulted in a dose response increase of cAMP level with an EC50 of ~6 µM (FIG. 2C). This data is consistent with a GPR78-expression-mediated constitutive activity and receptor activation at higher genistein concentration.

Another GPCR, GPR30, has been found to respond to estrogen as well as genistein activation through a c-fos pathway in MCF-7, MAD-MB-231 and SKBR3 breast cancer cells ([25]). Since GPR78 is activated by genistein, a test was conducted to determine if GPR78 was also activated by estrogen. 17β-estradiol, progesterone, testosterone were incubated with HEK293/cre-luc/GPR78 cells and cAMP measurements were performed by luciferase reporter assay as well as direct cAMP measurement using a cAMP assay kit obtained from Perkin-Elmer (Catalog No. 6760625). All compounds were dissolved in 50% DMSO at 10 mM, diluted to 15% DMSO, and added into cells medium at a further dilution factor of 10. The compounds were in 1.5% DMSO at final concentration 300 µM. No cAMP stimulation was observed with estrogen and other steroids. In addition, 17β-estradiol in water soluble form (Sigma, catalog number E4389) was tested with HEK293/cre-luc/GPR78 cells and no increase cAMP was observed.

Figure 3:
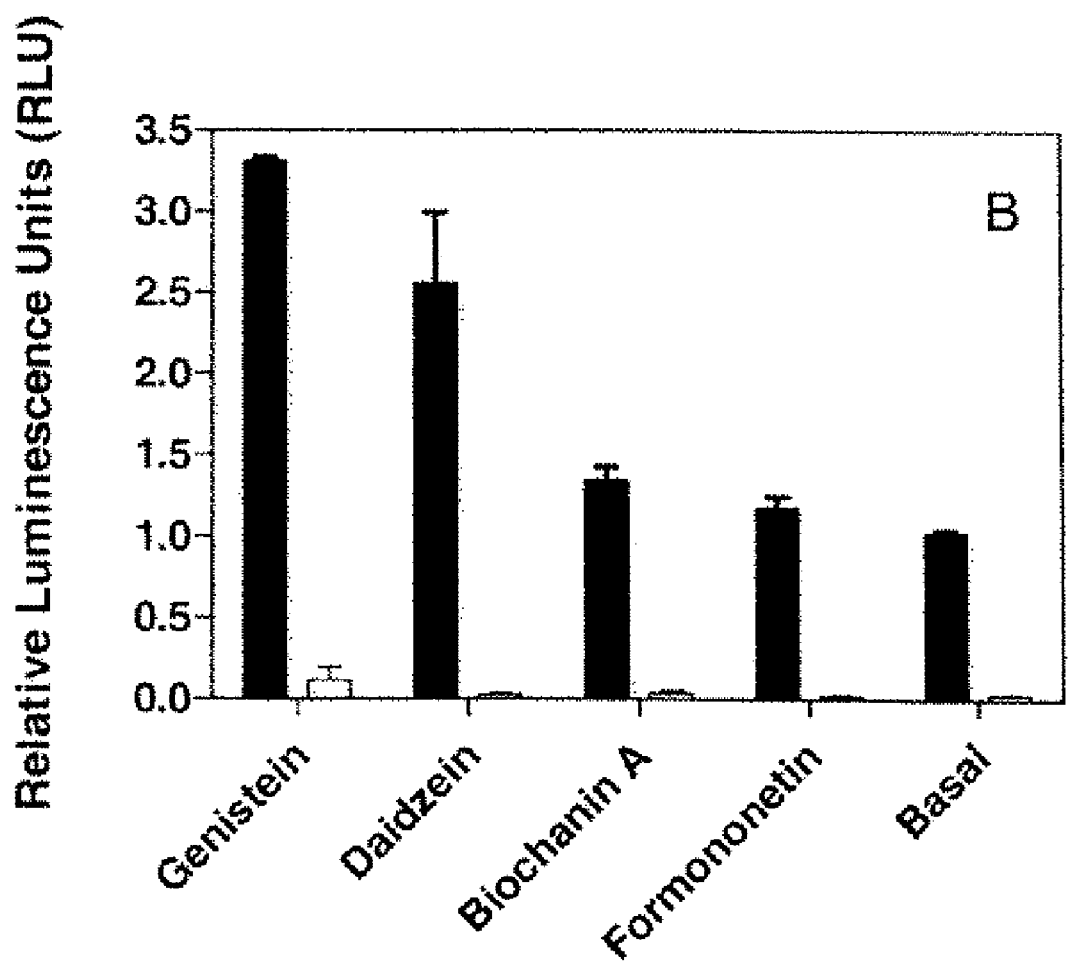
FIG. 3. Ligand specificity of genistein activation of GPR78. Cellular cAMP production was measured in cells expressing GPR78 stimulated with genistein, daidzein, biochanin or formononetin. GPR78 transfected- (filled bars) and vector control (empty bars) HEK293/cre-luc cells are shown.

A group of isoflavones isolated from soybean with structural similarity to genistein was also tested. Daidzein significantly increased cAMP level comparable to that by genistein (FIG. 3). Biochanin A and formononetin only slightly induced cAMP levels as compared to the buffer control in this experiment. However, it is likely that biochanin A and formononetin may show higher activity at other concentrations or under different assay conditions (FIG. 3).

Example 3

Constitutive Activity of GPR78

Figure 4:
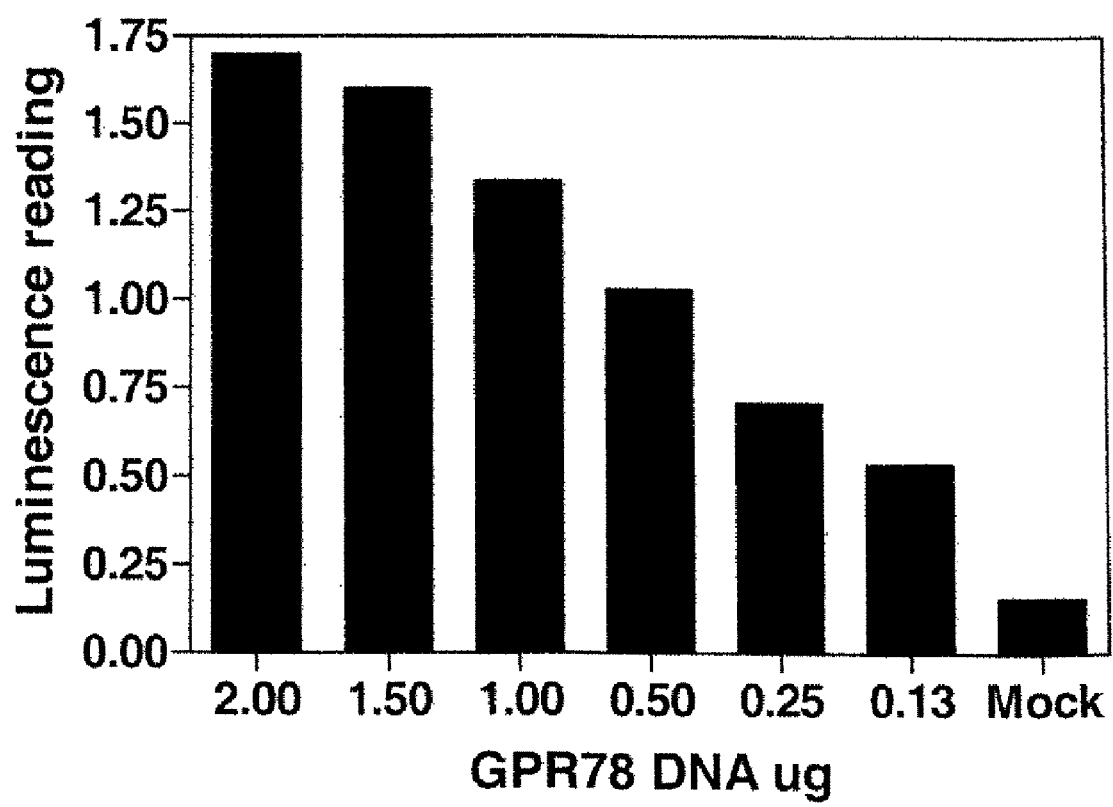
FIG. 4. Basal level of cAMP production in cells expressing GPR78 is GPR78-dose dependent. Various amounts of GPR78 cDNA were transiently transfected in HEK293/cre-luc cells and cAMP levels were measured with the cre-luc reporter assay. Data represent decreasing amounts of GPR78 cDNA in each transfection.

To demonstrate that the spontaneous increase of cAMP in the presence of GPR78 and absence of genistein, HEK293/cre-luc cells were transfected with a decreasing amount of GPR78 cDNA, and cAMP levels at each transfection were measured. As shown in FIG. 4, the constitutive activity of GPR78 was dependent on the amount of GPR78 cDNA transfected into cells, indicating that the elevated basal cAMP is GPR78-expression level dependent. In addition, cells starved with serum-free medium overnight did not abolish the constitutive activity; cells incubated with charcoal-stripped serum overnight also had no effect on the activity; and cells incubated with PBS overnight prior to assay cAMP did not decrease the constitutive activity either. These results indicate that the observed constitutive activity resulted from expression of GPR78 receptor is not activated by components in the cell medium.

Example 4

GPR78 is not Coupled to Gq-Coupled Pathway

Figure 5:
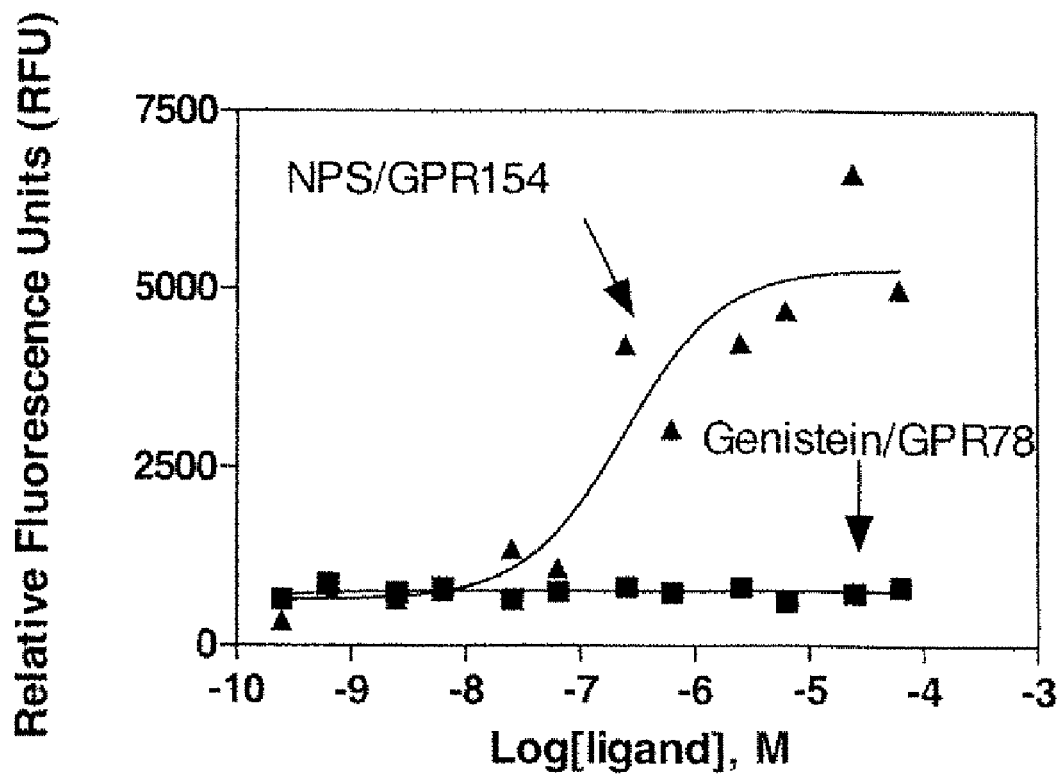
FIG. 5. GPR78 is not coupled to Gq. Ligand induced-calcium flux was measured with FLIPR in GPR78-transfected HEK293/cre-luc cells stimulated with genistein (■), or, as a positive control, in GPR40-transfected HEK293/cre-luc cells stimulated with neuropeptide S (▲). Both receptors were expressed by transient transfection of the respective cDNAs into host cells, and Ca2+ flux was measured with FLIPR.

Ca2+ flux measurements were taken to test if GPR78, when activated with genistein, is coupled to the Gq-mediated pathway. GPR78-expressing HEK/cre-luc cells were not activated by genistein at concentrations near 100 µM in Ca++ flux assay using a FLIPR measurement (FIG. 5), while GPR154, a neuropeptide S GPCR ([26]) as a positive control for the experiment, responded to neuropeptide S acutely in the Ca2+ flux assay (FIG. 5).

Example 5

Protein Kinase A- and Adenylyl Cyclase-Dependent Signaling by GPR78

Figure 6A:
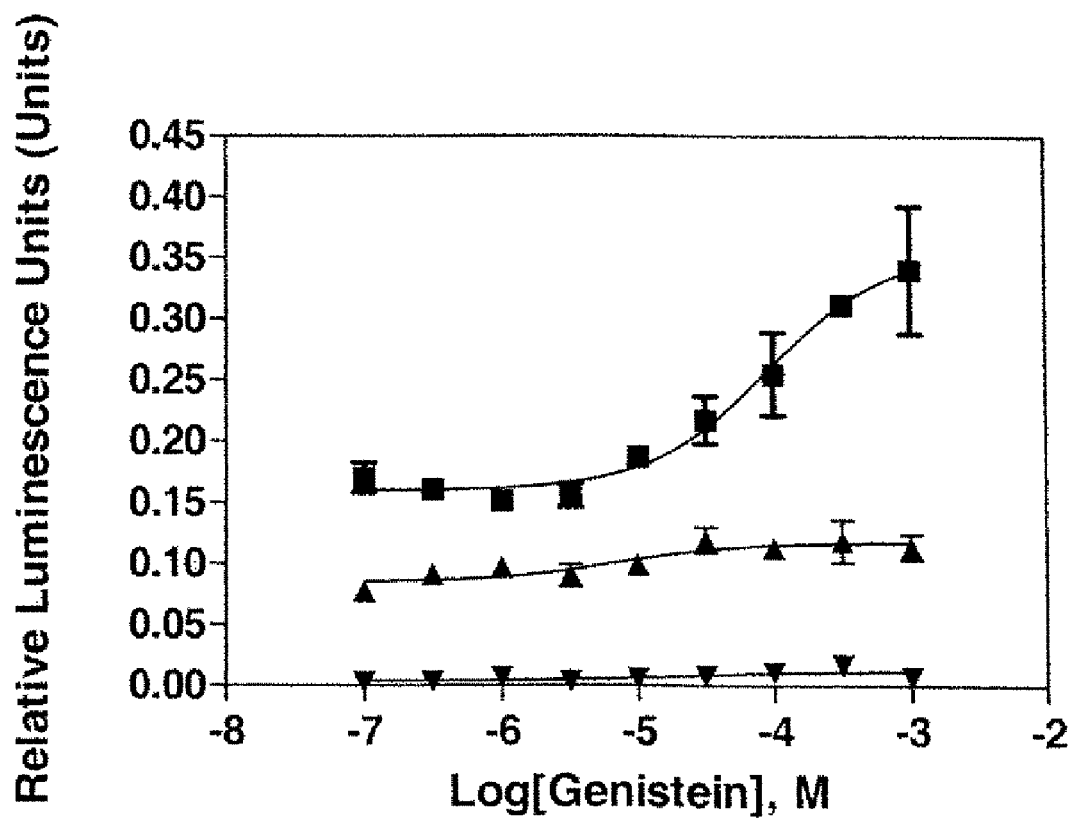
FIG. 6. Effect of the protein kinase A inhibitor H89 on genistein-induced cAMP production in GPR78-transfected (panel A) or vector control HEK293/cre-luc cells (panel B). Cells were transiently transfected for 24 hours and pre-incubated with 0 μM (■), 10 μM (▲) and 100 μM (▼) of H89 for 30 minutes at 37° C. before genistein stimulation.
Figure 6B:
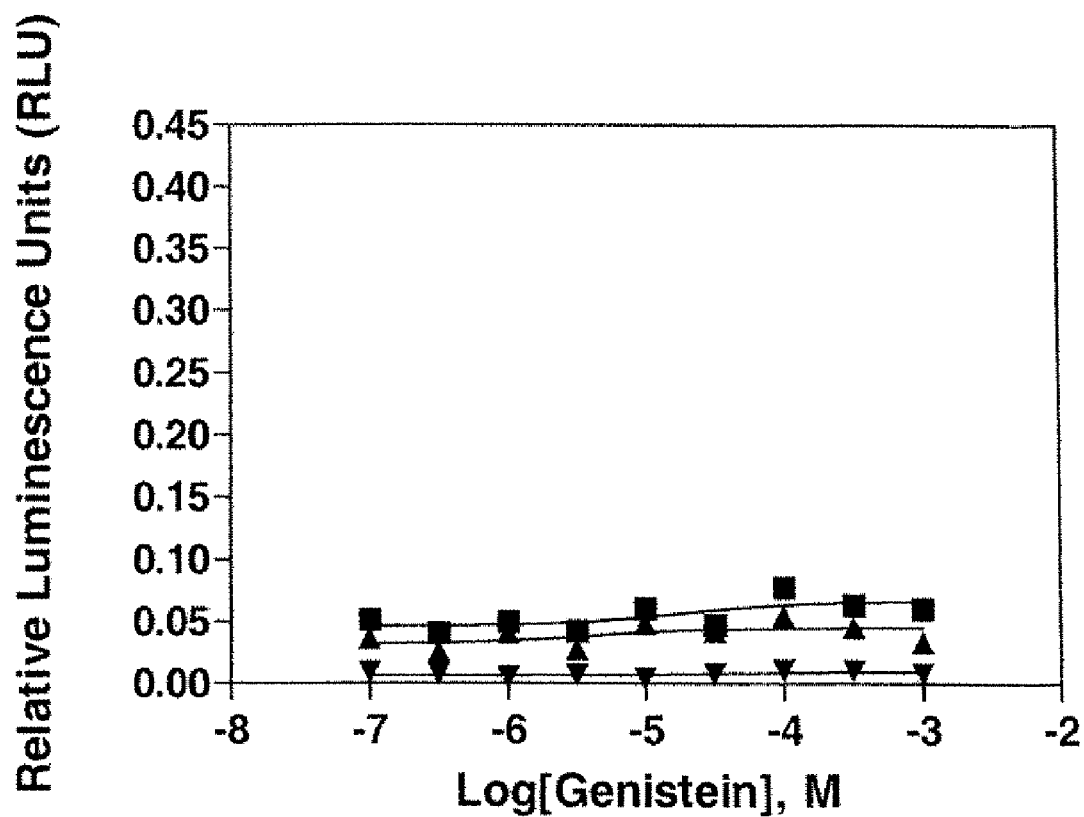

Protein kinase A inhibitor H89 was used to test if genistein activation of GPR78 is PKA dependent. HEK293/cre-luc/GPR78 cells were incubated with H89 for 30 minutes (FIG. 6A), then genistein was added and cAMP levels were measured. Most of genistein-induced cAMP was reduced at 10 µM of H89, and all cAMP accumulation was abolished at 100 µM of H89, as shown in the right portion of FIG. 6A, where genistein started to activate signaling. The basal cAMP levels in GPR78-transfected cells at genistein concentration below its EC50 (left portion of FIG. 6A) represent constitutive activity of GPR78 at various H89 concentrations. Ten µM of H89 caused decrease of the basal cAMP level by approximately half as compared to cells with no H89, whereas 100 µM of H89 completely inhibited cAMP accumulation (FIG. 6A). Mock-transfected cells displayed minimal H89 inhibition of the already low cAMP level (FIG. 6B). The data suggests both genistein-stimulated and constitutive basal cAMP accumulations are PKA-dependent and the degrees of inhibition is consistent with the reported IC50 of H89 (50 nM) [27].

Figure 7:
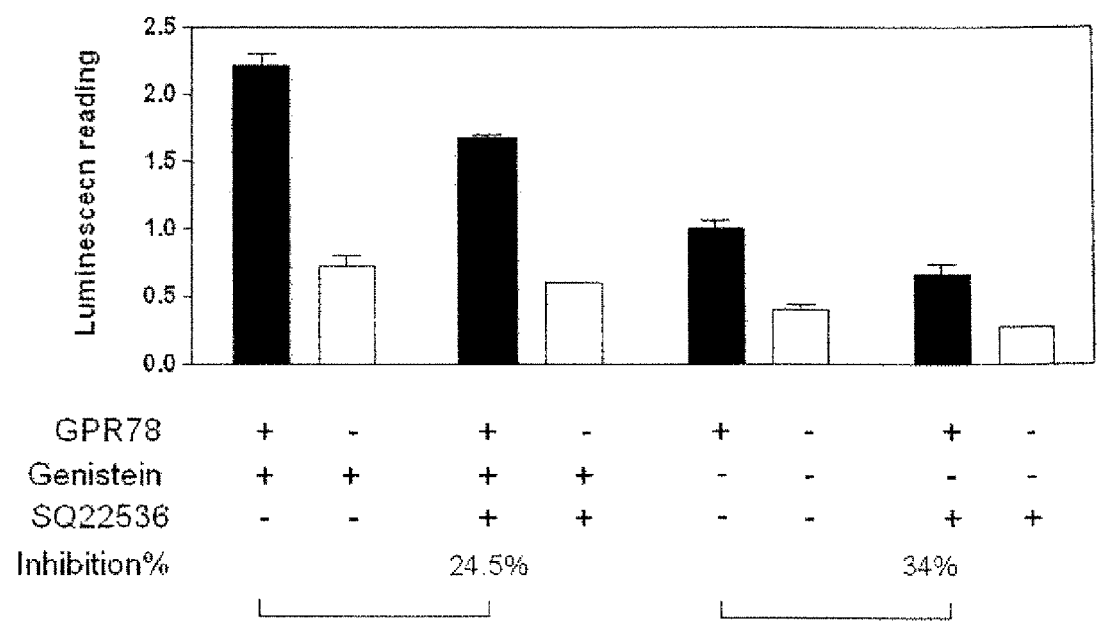
FIG. 7. Effect of the adenylyl cyclase inhibitors SQ22536 (30 μM) on genistein induced cAMP production in GPR78 cDNA-transfected (filled bars) or vector control (empty bars) HEK293/cre-luc cells. Cells were pre-incubated with the inhibitor for 30 minutes at 37 before 30 μM of genistein was added.

Inhibition of adenylyl cyclase activity also resulted in reduction of cAMP production. Adenylyl cyclase inhibitor SQ22536 (FIG. 7) at 20 µM was pre-incubated in HEK293/cre-luc/GPR78 cells and control cells, and cAMP levels were measured in the presence and absence of genistein. SQ22536 reduced genistein-stimulated cAMP by 25% and cAMP level as a result of constitutive activity of GPR78 by 34%, respectively (FIG. 7). The degree of inhibition of cAMP production is consistent with the published IC50 of 20 µM for SQ22536 in cell-free enzyme assays ([28]). The data indicates involvement of adenylyl cyclase in the signaling pathway for GPR78.

Example 6

Activation of GPR26 by Genistein

Figure 8A:
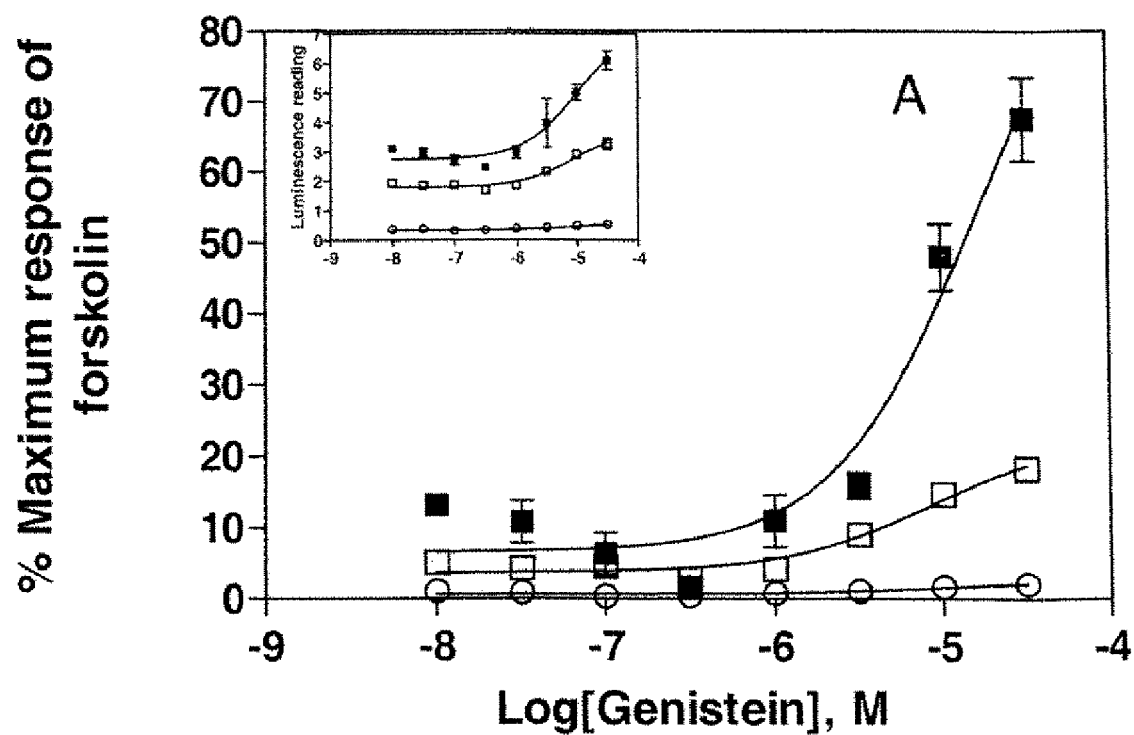
FIG. 8. Activation of GPR26 by genistein. (A) Genistein induced cAMP production in GPR26 (□), GPR78 (■) cDNA and vector (○) transfected HEK293/cre-luc cells. Data are expressed as percentage of maximum response of 10 μM forskolin, calculated from cAMP-induced luciferase luminescence readings, which are shown in the inset. (B) Genistein induced intracellular cAMP measured directly with an cAMP assay obtained from the Mesa-Scale Discovery (Gaithersburg, Md.) in HEK293/cre-luc cells stably transfected with GPR26 (□) or vector (○). Data are expressed as percentage of maximum response of 10 μM forskolin. (10 μM forskolin stimulated 195 μM of cAMP in 30,000 cells as 100% stimulation).
Figure 8B:
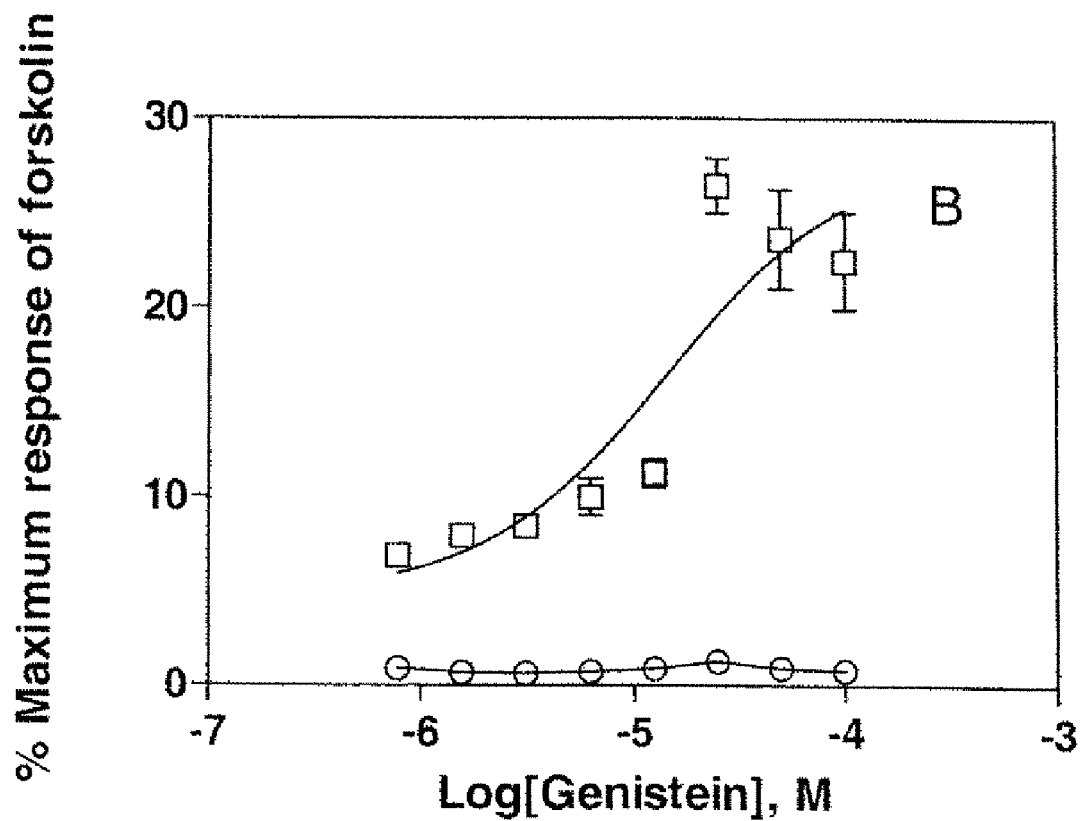

GPR26, another orphan GPCR, shares 51% identity in the seven transmembrane regions with GPR78 ([19]). The high degree of homology suggests that the two receptors belong to the same GPRC family and may be activated by identical ligands. HEK293/cre-luc cells were transiently transfected with pCR3.1-GPR26 and monitored cAMP levels upon stimulation with genistein. Genistein activated GPR26 with an EC50 of ~10 µM in the cre-luc reporter assay (FIG. 8A). The data indicates that GPR26, similar to GPR78, is activated by genistein and is also constitutively active in elevating basal cAMP level. Direct measurement of cAMP yielded comparable data as the cre-luc reporter assay: incubation of HEK293/cre-luc cells stably expressing GPR26 with genistein also resulted in stimulated cAMP production in the cells while genistein had no effect on cAMP production in control cells that had not been transfected with GPR26 (FIG. 8B).

Example 7

Identification of Small Molecule Antagonists of GPR26 and GPR78

Screening was performed by using cells transiently expressing GPR26 or GPR78. HEK293/cre-luc cells were harvested by using 0.05% trypsin EDTA solution, and were suspended in complete culture medium at a density of 20 million in 0.4 ml transfection cuvettes. One 1 microgram plasmid construct containing GPR78 or GPR26 cDNA was transfected into reporter cells by electroporation using the GenePulser (Bio-Red Laboratories, Hercules, Calif.). The transfection conditions were: voltage at 200 volts and capacity at 500 microfarads. After electroporation, cells were suspended at a density of 25,000 cells in 25 µl complete medium and placed in a 384-well plate. After 24 hours of transfection, the transfection medium was replaced with fresh complete medium. Empty plasmid vector was transfected as a negative control (mock transfection). The compounds were arranged in 96-well format in eight racks of 80, with one compound per well (250 µl at 10 mM in DMSO). Forty hours after transfection, cells were incubated with test compounds for 30 minutes (test concentration ~25 uM), then stimulated by incubation with 10 uM 4-(3-butoxy-4-methoxy-benzyl)-2-Imidazolidinone in 293 SFM II serum-free media for 6 hours at 37° C. in a 5% $CO_2$-95% air incubator. By the end of incubation, 25 ul of Bright-Glo™ (Promega, Madison, Wis.) was added into each well. Luciferase activity was determined with a Luminometer (Luminoskan Ascent, Thermo Labsystems), at a speed of 100 milliseconds per well.

Figure 9:
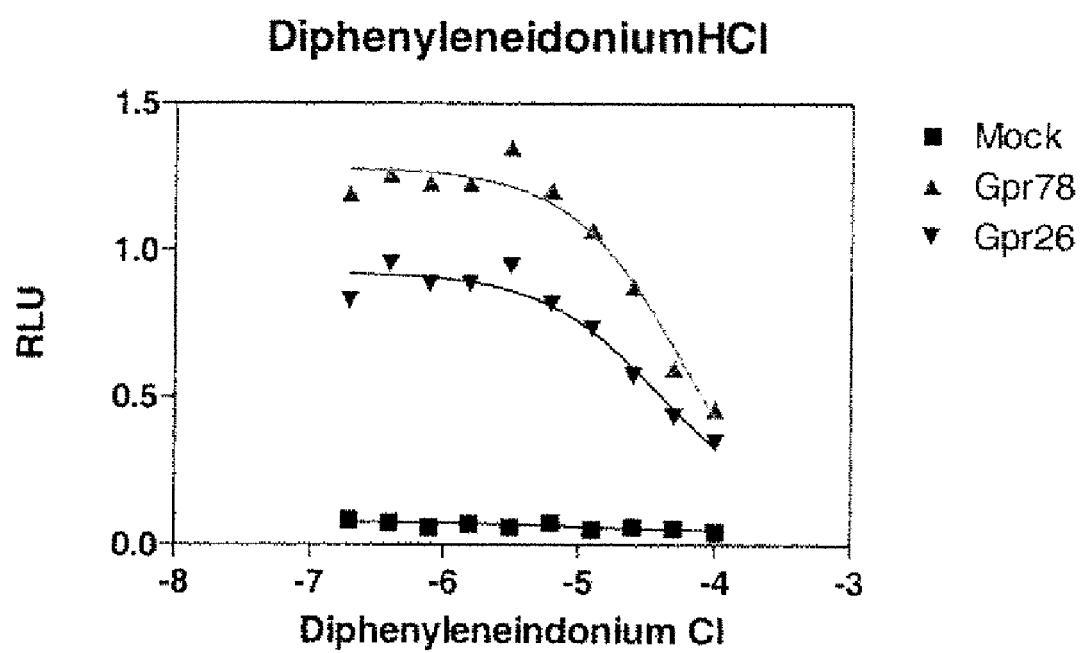
FIG. 9. Graph of potency of diphenyleneiodonium Cl in inhibition of GPPR26 and GPR78 activation (RLU=relative light unit). IC50 of diphenyleneiodonium Cl is 39 uM for GPR26 and 65 uM for GPR78.
Figure 10:
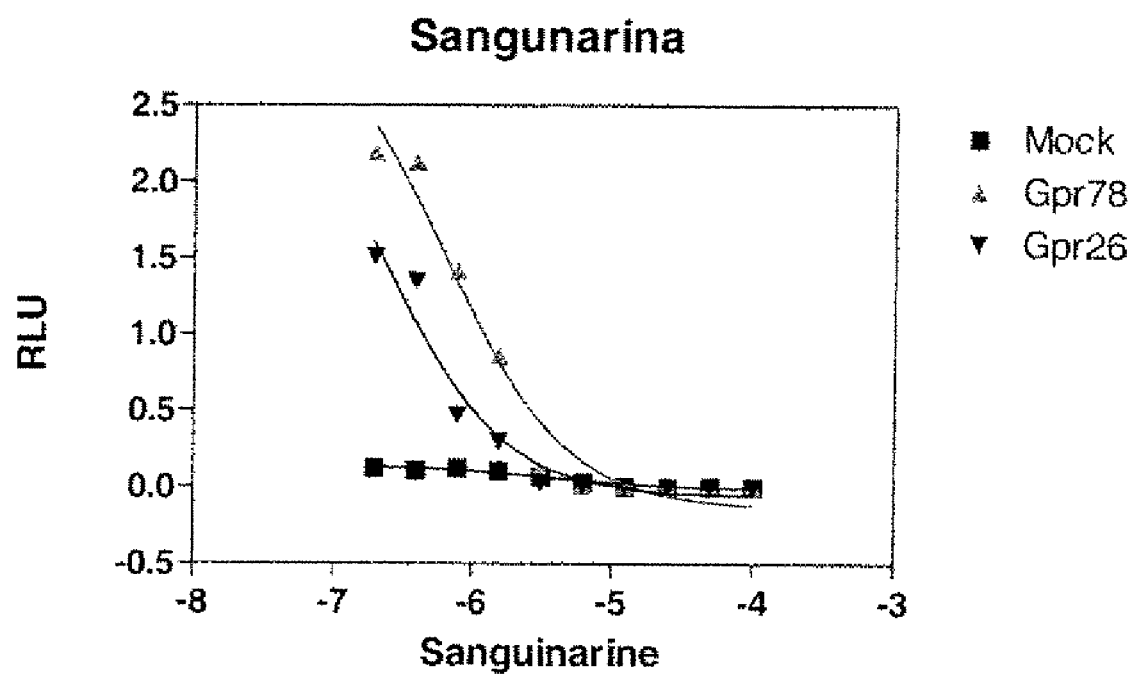
FIG. 10. Graph of potency of sanguinarine Cl in inhibition of GPPR26 and GPR78 activation (RLU=relative light unit). IC50 of sanguinarine Cl hydrate is 0.26 uM for GPR26 and 0.65 uM for GPR78.

Among the test compounds, diphenyleneiodonium Cl and sanguinarine Cl hydrate were found to inhibit activation of GPR26 and GPR78 in the cre-luc reporter assay. Thus, these two compounds were identified as GPR26 and GPR78 antagonists. To determine the inhibitory potency of the two molecules, dose-response curves were generated with the same assay method and IC50 values calculated from the curves. The IC50 of diphenyleneiodonium Cl was 39 uM for GPR26 and 65 uM for GPR78 (FIG. 9). The IC50 of sanguinarine Cl hydrate was 0.26 uM for GPR26 and 0.65 uM for GPR78 (FIG. 10).

Example 8

Screening for Small Molecule GPR26 Agonists

Stable Transfection of GPR26—Preparation of a Cell Line Expressing GPR26

Construct PCR3.1-GPR26 was transfected into HEK293/cre-luc cells using Lipofectamine 2000, and tranfectant cells were selected for G418 resistance at 500 ug/ml. Cells resistant to G418 were further diluted and selected for individual colonies. Cell lines grown from the G418-resistant colonies were screened with genistein for positive response in the cre-luciferase activity.

Screening for GPR26 Agonists

HEK293 cells expressing GPR26 were prepared by seeding 10,000 cells/well in 384-well plates (Matrix White Polystyrene TC—100 uL F 384) and grown overnight in 293 SFM II serum-free media at 37° C. in a 5% $CO_2$-95% air incubator. The medium was then removed, and 20 ul PBS containing 20 uM RO-20 (cAMP phosphodiesterase inhibitor, 4-(3-butoxy-4-methoxy-benzyl) imidazolidin-2-one) was added to the well followed by one-hour incubation in the 37° C. incubator. To the cells, 2.2 ul compound solution was then added, and the cells were incubated for 6 hours in the incubator. The final concentration of the compound was 1.25 ug/ml and DMSO 1% (vol./vol.). About 46,000 compounds were screened. Genistein at 25 uM was used as positive control for the assay. By the end of incubation, 25 ul of Bright-Glo™ (Promega, Madison, Wis.) was added into each well. Luciferase activity was determined with a Luminometer (Leadseeker). Hit compounds were selected by calculating ability to stimulate the luciferase activity. The potency (EC50) of the hits was assessed by performing dose-response curves with the test compounds at 3.75, 1.25, 0.417, 0.139 and 0.046 ug/ml.

Example 9

Screening for Small Molecule GPR26 Antagonists

Stable Transfection of GPR26—Preparation of a Cell Line Expressing GPR26

Construct PCR3.1-GPR26 was transfected into HEK293/cre-luc cells using Lipofectamine 2000, and tranfectant cells were selected for G418 resistance at 500 ug/ml. Cells resistant to G418 were further diluted and selected for individual colonies. Cell lines grown from the G418-resistant colonies were screened with genistein for positive response in the cre-luciferase activity.

Screening for GPR26 Antagonists

HEK293 cells expressing GPR26 were prepared by seeding 10,000 cells/well in 384-well plates (Matrix White Polystyrene TC—100 uL F 384) and grown overnight in 293 SFM II serum-free media at 37° C. in a 5% $CO_2$-95% air incubator. The medium was then removed, and 18 ul PBS containing 20 uM RO-20 was added to the well followed by one-hour incubation in the 37° C. incubator. To the cells, 2 ul compound solution was added, and the cells were incubated again for 0.5 hours. The final concentration of the compound was 1.25 ug/ml and DMSO 1% (vol./vol.). Diphenyleneiodinium Cl at 30 uM was used as an antagonist control. The level of inhibition of cre-luciferase activity with diphenylenciodinium Cl was defined as one hundred percent inhibition and used for calculation of compound antagonist activity. Five ul of genistein at 125 uM was added (final 25 uM), and the cells were incubated for 6 hours in the 37° C. incubator. At the end of incubation, 25 ul of Bright-Glo™ (Promega, Madison, Wis.) was added into each well. Luciferase activity was determined with a Luminometer (Leadseeker). Hit compounds were selected by calculating ability to inhibit the luciferase activity. The potency (IC50) of hits was assessed by performing the same assay for dose-response curves with the test compounds at 3.75, 1.25, 0.417, 0.139 and 0.046 ug/ml.

Example 10

Expression of GPR78 and GPR26

Figure 11A:
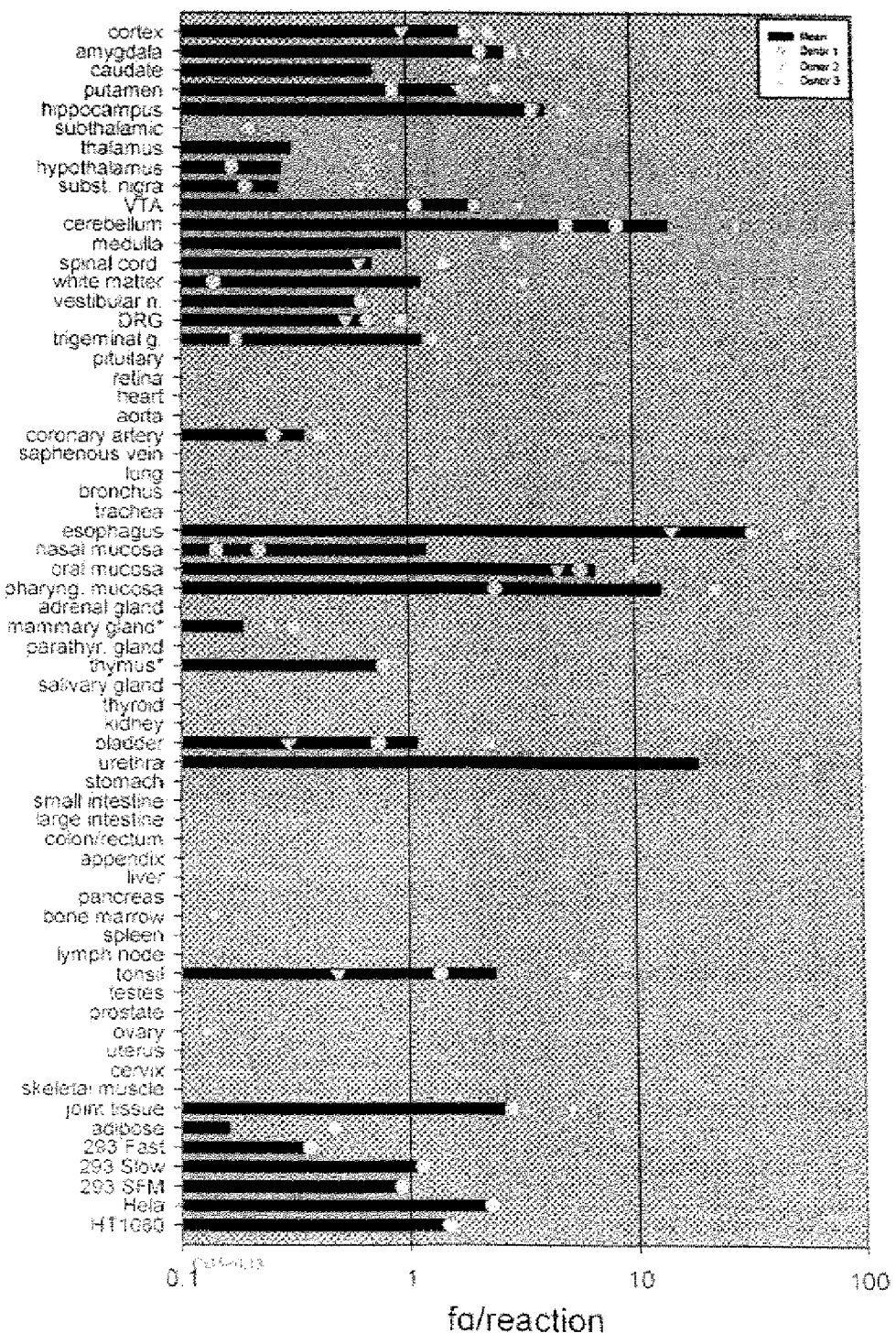
FIG. 11. Expression of GPR78 and GPR26 mRNA. (A) TAQMAN® analysis of GPR78 in human tissues. Values (bar height) represent average of measurements from three different donors indicated with the three symbols for each tissue. (B) TAQMAN® analysis of GPR26 mRNA in human tissues. The three symbols represent measurements of the same tissue from three different donors.
Figure 11B:
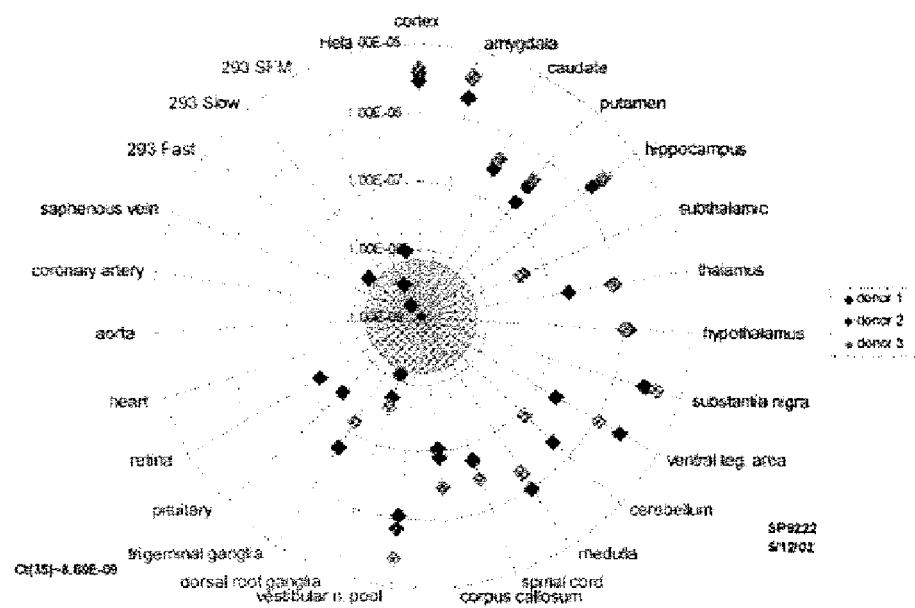
Figure 11B:
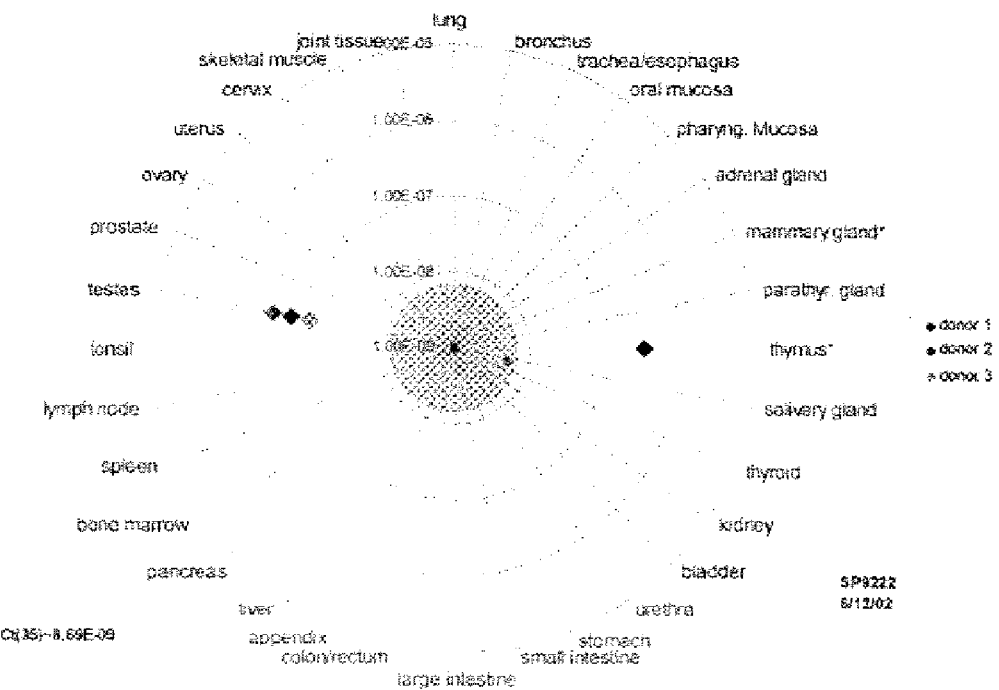

GPR78 expression in various human tissues was detected with quantitative TAQMAN® measurements (FIG. 11A). The receptor is highly expressed in a number of peripheral tissues and several regions in the brain. Peripherally GPR78 was detected at high levels in urethra, nasal and oral mucosa, esophagus, tonsil and joint tissue. Centrally it is found in cortex, amygdala, putamen, hippocampus, VTA and cerebellum (FIG. 11A). In contrast, human GPR26 expression is more restricted in the brain regions (FIG. 11B). It was found in all the brain areas tested and is particularly high in cortex, hippocampus, substantia nigra and vestibular nucleus (FIG. 11B). The only peripheral tissues detected with significant expression of GPR26 were testes and thymus; no expression was observed in all other peripheral tissues (FIG. 11B).

Example 11

Generation of GPR26 Knockout Mice

Construction of the GPR26 Targeting Vector

A DNA vector designed to remove the entire coding region of the GPR26 gene was constructed using sequencing information from GenBank® accession number AC098570. DNA fragments corresponding to the 5' and 3' regions of the GPR26 locus were subcloned into a vector at either end of the neomycin resistance gene (neo). This targeting vector was linearized using the restriction enzyme NotI and electroporated into 129S3/SvImJderived embryonic stem (ES) cells. Colonies resistant to G418 were picked and expanded for DNA analysis. DNAs from these colonies were screened for the targeted GPR26 gene by a PCR-based strategy. The predicted structure of the targeted GPR26 locus in the PCR-positive cells was confirmed by Southern-blot analysis using probes that hybridize outside of and adjacent to the construct arms.

Generation of GPR26 Knockout Mice

Cells from several correctly targeted ES cell lines were injected into C57BL/6 blastocysts to generate chimeric mice. GPR26 heterozygous (GPR26+/−) offspring were identified by a PCR-based screening strategy using three oligonucleotide primers in a multiplex reaction corresponding to the region of homology, the neo gene, and the deleted region of the GPR26 gene. These primers were designed to detect both wild-type and targeted alleles. GPR26+/− mice were then interbred to generate GPR26−/−mice. Disruption of GPR26 expression was confirmed by real-time quantitative PCR analysis.

Examples 12-26 below pertain to characterization of the GPR26 knockout (KO) cohort, analyzing behavior and pain (including hyperalgesia).

The following phenotypes were identified in the GPR26 KO mice:

(1) An anxiolytic-like effect as assessed in the elevated plus maze and open field tests.

(2) A significant decrease in basic metabolic parameters, such as oxygen consumption, $CO_2$ and heat production during long-term monitoring in the comprehensive cage monitoring system. No significant differences in body weight between the KO and WT mice were noticed in this study. However, it is possible that the KO mice might develop obesity later in life or be more susceptible to diet-induced obesity.

No significant phenotypes were detected in other behavioral and cross-therapeutic assays, such as sensorimotor gating, motor coordination, and sensitivity to pain or seizures. The histopathological evaluation of selected tissues has not revealed any differences between the KO and WT mice.

Example 12

GPR26 Knockout Mice

Irwin Functional Behavioral Battery Test

This test was performed on individually housed animals. The mice were maintained on a reverse Light:Dark cycle (12 hours light:12 hours dark); lights were turned off at 12:00 (noon), in a barrier facility with food and water available ad libitum. Testing occurred towards the end of the light phase of the cycle between 7:00 AM and 12:00 (noon). The mice were acclimated to the testing room for at least 30 minutes. Male and female GPR26 KO and B6x129 mice at 12-14 weeks of age (eight of each sex and genotype) were observed consecutively in a viewing jar (clear Perspex cylinder, 14.5×11.5 cm), an arena (clear Perspex rectangle, 55×33×18 cm, floor marked with fifteen 11 $cm^2$ squares), above the arena and in a supine position.

Neurological characteristics evaluated included abdominal tone, body tone, contact righting reflex, convulsions, gait, grip strength, limb tone, negative geotaxis, pelvic elevation, righting reflex, tail elevation, tremor, twitches, and wire maneuver. Physical characteristics evaluated included body weight, body length, coat quality, and whiskers. Autonomic characteristics evaluated included body temperature, heart rate, lacrimation, palpebral closure, piloerection, pupil reflex, respiration rate, salivation and skin color. Behavioral characteristics evaluated included bizarre behavior, body position, corneal reflex, defecation, irritability, limb grasping, locomotor activity, pinna reflex, hind leg positional passivity, neck positional passivity, supine positional passivity, tail positional passivity, provoked biting, spontaneous activity, startle response, tail pinch, toe pinch, touch escape, transfer arousal, trunk curl, and visual placing.

Results

There were no differences between the WT and GPR26 KO mice in any of the measurements.

Example 13

GPR26 Knockout Mice

Elevated Plus Maze (EPM) Test

Individually housed male mice aged 9-11 weeks (10 of each genotype) were used for this experiment. The mice were maintained on a reverse Light:Dark cycle (12 hours light:12 hours dark) in a barrier facility. Food and water were available ad libitum. Testing occurred towards the end of the light cycle between 6:00 AM and 12:00 (noon). The mice were acclimated to the testing room for at least 30 minutes.

The elevated plus maze was constructed with black Plexiglass in the shape of a plus sign with a pair of open arms surrounded by a short wall of adjustable height (0.5 cm) and a pair of closed arms that were surrounded by 30 cm-high walls. Each arm was 30 cm long. The four arms is met at the central platform (6×6 cm). Four metal legs elevated the maze 50 cm above the floor. The maze was illuminated by infrared light from the bottom. The movements of each animal were monitored by an infrared sensitive video camera with filters blocking visible light. The cameras were fixed on the ceiling of the experimental room. Each camera was connected to a computer equipped with Videotrack (Viewpoint) software for data analysis.

Each individual animal was placed in the center of the maze, facing an open arm. The time spent in the open and closed arms and the number of entries into the arms was determined using the Videotrack software. The percentage of entries into the open arms was calculated as:

(Number of entries in the open arm/Total number of entries)×100%

The number of fecal boli produced by each experimental animal during the test was also calculated. Data was analyzed between groups by unpaired t-test (GraphPad Prism).

Results

An outlier test was performed prior to inclusion results generated on individual mice in the study. One mouse from the WT group was excluded from subsequent analysis because it exhibited values for anxiety parameters that were greater than two standard deviations from the mean of the group.

Figure 12:
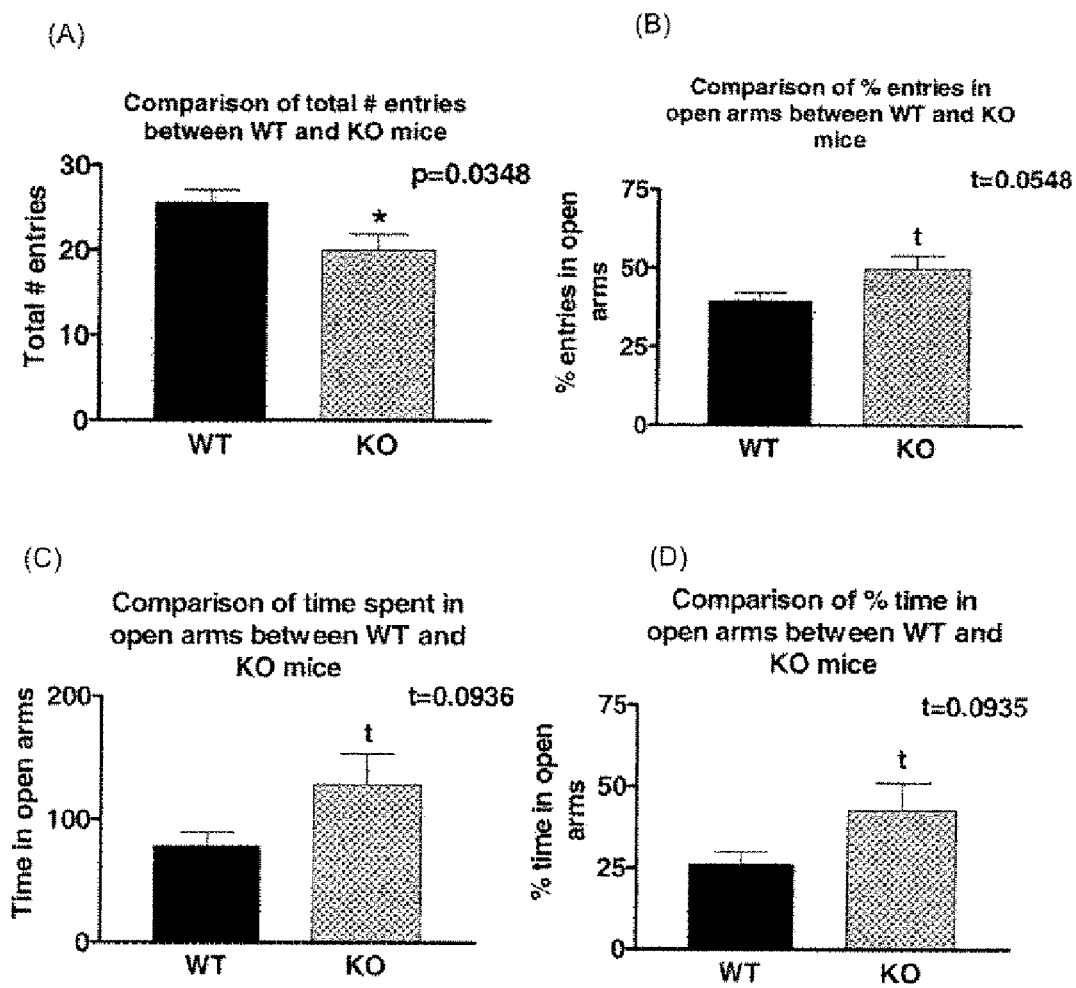
FIG. 12. Results of the Elevated Plus Maze Test. (A) Comparison of the total number of entries by the wildtype (WT) and knockout (KO) mice into any of the anus (open or closed) of the maze. GPR26 KO mice exhibited a significantly lower total number of entries than did the WT mice (P=0.0348). (B) Comparison of the percentage of entries by the WT and KO mice into the open arms of the maze. The percentage of entries into the open arms was greater for the KO mice than for the WT mice (P=0.0548). (C) Comparison of the time spent by the WT and KO mice in the open arms of the maze. The KO mice spent more time than the WT mice in the open arms (P=0.0936). (D) Comparison of the percentage of the time spent by the WT and KO mice in the open arms of the maze. This percentage was greater for the KO mice (P=0.0935).
Figure 13:
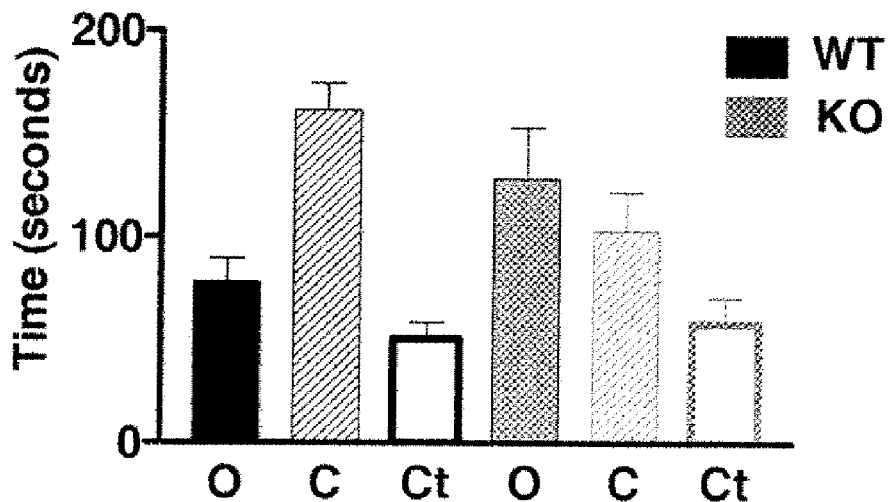
FIG. 13. Comparison of the difference in the time spent in the open and closed arms of the Elevated Plus Maze by the WT and KO mice. (A) Time spent by the WT and KO mice in the open arms (O), closed arms (C) and center (Ct) of the maze. (B) Comparison of the difference in the time spent in the open versus the closed arms of the maze by the WT and KO mice. The KO mice spent a significantly longer time in the open arms than in the closed arms (P=0.0427), exhibiting less anxious behavior. The WT mice spent more time in the closed arms than in the open aims, exhibiting more anxious behavior.
Figure 13:
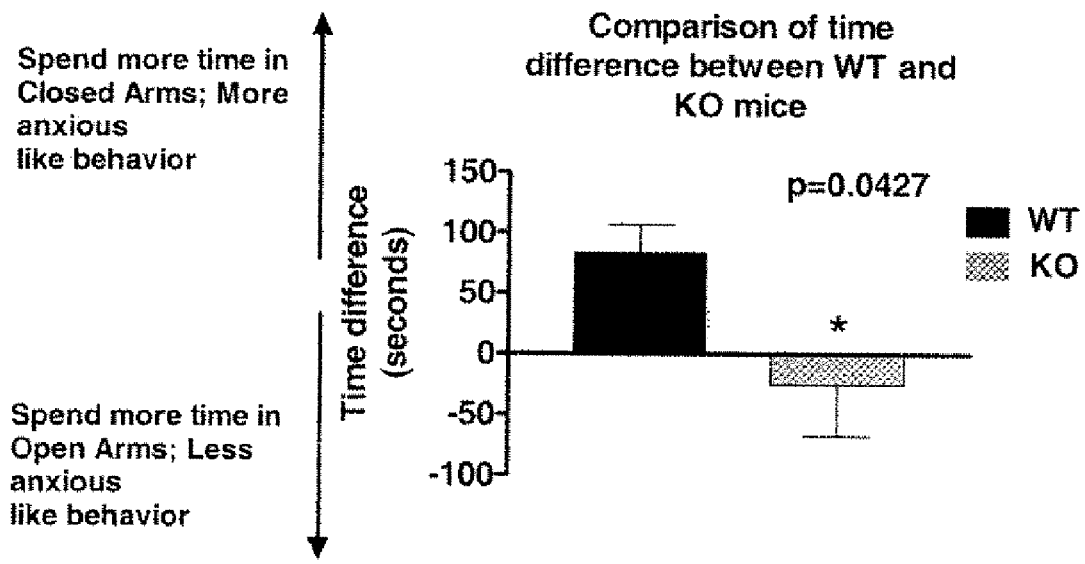
Figure 14:
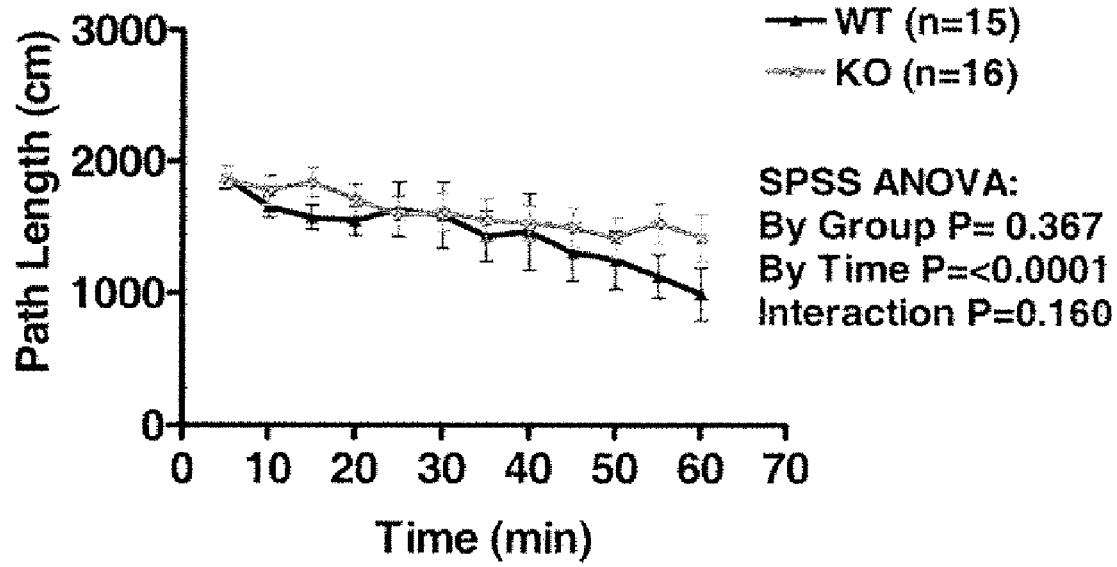
FIG. 14. Locomotion measures for the WT and KO mice in the Open Field Test. (A) Locomotion activity of the WT and KO mice as measured by path length for 60 minutes at 5-minute intervals. (B) Comparison of the total path length for the WT and KO mice (P=0.435).
Figure 14:
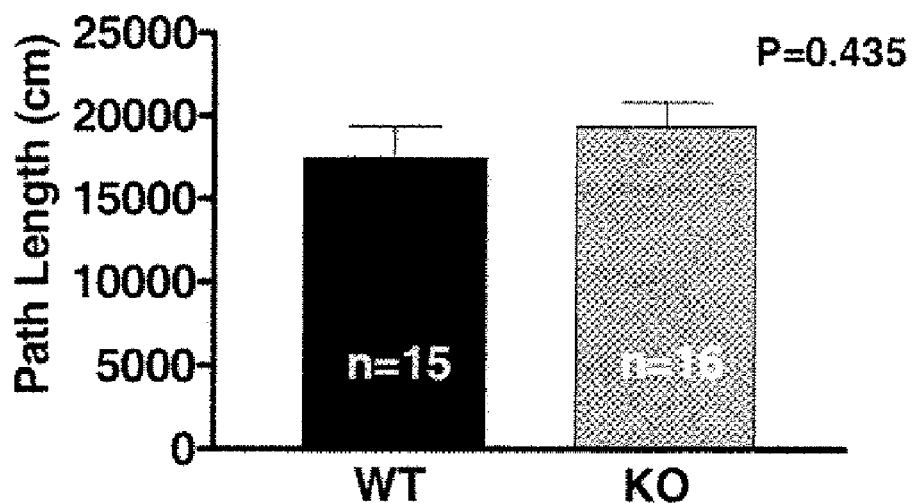
Figure 15:
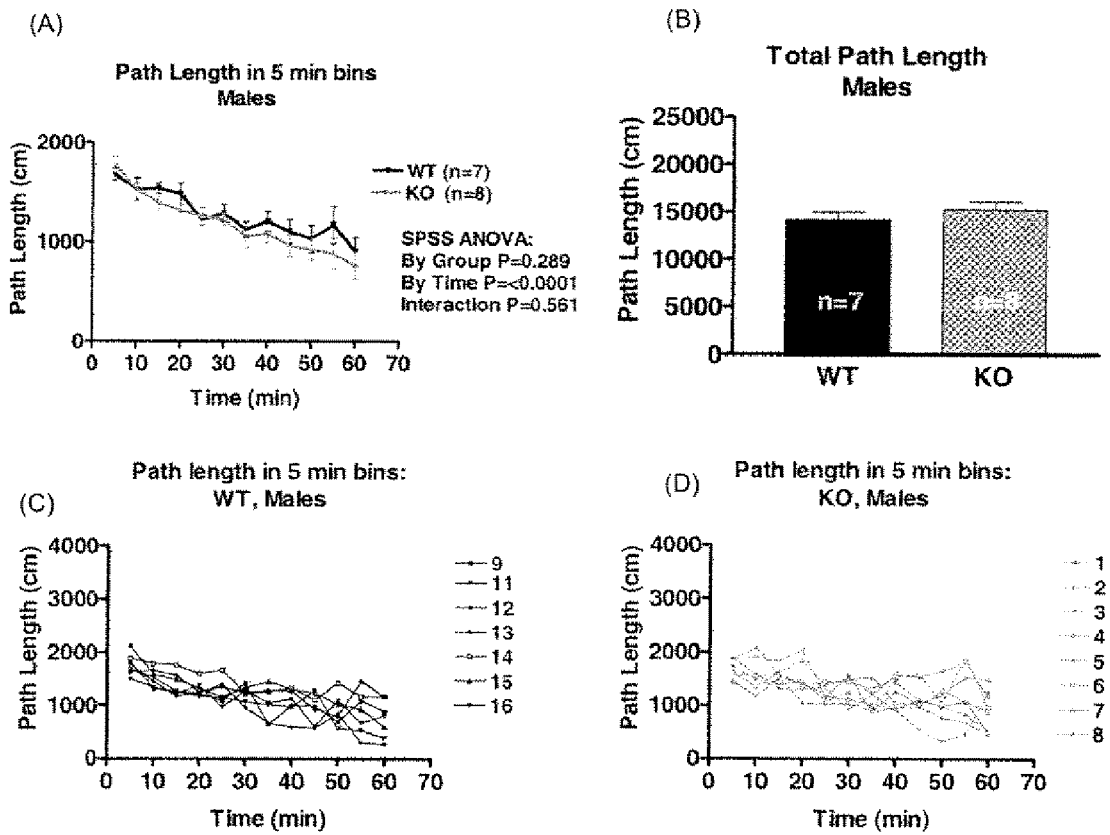
FIG. 15. Locomotion measures for the WT and KO male mice in the Open Field Test. (A) Locomotion activity of the WT and KO male mice as measured by path length for 60 minutes at 5-minute intervals. (B) Comparison of the total path length for the WT and KO male mice. (C) Locomotion activity of each of the WT male mice as measured by path length for 60 minutes at 5-minute intervals. (D) Locomotion activity of each of the KO male mice as measured by path length for 60 minutes at 5-minute intervals.

The GPR26 KO mice exhibited a significantly lower total number of entries (to either the closed or open arms) than their WT littermates (P=0.0348, FIG. 12A), suggesting that the knockout of this gene may affect locomotor activity. The KO mice exhibited a trend towards a higher percentage of entries into open arms (P=0.0548, FIG. 12B). A trend towards longer time spent in open arms was also observed in the KO mice (P=0.0936, FIG. 12C). Similarly, a trend towards a longer percent of time spent in open arms was exhibited by the KO mice (P=0.0935, FIG. 12D). A trend towards higher number of fecal boli was also observed in the KO mice (P=0.0947). A comparison of the difference between time spent in the open versus closed arms revealed that the KO mice spent a significantly longer time in the open arms than the closed arms (P=0.0427, FIGS. 13A and 13B).

Taken together these data suggest that the GPR26 gene knockout produced an anxiolytic effect in the EPM paradigm. A lower total number of entries exhibited by the KO as compared to the WT mice suggested that the KO reduced locomotor activity. A reduction in the locomotor activity could contribute to the findings observed in the anxiety parameters in this assay. It is worth noting, however, that no effect of the KO on locomotion was observed in the Irwin Functional Behavioral Battery Test, Open Field Test or Comprehensive Cage Monitoring System (see Examples 9, 11 and 20).

Example 14

GPR26 Knockout Mice

Open Field Test (OF)

Thirty-two individually housed male and female mice aged 11-13 weeks were used for this experiment (eight mice of each gender and genotype). The mice were maintained on a reverse Light:Dark cycle (12 hours on:12 hours off) in a barrier facility. Food and water were available ad libitum. Testing occurred towards the end of the light cycle between 6:00 AM-12:00 (noon). Mice were acclimated to the testing room for at least 30 minutes. The assay was performed in a custom-made Open Field Apparatus. The apparatus consisted of a 50×50 cm square chamber. The experiment was recorded and tracked by a videotracking system developed by Viewpoint.

For each mouse, the total path length and the path length for 60 minutes at 5-minute intervals were determined as measures of locomotor activity. In addition, the number of fecal boli produced by each animal during the test was recorded.

The time and the path length in the center of the open field were determined as measures of anxiety-like behavior. The center of the open field was defined as a 13.5×13.5 cm square in the geometric center of the arena. The percentage of the path length spent in the center of the open field was calculated as (Path length in the center/Total path length)×100%

The path length for 60 minutes at 5-minute intervals was analyzed by two factor ANOVAs with genotype and sex as independent variables (SPSS). All other parameters were compared using unpaired t-test (GraphPad Prism).

Results

Figure 16:
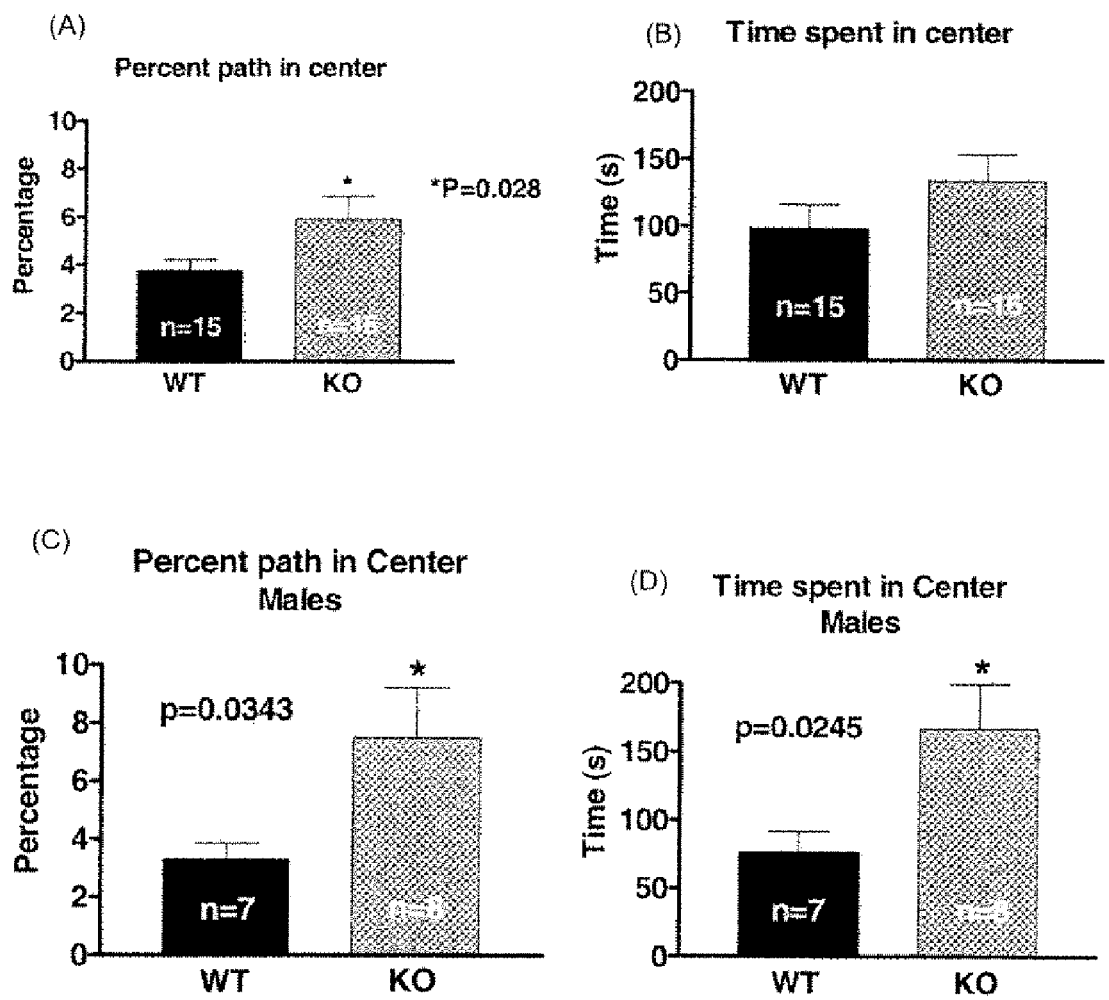
FIG. 16. Anxiety measures for the WT and KO male mice in the Open Field Test. (A) Comparison of the WT and KO mice in terms of the percentage of the path that was in the center of the open field. The KO mice exhibited a significantly higher percent path in the center ($F_{1,28}$=5.39, P=0.028) than did the WT mice. (B) Comparison of the WT and KO mice in terms of the time spent in the center of the open field. (C) Comparison of the WT and KO male mice in terms of the percentage of the path that was in the center of the open field. The KO males exhibited a significantly higher percent path in the center (P=0.0343) than did the WT males. (D) Comparison of the WT and KO male mice in terms of the time spent in the center of the open field. The KO males spent a significantly longer time in the center of the open field than did the WT males (P=0.0245).

The GPR26 KO mice traveled a significantly longer distance in the center of the open field ($F_{1,28}$=5.39, P=0.028, FIG. 16A), but there was no effect or interaction with gender. However, a significant interaction between gender and genotype was detected in the percentage of the total path in the center ($F_{1,28}$=4.28, P=0.048), which was due to KO males traveling a greater percentage of their total path distance in the center than WT males (P=0.0503). There were also significant interactions between gender and genotype for the time spent in the center ($F_{1,28}$=4.65, P=0.04). When the anxiety measures were compared between the two groups separated by gender, the KO males traveled significantly longer distances (P=0.0343, FIG. 16C) and spent a significantly longer time (P=0.0245, FIG. 16D) in the center of the open field than the WT males. There were no differences between the KO and WT females with respect to the distance traveled or the time spent in center of the open field.

The number of fecal boli, another measure that may be related to anxiety-like behavior in the open field, was not different between the KO and WT mice.

Conclusion

The significantly increased path lengths in the center of the open field exhibited by the KO mice, along with the significantly increased path lengths and times spent in center of the open field (specifically by the KO males), suggest that the knockout of the GPR26 gene may have had an anxiolytic effect. The absence of differences between KO and WT females suggests that the anxiolytic effect was sexually dimorphic.

Example 15

GPR26 Knockout Mice

Novel Environment-Induced Feeding Suppression (NEWS) Assay

Individually housed male mice aged 10-12 weeks (10 of each genotype) were used for this experiment. The mice were maintained on a reverse Light:Dark cycle (12 hours on:12 hours off) in a barrier facility with food and water available ad libitum. The testing occurred towards the end of the light cycle between 6:00 AM and 12:00 (noon). Mice were acclimated to the testing room for at least 30 minutes.

Days 1, 2, 3 and 5 (Home Cage)

A Petri dish containing crushed Graham crackers was placed in the corner furthest from each mouse in its home cage. The time to approach (defined as the nose of the mouse directed within 1 cm of the dish) and consume the crackers (scored as eating, not just picking up or touching the food) was recorded immediately following the placement of the dish into home cage.

Day 4 (Novel Environment)

The procedure followed was the same as described for the home cage with the following adjustment: On day 4, the mouse was placed in a new cage with clean bedding (novel environment) for the duration of the experiment. The mice were subsequently returned to their respective home cages for day 5 testing.

The latency to approach and/or consume food on day 4 was used as a measure of anxiety. The times for a mouse to approach and consume the food were compared across the acclimation and experimental days by ANOVA with Bonferroni's post-hoc analyses employed for pair-wise comparisons between the experimental days.

Results

One GPR26 KO mouse did not consume the food for the entire duration of the experiment and was excluded from the analyses. There was no difference in the latency to consume between GPR26 KO and WT mice as revealed by ANOVA with genotype as the main factor ($F_{1,\,17}$=0.337, p=0.569). There was a significant effect of the day of testing on the latency to consume ($F_{4,\,68}$=11.05, p<0.0001). There was no interaction between the genotype and day of testing ($F_{4,\,68}$=1.212, p=0.314).

There was a significant difference in the latency to approach the food between the GPR26 KO and WT mice as revealed by ANOVA with genotype as the main factor ($F_{1,\,17}$=4.939, p=0.04). However, post-hoc analyses did not show any difference in the latency to approach the food on day 4 (p=0.366). There was a trend towards an effect of the day of testing on latency to approach ($F_{4,\,68}$=2.355, p=0.062). However, this did not reach statistical significance. There was no interaction between genotype and the day of testing ($F_{4,\,68}$=0.867, p=0.488).

Conclusion

There was no difference in the latency to approach or consume food between the GPR26 KO and WT mice on day 4 of the test, suggesting that the knockout of the GPR26 gene did not affect anxiety-like behavior in this experimental paradigm.

Example 16

GPR26 Knockout Mice

Tail Suspension Test (TST)

Individually housed, male GPR26 KO mice and their WT littermates aged 13-15 weeks were used for this experiment (ten mice per genotype). The mice were maintained on a reverse Light:Dark cycle (12 hours on:12 hours off) in a barrier facility. Food and water were available ad libitum. Testing occurred towards the end of the light cycle between 6:00 AM and 12:00 (noon). The mice were acclimated to the testing room for at least 30 minutes.

An automated tail suspension test apparatus (Med-Associates) was used to measure the total duration of immobility (seconds) in the tail suspension test. Using adhesive Scotch tape, each mouse was suspended by the tail on a hook connected to a strain gauge. The gauge transmitted all movements of the mouse to a central unit connected to a computer for data analysis. The total duration of immobility (defined as the cumulative time when the force of the mouse's movement is below a preset threshold criterion) was automatically calculated during the 6-minute test. The apparatus was configured as follows: gain (signal amplification)=4, threshold 1=3 and resolution=200 msec. The periods when the mouse's movements were below threshold 1 (<3) for at least 200 msec were counted as immobility time. The duration of immobility was analyzed between groups by an unpaired t-test (GraphPad Prism).

Results

The duration of immobility was not different between the GPR26 KO mice and their WT littermates (P=0.6505). An absence of difference in the immobility time suggests that the knockout of the GPR26 gene does not induce an "antidepressant"-like phenotype in the tail suspension test.

Example 17

GPR26 Knockout Mice

Startle and Pre-Pulse Inhibition Test

Individually housed male GPR26 KO mice and their WT littermates (ten of each genotype) aged 11-13 weeks were used for these experiments. The mice were maintained on a reverse Light:Dark cycle (12 hours on:12 hours off) in a barrier facility. Food and water were available ad libitum. The experiment was performed towards the end of the light phase (7:00 AM to 11:00 AM). The mice were acclimated to the procedure room for at least 30 minutes, weighed, and placed in the animal enclosures of the sound attenuating chambers (StartleMonitor, Kinder Scientific).

The effects on baseline startle response were tested on the first day. The mice were allowed to acclimate for 5 minutes inside the chambers, then presented with 6 acoustic stimuli of different intensities (duration: 40 msec at 0, 80, 90, 100, 110 and 120 dB). A total of 30 trials were presented in a pseudo-randomized manner with an average inter-trial-interval (ITI) of 15 seconds (range: 10-20 sec). Background noise of 70 dB was presented during the ITI. The StartleMonitor system and computer recorded the average amplitude of startle within a 150 msec window following each of the acoustic stimuli. Analysis of Variance (ANOVA) with Bonferroni's post-hoc analyses was used to compare the two genotypes. The mice were returned to their cages after the first day.

The effects on pre-pulse inhibition were examined on the following day. The mice were acclimated to the chamber for 5 minutes, then presented with five different trials:

1. no stimulus, where only background (70 dB) was presented,
2. 120 dB pulse alone,
3. pre-pulse of 3 dB above background followed by 120 dB pulse,
4. pre-pulse of 6 dB above background followed by 120 dB pulse, or
5. pre-pulse of 12 dB above background followed by 120 dB pulse.

Each pre-pulse was 20 msec long and preceded the 40 msec-long 120 dB pulse by 100 msec. The test session was presented in 12 blocks, each with ten trials. Blocks 1 and 12 consisted of 10 presentations of 120 dB pulses with an average ITI of 15 seconds (range: 10-20 sec). Blocks 2-11 each consisted of two presentations of each pulse type (no stimulation, 120 dB alone, pre-pulse of 3, 6 or 12 dB above background each followed by 120 dB pulse) presented in a pseudo-random manner with an average ITI of 15 seconds (range: 10-20 sec). Repeated measures ANOVA with Bonferroni's post-hoc analyses were used to compare the effect of the three pre-pulses on the startle amplitudes and the extent of pre-pulse inhibition.

Results

A main effect of pulse intensity on startle reflex amplitude was seen by ANOVA ($F_{5,\ 90}$=76.779, p<0.0001). A main effect of genotype on startle amplitude was not observed by ANOVA ($F_{1,\ 18}$=0.106, P=0.749) nor was an interaction between genotype and pulse amplitude ($F_{5,\ 90}$=0.268, P=0.929).

A main effect of pre-pulse intensity on the amplitude of startle reflex was observed by ANOVA ($F_{3,\ 54}$=101.434, p<0.0001). ANOVA did not reveal a main effect of genotype on startle reflex amplitude in the presence of a pre-pulse ($F_{1,\ 18}$=0.815, P=0.378) or an interaction between genotype and pre-pulse intensity ($F_{3,\ 54}$=0.604, P=0.616).

A main effect of pre-pulse amplitude was seen on percent pre-pulse inhibition by ANOVA ($F_{2,\ 36}$=109.669, p<0.0001). There was no effect of genotype on the percent pre-pulse inhibition as revealed by ANOVA ($F_{1,\ 18}$=0.633, P=0.437) or a significant interaction between genotype and pre-pulse amplitude ($F_{2,\ 36}$=1.107, P=0.342).

Conclusion

An absence of differences in the baseline startle amplitude and percent pre-pulse inhibition between the KO and WT mice suggests that the GPR26 gene knockout did not affect sensorimotor gating in this paradigm.

Example 18

GPR26 Knockout Mice

Rotarod Test

Individually housed male mice aged 13-15 weeks were used for this experiment (8 animals per genotype). The mice were maintained on a reverse Light:Dark cycle (12 hours on:12 hours off) in a barrier facility. Food and water were available ad libitum. Testing occurred towards the end of the light cycle between 7:00 AM and 12:00 (noon). The mice were acclimated to the testing room for at least 30 minutes.

The assay was carried out using four EzRod test chambers kept in a laminar hood. For the accelerating rotarod paradigm, the mice were given 10 trials with the maximum duration of 3 minutes and a 30-second ITI. Each mouse was placed on the EZRod machine and the latency to fall was recorded for all of the trials. If the mouse fell or 3 minutes elapsed, the mouse was left at the bottom of EzRod test chamber for 30 seconds before the initiation of the next trial.

The latency to fall was compared between the two groups by analysis of variance (ANOVA) with repeated measures.

Results

There was no difference in the latency to fall between the GPR26 KO mice and their WT littermates as revealed by ANOVA with repeated measures ($F_{1,\ 13}$=2.931, P=0.111). As expected, ANOVA with repeated measures showed a significant main effect of the trials ($F_{9,\ 117}$=1.173, P=0.319).

Example 19

GPR26 Knockout Mice

Pentylenetetrazole (PTZ)-Induced Seizure Test

Individually housed GPR26 KO and WT male mice aged 16-18 weeks (ten per genotype) were used for this experiment. The mice were maintained on a reverse Light:Dark cycle (1.2 hours on:12 hours off) in a barrier facility. Food and water were available ad libitum. Testing occurred towards the end of the light cycle between 6:00 AM and 12:00 (noon). The mice were acclimated to the testing room for at least 30 minutes. The mice were placed under a heat lamp to dilate their tail veins. Each mouse was restrained in a standard PVC restraint tube (Braintree Scientific) and a butterfly needle (27G, ½ in) was inserted into the tail vein. PTZ (5 mg/ml, dissolved in saline) was pumped by an automated infusion pump (Harvard Apparatus) at a rate of 0.5 ml/min into the tail vein. The latencies to the following three seizures were recorded:

1. Facial and forelimb (FF) clonus: characterized by mouth movements as if chewing with clonic movement of the forelimbs.
2. Running bouncing clonus (RBC): a dramatic, violent whole-body clonus, including episodes of running and bouncing or jumping.
3. Tonic hind limb extensor (THE) convulsion: convulsion characterized by extreme rigidity, with forelimbs and hind limbs extended caudally and head held perpendicular to the body; this seizure was terminal.

If the infusion of PTZ occurred for three minutes without the induction of a seizure, the subject was euthanized by Xenongen Biosciences' Institutional Animal Care and Use Committee (IACUC) approved methods. The amount of PTZ (mg/kg) required to induce the seizure was calculated according to the following equation:

$$\frac{\text{mg/ml } PTZ * ((\text{rate of infusion}/60 \text{ sec}) * \text{latency to seizure})}{\text{Body weight in kg}}$$

For each seizure type an unpaired t-test (GraphPad Prism) was used to compare the two groups.

Results

There were no differences between the GPR26 KO and WT mice with respect to the average dose of PTZ required to induce the facial and forelimb clonus ($P=0.1136$), running-bouncing clonus ($P=0.1218$), or tonic hind limb extensor convulsion ($P=0.1797$). This indicates that knocking out the GPR26 gene did not have an effect on the susceptibility to PTZ-induced seizures.

Example 20

GPR26 Knockout Mice

Hot Plate Test

Individually housed female mice aged 13-14 weeks were used for this experiment (eight mice per genotype). The mice were maintained on a reverse Light:Dark cycle (12 hours on:12 hours off) in a barrier facility. Food and water were available ad libitum. Testing occurred towards the end of the light cycle between 6:00 AM and 12:00 (noon). The mice were acclimated to the testing room for at least 30 minutes.

The hot plate (Columbus Instruments) was placed under a laminar flow hood for the testing and set to 52° C. The hot plate was surrounded by a Plexiglass barrier to prevent the mice from escaping. Each mouse was placed on the hot plate and a timer was started simultaneously. The latency (seconds) to the first pain response (hind-paw shake or lick, escape jump) was recorded, and the mouse was immediately removed from the hot plate. If the mouse did not exhibit a pain response within 60 seconds, it was removed from the hot plate. The latency to withdrawal between the two groups was compared by the Mann-Whitney test (GraphPad Prism).

Results

The latency to the first pain response did not differ between the WT and KO mice ($P=0.1949$, $n=8$).

Example 21

GPR26 Knockout Mice

Formalin Pain Test

Individually housed, male mice (9 mice per genotype) aged 14-16 weeks were used for this experiment. The mice were maintained on a reverse Light:Dark cycle (12 hours on:12 hours off) in a barrier facility. Food and water were available ad libitum. The testing occurred towards the end of the light cycle between 6:00 AM and 12:00 (noon). The mice were acclimated to the testing room for at least 30 minutes.

After acclimation, two mice were placed into one divided shoebox cage with no bedding (one mouse on each side of the divider). The mice were habituated to the cage for 30 minutes under a laminar hood. After habituation, the mice were gently restrained and one hind paw was isolated for injection. Twenty μl of a 2% formalin solution was injected into the plantar surface of one hind paw. Two mice were simultaneously injected and immediately placed back into the shoebox cage. This cage was placed in a custom-made video chamber (Noldus) with infrared lights and a camera positioned directly under the shoebox cage. The behavior was recorded for 45 minutes and stored as a computer media file (Viewpoint, Numeriscope). The behavior media files were analyzed with The Observer (Noldus) software, and the duration of pain behavior was recorded in 5-minute bins. The duration was divided into Early Phase (0-10 minutes) and Late Phase (10-45 minutes) and analyzed between groups by unpaired t-test (GraphPad Prism).

Results

There were no differences between the GPR26 KO mice and their WT littermates in the time spent licking and biting the formalin-injected hind paw during the early ($P=0.5086$) or late ($P=0.649$) phases. A comparison of the hind paw swelling following formalin injection also failed to reveal any difference between the KO and WT mice ($P=0.8521$). An absence of differences in the duration of nociceptive behavior following formalin hind paw injection between the KO and WT mice suggests that the knockout of the GRP26 gene did not affect acute or chronic phases of pain induced by formalin.

Example 22

GPR26 Knockout Mice

Carrageenan-Induced Hyperalgesia Measured by the Von Frey Test

Individually housed female mice aged 15-16 weeks were used for this experiment (8 mice per genotype). The mice were maintained on a reverse Light:Dark cycle (12 hours on:12 hours off) in a barrier facility. Food and water were available ad libitum. The testing occurred towards the end of the light cycle between 6:00 AM and 12:00 (noon).

The left hind paw of each mouse was injected with 20 µl of 2% carrageenan and placed in a Plexiglass enclosure above a wire grid for habituation. The mice were tested 30 minutes after the injection to allow for habituation to the apparatus, recovery from the injection, and for the peak action of carrageenan. An automated von Frey filament (Stoelting Co., Basile Italy) was used to measure the amount of force necessary to cause a nociceptive response, i.e., paw withdrawal. The maximum amount of force allowed was 20 g, and the time to achieve this level was 20 seconds. Each hind paw of the mouse was tested twice, with approximately 5 minutes between each force measurement, for a total of four measurements per mouse. The Difference score was calculated by subtracting the mechanical threshold of the uninjected hind paw from the injected hind paw:

Difference score=Mech. threshold (uninjected)−Mech. threshold (injected)

The Difference score of WT and KO mice was compared using the Mann-Whitney test (GraphPad Prism).

Results

The difference scores of the WT and GRP26 KO mice (P=0.9591) did not differ significantly, suggesting that the knockout of the GPR26 gene did not have an effect on the carrageenan-induced mechanical hyperalgesia.

Example 23

GPR26 Knockout Mice

Metabolism and Activity in the Comprehensive Cage Monitoring System

Nineteen to twenty-one week old male mice were used for this assay (8 mice per genotype). The mice were maintained on a reverse Light:Dark cycle (12 hours on:12 hours off) in a barrier facility. Food and water were available ad libitum.

The Comprehensive Cage Monitoring System (CCMS from Columbus Instruments, Columbus, Ohio) allows long-term, automated, non-invasive collection of 9 parameters simultaneously in 16 individual animals.

The CCMS is comprised of 16 individual units. For this study, the experimental window lasted 48 hours and began and ended at the start of the dark phase. During that time, the following parameters were measured:

$VO_2$—oxygen consumption in ml/kg/hr (calculated by Oxymax software using $O_2$ differential and body weight)

$VCO_2$— carbon dioxide production in ml/kg/hr (calculated by Oxymax software using $CO_2$ differential and body weight)

RER—respiratory exchange ratio ($VCO_2/VO_2$) (calculated by Oxymax software)

Heat—kcal/kg/hr (calculated by Oxymax software using $O_2$ consumption, $CO_2$ production and body weight)

Total X (Horizontal) Activity—measured by infra-red (IR) beams and detectors; activity was scored whenever a beam was broken X (Horizontal) Ambulatory Activity—measured by IR beams and detectors; activity was scored only when two different beams were broken sequentially Z (Vertical) Activity—measured by IR beams and detectors; both rearing and licking activity were scored.

Licking frequency—measured electronically when the mouse touched the water dispenser to complete a low current circuit X non-ambulatory Activity—calculated by subtracting X ambulatory counts from X total counts Oxygen and carbon dioxide concentrations were measured sequentially in the 16 units. The time required for a single round of gas measurements in all of the chambers was defined as an interval. The interval lengths may have varied slightly depending on the environmental parameters of the room (temperature and humidity) and the physiological parameters of the experimental mice. On average, each interval was 48 minutes long. The exact time that an interval ended for each chamber is part of the output generated by the CCMS software. All of the activity endpoints described above were the cumulative values counted by the detectors during each interval.

In order to separately analyze dark and light phases, all of the data were summed into individual days and photoperiods. Data were analyzed by a repeated measures ANOVA with body weight as a covariate in the metabolic endpoints except for RER.

Comprehensive Cage Monitoring System—Metabolic

The following endpoints were included:
$VO_2$
$VCO_2$
RER
Heat

Body weights of the animals were taken before placing the mice in the CCMS chambers and when they were removed after 48 hours. The initial body weights were used by the software to automatically calculate some of the endpoints.

Comprehensive Cage Monitoring System—Activity

Figure 17:
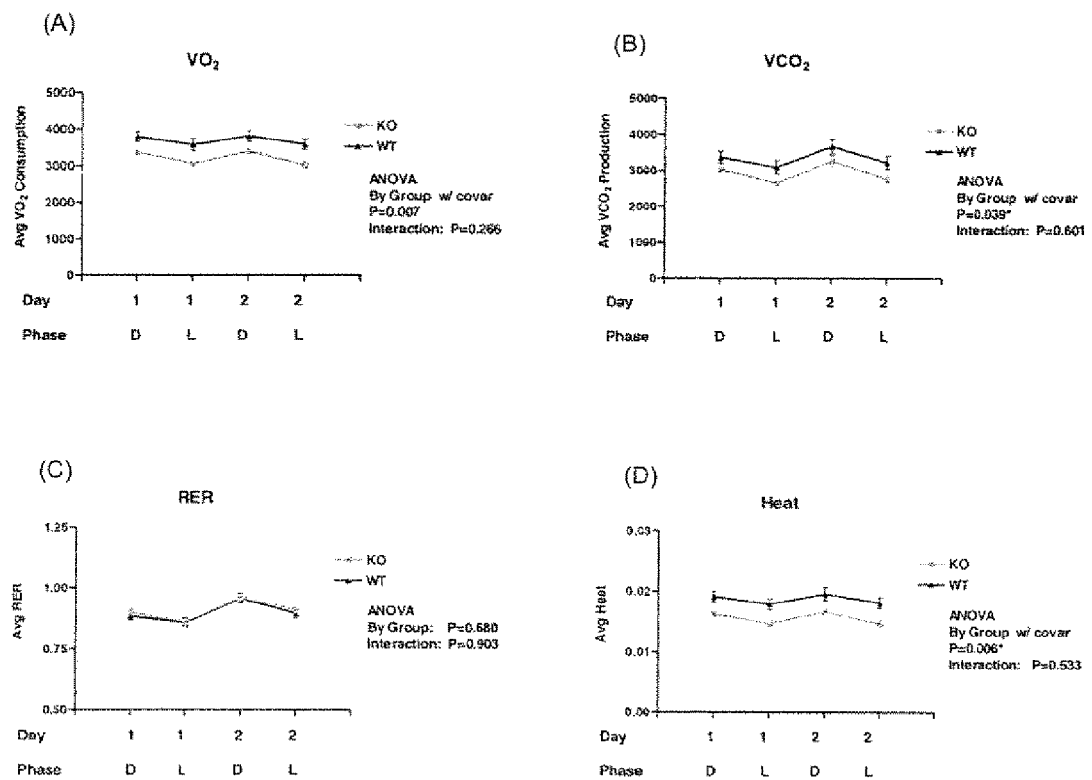
FIG. 17. Metabolic measures by photoperiod in the Comprehensive Cage Monitoring System (CCMS). The results are presented as mean±SEM with the data summed for the dark (D) and light (L) phases. (A) Comparison of oxygen consumption by the KO and WT mice. The KO mice exhibited lower oxygen consumption ($F_{1,13}$=10.34, P=0.007). (B) Comparison of carbon dioxide production by the KO and WT mice. The KO mice exhibited lower carbon dioxide production ($F_{1,13}$=5.28, P=0.039). (C) Comparison of the respiratory exchange ratio (RER) for the KO and WT mice. The RER quotient did not differ significantly for the two groups of mice (P=0.680). (D) Comparison of the heat produced by the KO and WT mice. The KO mice exhibited lower heat production ($F_{1,13}$=10.70, P=0.006).
Figure 18A:
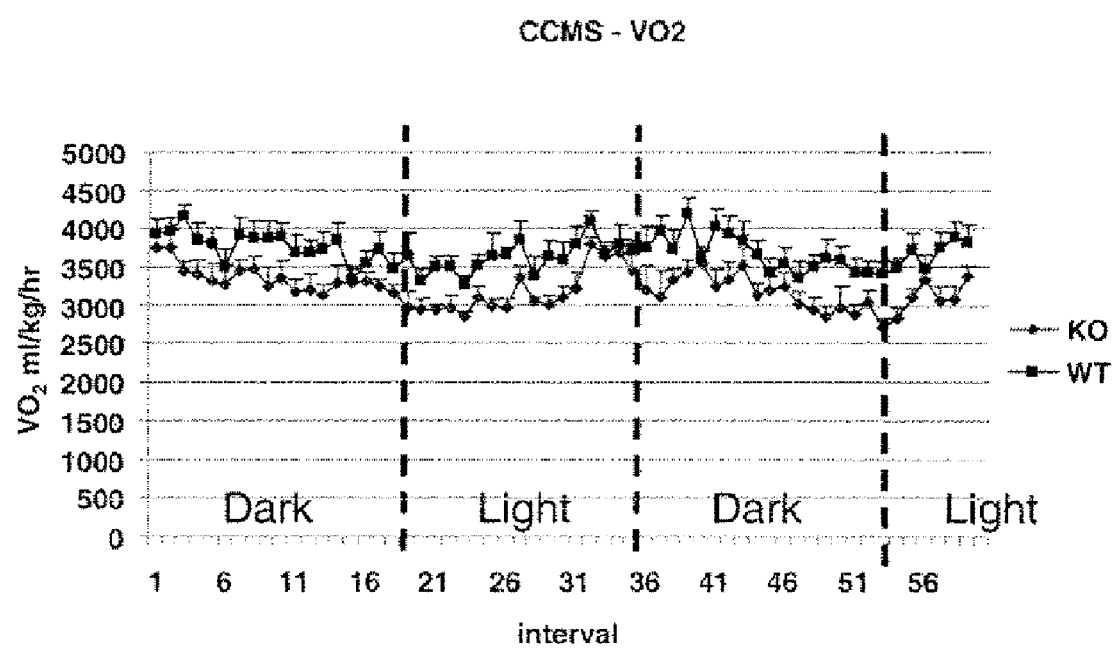
FIG. 18. Metabolic measures by time interval in the Comprehensive Cage Monitoring System (CCMS). The time required for a single round of gas measurements in all 16 chambers of the CCMS (on average, 48 minutes) was defined as an interval. The results are presented as mean±SEM with the dark and light phases separated by dashed lines. (A) Time interval comparison of oxygen consumption by the KO and WT mice. (B) Time interval comparison of carbon dioxide production by the KO and WT mice. (C) Time interval comparison of the respiratory exchange ratio (RER) for the KO and WT mice. (D) Time interval comparison of the heat produced by the KO and WT mice.
Figure 18B:
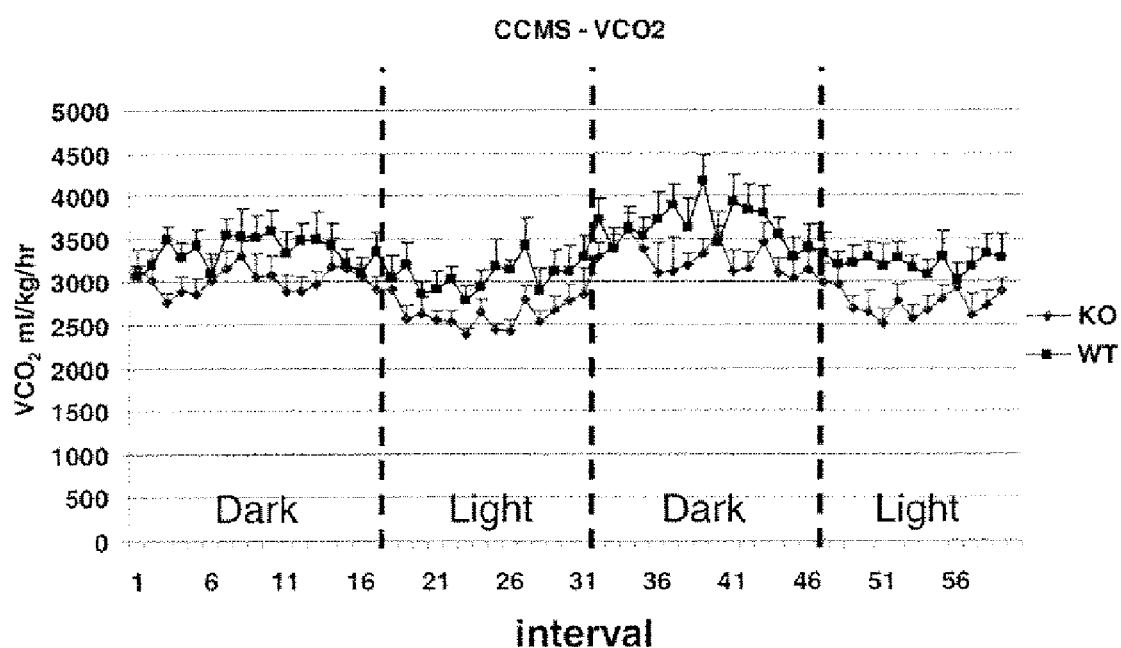
Figure 18C:
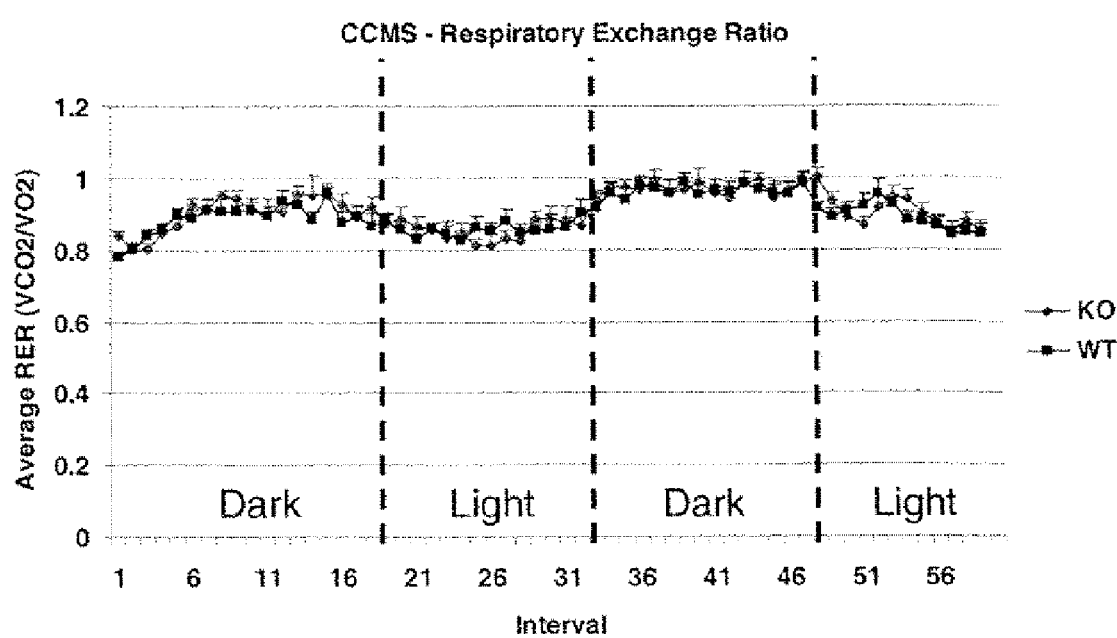
Figure 18D:
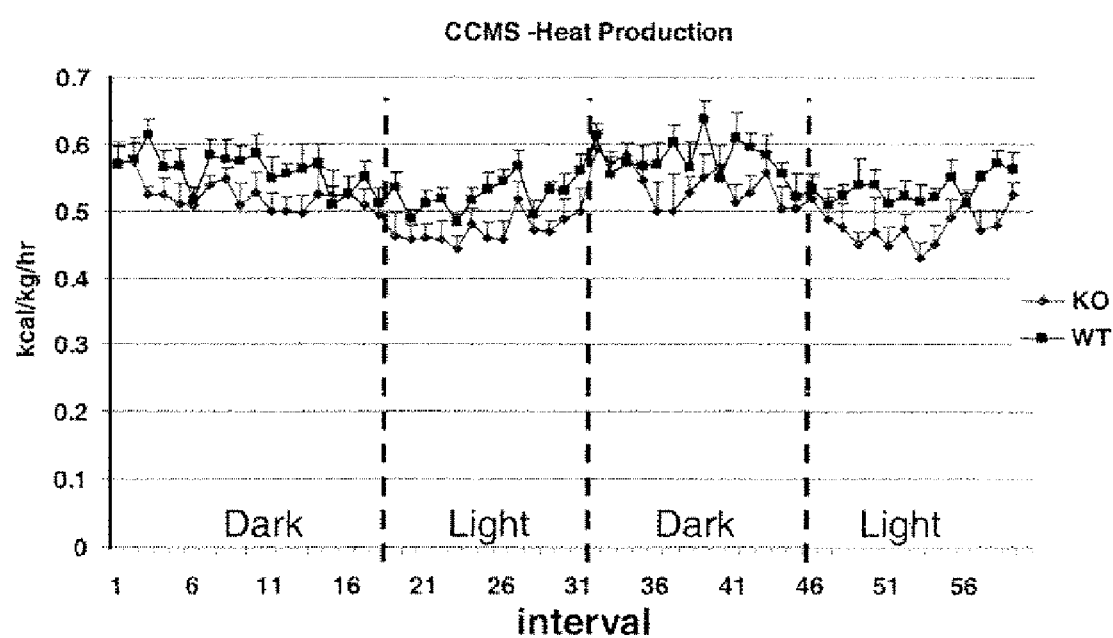
Figure 19:
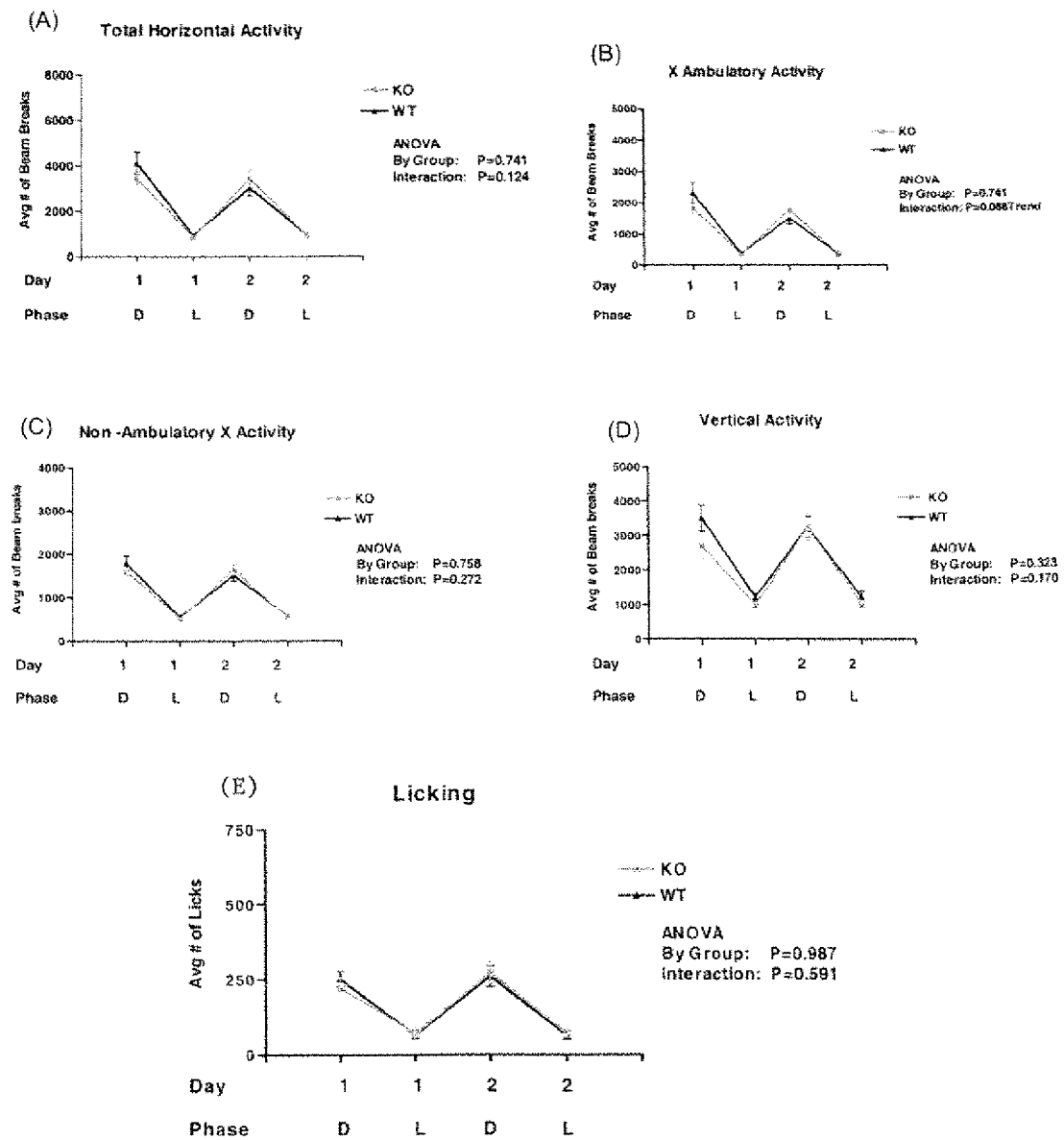
FIG. 19. Activity measures by photoperiod in the Comprehensive Cage Monitoring System (CCMS). The activity endpoints were measured for 48 hours in 12-hour photoperiods. The results are presented as mean±SEM with the data summed for the dark (D) and light (L) phases. (A) Comparison of total horizontal activity did not reveal a significant difference between the WT and KO mice (P=0.741). (B) Comparison of ambulatory horizontal (X) activity did not reveal a significant difference between the WT and KO mice (P=0.741), although there appeared to be a trend towards an interaction between the light phase and X ambulatory activity ($F_{3,42}$=2.33, P=0.088). (C) Comparison of non-ambulatory horizontal (X) activity did not reveal a significant difference between the WT and KO mice (P=0.758). (D) Comparison of vertical activity did not reveal a significant difference between the WT and KO mice (P=0.323). (E) Comparison of licking frequency did not reveal a significant difference between the WT and KO mice (P=0.987).
Figure 20A:
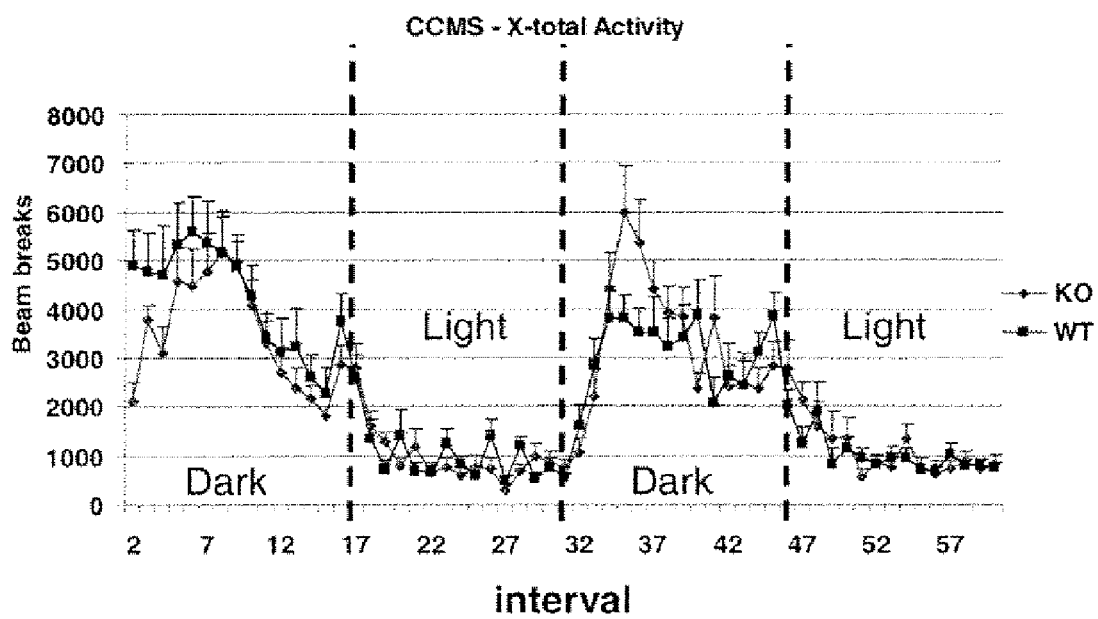
FIG. 20. Activity measures by time interval in the Comprehensive Cage Monitoring System (CCMS). The results are presented as mean±SEM with the dark and light phases separated by dashed lines. (A) Time interval comparison of total horizontal (X) activity by the KO and WT mice. (B) Time interval comparison of ambulatory horizontal (X) activity by the KO and WT mice. (C) Time interval comparison of non-ambulatory horizontal (X) activity by the KO and WT mice. (D) Time interval comparison of vertical activity by the KO and WT mice. (E) Time interval comparison of licking frequency by the KO and WT mice.
Figure 20B:
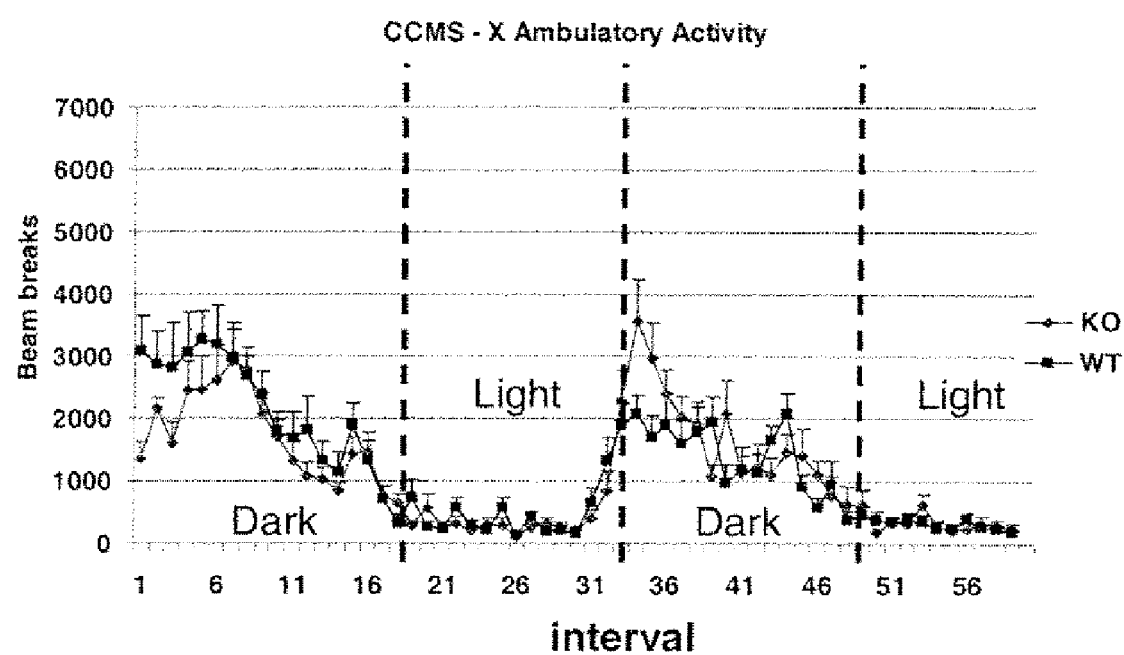
Figure 20C:
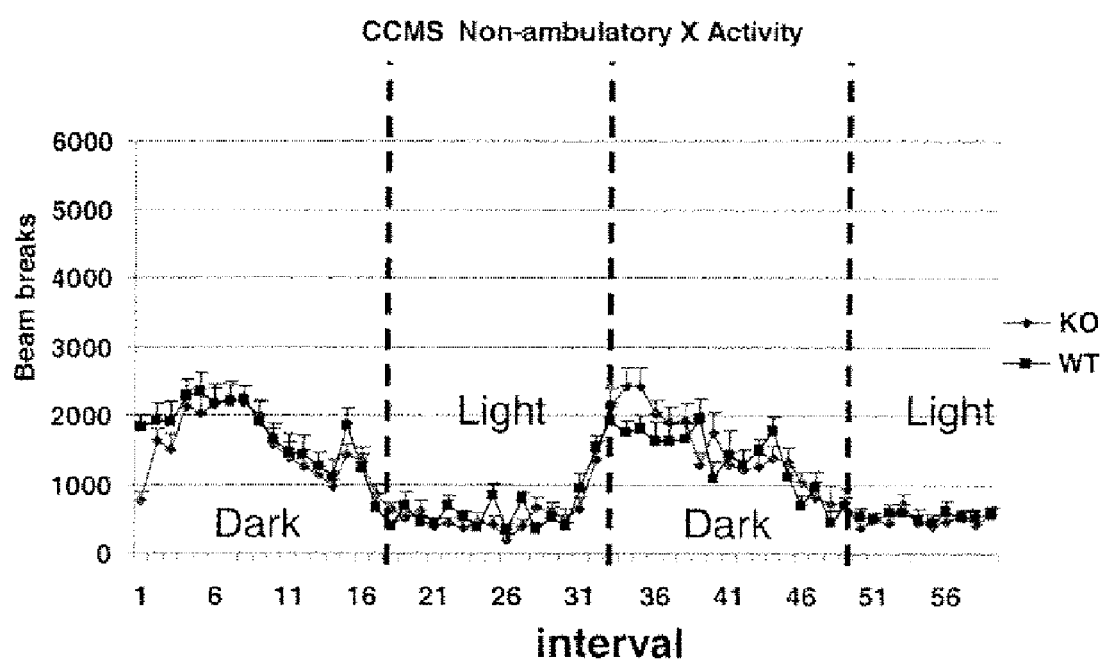
Figure 20D:
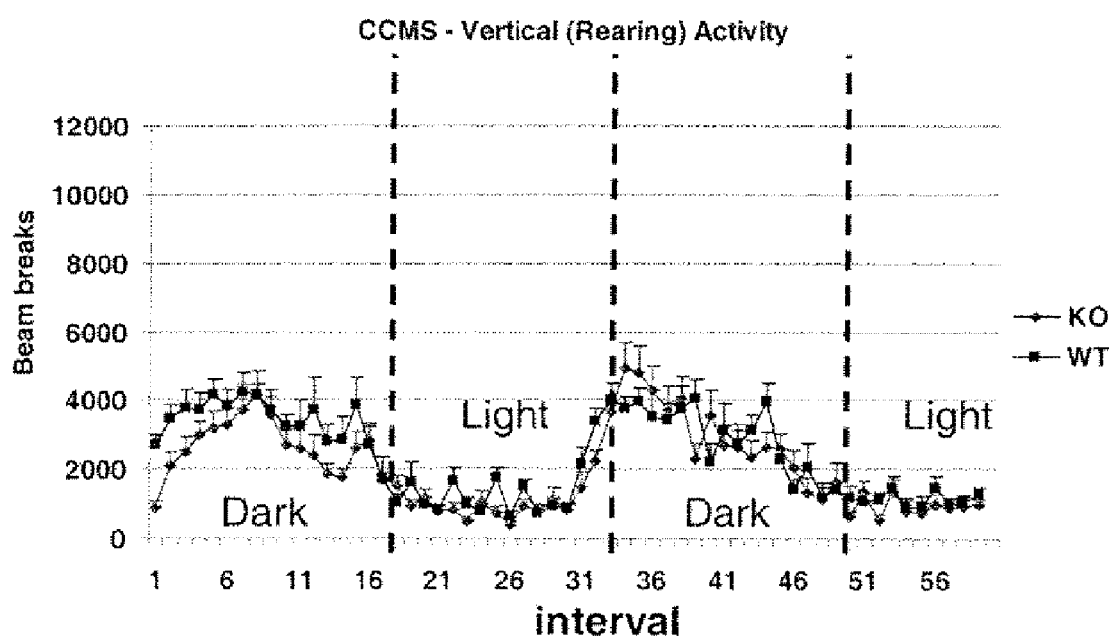
Figure 20E:
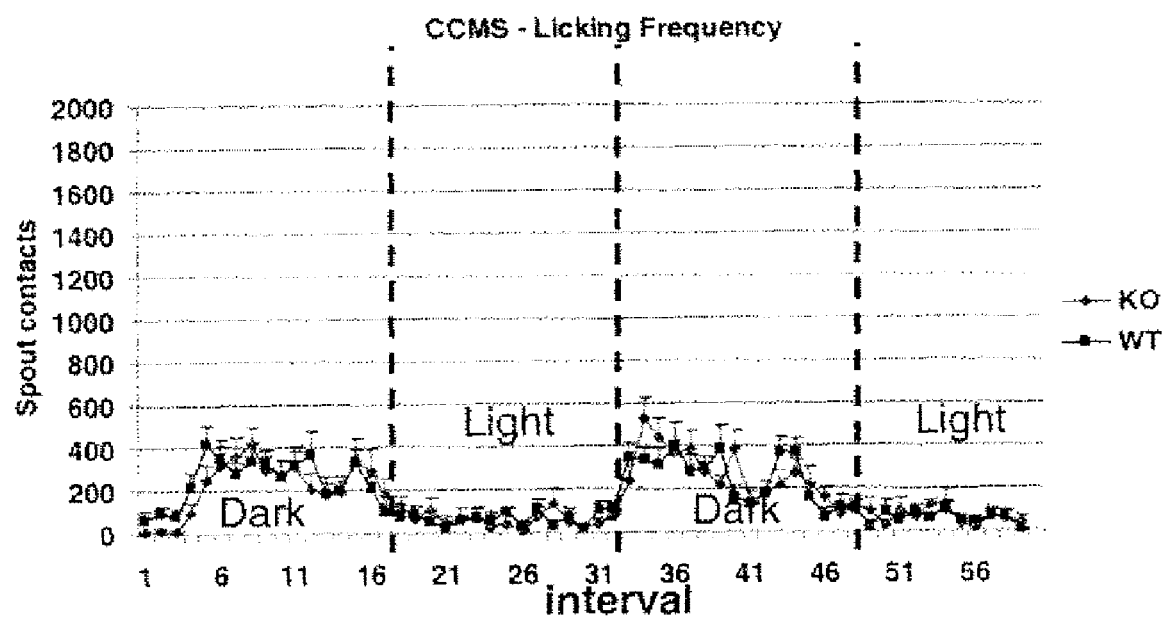

The following endpoints were included:
Total horizontal activity
Ambulatory horizontal activity
Non-ambulatory horizontal activity
Vertical activity
Licking frequency Results of Comprehensive Cage Monitoring System—Metabolic Measures By Photoperiod Analysis of the metabolic endpoints in the CCMS revealed a decrease in the metabolic rate in the KO group compared to that of the controls, as evidenced by lower oxygen consumption ($F_{1,13}$=10.34, P=0.007, FIG. 17A), $CO_2$ production ($F_{1,13}$=5.28, P=0.039, FIG. 17B) and decreased heat production ($F_{1,13}$=10.70, P=0.006, FIG. 17D) by the KO group. The RER quotient did not differ significantly between genotypes (FIG. 17C). The results are presented as mean±SEM with the data summed for the dark (D) phases and the light (L) phases.

Results of Comprehensive Cage Monitoring System—Metabolic Measures by Time Interval The results are presented as mean±SEM with dark and light phases demarked with a dashed line (FIGS. 18A-18D), Results of Comprehensive Cage Monitoring System—Activity Measures by Photoperiod Analysis of the activity endpoints (measured for 48 hours in 12-hour photoperiods) revealed no significant differences between genotypes in any of the measurements (FIGS. 19A-19E). There did appear to be a trend towards an interaction between the light phase and ambulatory activity in the X (horizontal) plane ($F_{3,42}$=2.33, P=0.088, FIG. 19B). This is most clearly observed in the data graphed in time intervals where the KO mice were less active than WTs in the dark phase immediately after being placed in the cage, but activity of the KOs at the beginning of the second dark phase were higher than that of the WTs. The results are presented as mean±SEM with the data summed for the dark (D) phases and the light (L) phases.

Results of Comprehensive Cage Monitoring System—Activity Measures by Time Interval The results are presented as means±SEM, with the dark and light phases demarked with a dashed line (FIGS. 20A-20E).

Conclusions

The results from the CCMS study found that the KO mice had reduced metabolic activity compared to the WT controls. However, this reduced metabolic activity was not correlated with a reduced level of activity as measured in the activity measures in the CCMS. Minor changes were found in horizontal ambulatory activity, but they do not explain the reduced metabolic activity. There were no differences between the genotypes in rearing activity or contact with the drinking spout.

Example 24

GPR26 Knockout Mice

Hematology of the Peripheral Blood 20-22 week old male GPR26 KO and Box 129 WT mice were used for this assay (5 mice per genotype). Blood was collected via the retro-orbital vein under isoflurane anesthesia. The hematological analysis of the peripheral blood obtained from five KU and five WT mice was performed on the Hemavet Multispecies Hematology Analyzer (CDC Technologies). An unpaired t-test (GraphPad Prism) was used to analyze differences between genotypes for each parameter.

Results

There were no statistically significant differences between the KO and WT groups for any cell types.

Example 25

GPR26 Knockout Mice

Clinical Blood Chemistries 20-22 week old male mice were used for this assay (eight animals per genotype). The mice were maintained on a reverse Light:Dark cycle (12 hours on:12 hours off) in a barrier facility. Food and water were available ad libitum. Blood was collected via cardiac puncture under Isoflurane anesthesia. The collected blood was allowed to coagulate for 30 minutes at room temperature and then centrifuged at 1000 g for 15 minutes at 4° C. The serum was analyzed on an ACE clinical chemistry analyzer (Alfa Wassermann) using the manufacturer's reagents according to the manual. An unpaired t-test (GraphPad Prism) was used to analyze differences between the groups of mice for each parameter. The following analytes were tested: Albumin, total protein, alkaline phosphatase, alanine aminotransferase, aspartate aminotransferase, lactate dehydrogenase, amylase, creatinine kinase, blood urea nitrogen, calcium, total bilirubin, creatinine, triglycerides, lactate, phosphorus, uric acid, magnesium, thyroxine, sodium, potassium, chloride, globulin, and A/G ratio.

Results

There were no statistically significant differences between the KO and WT groups with respect to any of the tested analytes. However, differences between the group means in three chemistries approached statistical significance ($P \leq 0.1$):

| Analyte | Group Unit | KO Mean | KO SD | WT Mean | WT SD | P-value |
|---|---|---|---|---|---|---|
| Amylase | u/L | 1026.50 | 75.21 | 1399.38 | 534.94 | 0.071 |
| Thyoxine | ug/dL | 4.81 | 0.46 | 5.19 | 0.38 | 0.095 |
| Chloride | mmol/L | 110.40 | 2.70 | 108.25 | 1.67 | 0.101 |

The decrease in thyroxine levels in the KO mice may be related to their lower metabolism.

Example 26

GPR26 Knockout Mice

Selected Organ Weights 19-22 week old male and female mice were used for this assay (eight males and three females per genotype). Prior to the experiment, the mice were maintained on a reverse Light:Dark cycle (12 hours on:12 hours off) in a barrier facility. Food and water were available ad libitum. To collect the tissues, the mice were euthanized by an overdose of inhaled Isoflurane. The following organs were dissected and weighed: the gastrocnemius muscle, liver, spleen, right kidney (the capsule stripped), heart, and trachea and lungs as one unit. An unpaired t-test (GraphPad prism) was used to analyze differences between the groups of mice for each parameter. Males and females were analyzed separately.

Results

There were no significant differences in organ weights between the KO and WT males. The KO females, however, appeared to have smaller hearts (P=0.0231) and livers (P=0.0087).

Discussion

Until the time of this invention, there had been no reports regarding the identification of any ligands or molecules with ability to activate GPR78 or GPR26. This report identifies certain isoflavones as activating ligands for GPR78 and GPR26. This report also identifies certain antagonists of GPR78 and GPR26.

Genistein is able to stimulate intracellular cAMP production in cells expressing GPR78 or GPR26. Stimulation of GPR78-mediated cAMP production by genistein is ligand/receptor-specific. However, there may be other naturally occurring ligands in human and other mammals for the GPR78 polypeptide and/or the GPR26 polypeptide. More extensive screening of collections of a variety of known molecules or tissue extracts to identify other potential ligands for GPR78 and GPR26 can be performed using only routine experimentation according to the methods described herein.

The signal transduction pathway for genistein-activated GPR78 and GPR26 is linked to the Gs protein family. The restrictive Gs-only signaling by GPR78 indicates a selective action of genistein through GPR78 and GPR26. This provides a highly regulated pathway for genistein to exert a selective set of physiological functions. Maggiolini M. et al described ability of genistein to activate GPR30 through a $G_{\beta\gamma}$ gamma-mediated pathway with potency in the low µM range ([25]). Therefore, the action of genistein on GPR30 appears to be distinctively different from that on GPR78 [29]; [30]. Activation of GPR30 by both estrogen and genistein suggest that GPR30 mediates at least some of the estrogen-like functions of genistein. In contrast, GPR78 is activated by genistein but not estrogen, suggesting that GPR78 mediates some of the genistein functions independent of those of estrogen.

The widespread expression of GPR78 is consistent with genistein's variety of physiological functions. Detection of GPR78 in placenta and pituitary gland ([19]) as well as in urethra, nasal and oral mucosa, esophagus, tonsil and joint tissue (FIG. 9A) indicates that genistein may mediate through activation of GPR78 hormone-related processes, inflammatory states, and pathways in the digestive system. Detection of GPR78 expression in cortex, amygdala, putamen, hippocampus, VTA and cerebellum (FIG. 9A) suggests that GPR78 may regulate functions in the central nervous systems as well, which may provide a mechanism for treating these disorders. GPR26 expression is more restricted in the brain regions in human (FIG. 9B). This data suggests an action of genistein mediated by GPR26 in the central nervous system. Genistein has been shown to exert a number of neurological functions in the central nervous system, including learning and memory, anxiety, and other behaviors ([32]; [33]; [34]). Genistein has also been implicated in stress and pain modulation ([35]) as well as in modulation of neurotransmitters such as serotonin and acetylcholine ([36]; [37]). Expression of both GPR78 and GPR26 abundantly in the brain suggests roles of the two receptors in CNS functions modulated by genistein, which may or may not related to pathways of estrogen.

The data indicates that GPR78 and GPR26 are constitutively active GPCRs. Consistently, GPR26 has been found constitutively active by Lee et al. ([38]). In addition, Bresnick et al. ([39]) found that expression of GPR26 mediated by retrovirus resulted in a significantly higher basal level of cAMP.

In summary, certain isoflavones have been identified as activating ligands for the orphan GPR78 and GPR26 polypeptides with a signaling pathway restricted to Gs protein family. The identification of a ligand and for GPR78 and GPR26 will aid in understanding physiological functions of these receptors and the physiological roles that genistein mediates in central and peripheral systems, and in identifying compounds that could be used to treat or prevent GPR78- and/or GPR26-mediated disorders. In addition, the discovery provides tools for identification of receptor-specific agonists and antagonists that may prove useful pharmaceutical agents to treat various GPR78- and/or GPR26-mediated disorders, such as anxiety disorders and metabolic disorders.

Sequences:

SEQ ID NO:1 refers GenBank Accession No. NP_543009.

SEQ ID NO:2 refers to GenBank Accession No. NM_08019.

SEQ ID NO: 3 refers to GenBank Accession No. NP_703143.

SEQ ID NO: 4 refers to GenBank Accession No. NM_153442.

Abbreviations:
cAMP, 3',5'-cyclic adenosine monophosphate
cre, cAMP response element
luc, luciferase
GPR, guanine nucleotide binding proteins-coupled receptor
H89, N-[2-(p-bromocinnamylamino) ethyl]-5-isoquinolinesulfonamide dihydrochloride
SQ22536, 9-(Tetrahydro-2-furanyl)-9H-purin-6-amine
MDL-12,330A, cis-N-(2-Phenylcyclopentyl)-azacyclotridec-1-en-2-amine hydrochloride
IBMX, 3-isobutyl-1-methylxanthine

REFERENCES

1. Sarkar, F. H., et al., *The role of genistein and synthetic derivatives of isoflavone in cancer prevention and therapy*. Mini Rev Med Chem, 2006. 6(4): p. 401-7.
2. Altavilla, D., et al., *Cardiovascular effects of the phytoestrogen genistein*. Curr Med Chem Cardiovasc Hematol Agents, 2004. 2(2): p. 179-86.
3. Cotter, A. and K. D. Cashman, *Genistein appears to prevent early postmenopausal hone loss as effectively as hormone replacement therapy*. Nutr Rev, 2003. 61(10): p. 346-51.
4. Albertazzi, P., S. A. Steel, and M. Bottazzi, *Effect of pure genistein on bone markers and hot flushes*. Climacteric, 2005. 8(4): p. 371-9.
5. Cruz, M. N., et al., *Acute responses to phytoestrogens in small arteries from men with coronary heart disease*. Am J Physiol Heart Circ Physiol, 2006. 290(5): p. H1969-75.
6. Kousidou, O., G. N. Tzanakakis, and N. K. Karamanos, *Effects of the natural isoflavonoid genistein on growth, signaling pathways and gene expression of matrix macromolecules by breast cancer cells*. Mini Rev Med Chem, 2006. 6(3): p. 331-7.
7. Ariazi, E. A. and V. C. Jordan, *Estrogen-related receptors as emerging targets in cancer and metabolic disorders*. Curr Top Med Chem, 2006. 6(3): p. 203-15.
8. Bektic, J., et al., *Molecular effects of the isoflavonoid genistein in prostate cancer*. Clin Prostate Cancer, 2005. 4(2): p. 124-9.
9. Rufer, C. E. and S. E. Kulling, *Antioxidant activity of isoflavones and their major metabolites using different in vitro assays*. J Agric Food Chem, 2006. 54(8): p. 2926-31.
10. Lee, J. S., *Effects of soy protein and genistein on blood glucose, antioxidant enzyme activities, and lipid profile in streptozotocin-induced diabetic rats*. Life Sci, 2006.
11. Valachovicova, T., V. Slivova, and D. Sliva, *Cellular and physiological effects of soy flavonoids*. Mini Rev Med Chem, 2004. 4(8): p. 881-7.
12. Akiyama, T., et al., *Genistein, a specific inhibitor of tyrosine-specific protein kinases*. J Biol Chem, 1987. 262 (12): p. 5592-5.
13. Nakashima, S., T. Koike, and Y. Nozawa, *Genistein, a protein tyrosine kinase inhibitor, inhibits thromboxane A2-mediated hµMan platelet responses*. Mol Pharmacol, 1991. 39(4): p. 475-80.
14. Dubey, R. K., et al., *Phytoestrogens inhibit growth and MAP kinase activity in hµMan aortic smooth muscle cells*. Hypertension, 1999. 33(1 Pt 2): p. 177-82.
15. Fotsis, T., et al., *Genistein, a dietary ingested isoflavonoid, inhibits cell proliferation and in vitro angiogenesis*. J Nutr, 1995. 125(3 Suppl): p. 790S-797S.

16. Liu, D., et al., *Genistein acutely stimulates insulin secretion in pancreatic beta-cells through a cAMP-dependent protein kinase pathway.* Diabetes, 2006. 55(4): p. 1043-50.
17. Liu, D., H. Jiang, and R. W. Grange, *Genistein activates the 3',5'-cyclic adenosine monophosphate signaling pathway in vascular endothelial cells and protects endothelial barrier function.* Endocrinology, 2005. 146(3): p. 1312-20.
18. Szkudelski, T., et al., *Genistein restricts leptin secretion from rat adipocytes.* J Steroid Biochem Mol Biol, 2005. 96(3-4): p. 301-7.
19. Lee, D. K., et al., *Discovery and mapping of ten novel G protein-coupled receptor genes.* Gene, 2001. 275(1): p. 83-91.
20. Underwood, S. L., et al., *Association analysis of the chromosome 4p-located G protein-coupled receptor 78 (GPR78) gene in bipolar affective disorder and schizophrenia.* Mol Psychiatry, 2006. 11(4): p. 384-94.
21. Jiang, Y., et al., *Identification and characterization of a novel RF-amide peptide ligand for orphan G-protein-coupled receptor SP9155.* J Biol Chem, 2003. 278(30): p. 27652-7.
22. Geissler, J. F., et al., *Thiazolidine-diones. Biochemical and biological activity of a novel class of tyrosine protein kinase inhibitors.* J Biol Chem, 1990. 265(36): p. 22255-61.
23. Behbod, F., et al., *Concomitant inhibition of Janus kinase 3 and calcineurin-dependent signaling pathways synergistically prolongs the survival of rat heart allografts.* J Immunol, 2001. 166(6): p. 3724-32.
24. Bilder, G. E., et al., *Tyrphostins inhibit PDGF-induced DNA synthesis and associated early events in smooth muscle cells.* Am J Physiol, 1991. 260(4 Pt 1): p. C721-30.
25. Maggiolini, M., et al., *The G protein-coupled receptor GPR30 mediates c-fos up-regulation by 17beta-estradiol and phytoestrogens in breast cancer cells.* J Biol Chem, 2004. 279(26): p. 27008-16.
26. Xu, Y. L., et al., *Neuropeptide S: a neuropeptide promoting arousal and anxiolytic-like effects.* Neuron, 2004. 43(4): p. 487-97.
27. Chijiwa, T., et al., *Inhibition of forskolin-induced neurite outgrowth and protein phosphorylation by a newly synthesized selective inhibitor of cyclic AMP-dependent protein kinase, N-[2-(p-bromocinnamylamino)ethyl]-5-isoquinolinesulfonamide (H-891), of PC12D pheochromocytoma cells.* J Biol Chem, 1990. 265(9): p. 5267-72.
28. Lippe, C. and C. Ardizzone, *Actions of vasopressin and isoprenaline on the ionic transport across the isolated frog skin in the presence and the absence of adenyl cyclase inhibitors MDL12330A and SQ22536.* Comp Biochem Physiol C, 1991. 99(1-2): p. 209-11.
29. Thomas, P., et al., *Identity of an estrogen membrane receptor coupled to a G protein in huMan breast cancer cells.* Endocrinology, 2005. 146(2): p. 624-32.
30. Revankar, C. M., et al., *A transmembrane intracellular estrogen receptor mediates rapid cell signaling.* Science, 2005. 307(5715): p. 1625-30.
31. Liu, D., L. L. Homan, and J. S. Dillon, *Genistein acutely stimulates nitric oxide synthesis in vascular endothelial cells by a cyclic adenosine 5'-monophosphate-dependent mechanism.* Endocrinology, 2004. 145(12): p. 5532-9.
32. Lephart, E. D., et al., *Neurobehavioral effects of dietary soy phytoestrogens.* Neurotoxicol Teratol, 2002. 24(1): p. 5-16.
33. Simon, N. G., et al., *Increased aggressive behavior and decreased affiliative behavior in adult male monkeys after long-term consumption of diets rich in soy protein and isoflavones.* Horm Behav, 2004. 45(4): p. 278-84.
34. Lund, T. D. and E. D. Lephart, *Dietary soy phytoestrogens produce anxiolytic effects in the elevated plus-maze.* Brain Res, 2001. 913(2): p. 180-4.
35. Lephart, E. D., E. Galindo, and L. H. Bu, *Stress (hypothalamic-pituitary-adrenal axis) and pain response in male rats exposed lifelong to high vs. low phytoestrogen diets.* Neurosci Lett, 2003. 342(1-2): p. 65-8.
36. Shively, C. A., et al., *Soy and social stress affect serotonin neurotransmission in primates.* Pharmacogenomics J, 2003. 3(2): p. 114-21.
37. Pan, Y., M. Anthony, and T. B. Clarkson, *Effect of estradiol and soy phytoestrogens on choline acetyltransferase and nerve growth factor mRNAs in the frontal cortex and hippocampus of female rats.* Proc Soc Exp Biol Med, 1999. 221(2): p. 118-25.
38. Lee, D. K., et al., *Cloning and characterization of additional members of the G protein-coupled receptor family.* Biochim Biophys Acta, 2000. 1490(3): p. 311-23.
39. Bresnick, J. N., et al., *Identification of signal transduction pathways used by orphan g protein-coupled receptors.* Assay Drug Dev Technol, 2003. 1(2): p. 239-49.
40. D. J. Stuehr et al., *Inhibition of macrophage and endothelial cell nitric oxide synthase by diphenyleneiodonium and its analogs.* FASEB J., 1991.5: p. 98.
41. A. R. Cross and O. T. G. Jones, *The effect of the inhibitor diphenylene iodonium on the superoxide-generating system of neutrophils. Specific labelling of a component polypeptide of the oxidase.* Biochem. J., 1986. 237: p. 111.
42. J. T. Hancock and O. T. G. Jones, *The inhibition by diphenyleneiodonium and its analogues of superoxide generation by macrophages.* Biochem. J., 1987. 242: p. 103.
43. D. Walterova et al., *Benzo[c]phenanthridine alkaloids sanguinarine and chelerythrine: biological activities and dental care applications.* Acta Univ. Palacky Olomouc Fac. Med., 1995. 139: pp. 7-16.
44. *Quaternary isoquinoline alkaloids sanguinarine and chelerythrine. In vitro and in vivo effects.* Chemicke Listy 100, 2006. 100: pp. 30-41.
45. M. Das and S. K. Khanna, *Clinicoepidemiological, toxicological, and safety evaluation studies on argemone oil.* Crit. Rev. Toxicol., 1997. 27: pp. 273-297.
46. M. Lopus and D. Panda, *The benzophenanthridine alkaloid sanguinarine perturbs microtubule assembly dynamics through tubulin binding. A possible mechanism for its antiproliferative activity.* FEBS J., 2006. 273(10): pp. 2139-2150).

We claim:

1. A method for identifying a modulator of the G protein-coupled receptor 78 (GPR78) or G protein-coupled receptor 26 (GPR26) polypeptide, comprising:
   a) contacting the GPR78 or GPR26 polypeptide or a fragment thereof with a ligand of the GPR78 or GPR26 polypeptide in the presence and absence of a test sample, wherein the GPR78 or GPR26 ligand is selected from the group consisting of: isoflavone or an analog thereof, genistein or an analog thereof and daidzein or an analog of thereof; and
   b) measuring the activity of the GPR78 or GPR26 polypeptide, wherein a modulator of the GPR78 or GPR26 polypeptide in the test sample is identified by measuring a change in the activity of the GPR78 or GPR26 polypeptide in the presence and absence of the test sample.

2. The method of claim 1, wherein the GPR78 or GPR26 ligand is isoflavone or an analog thereof.

3. The method of claim 1, wherein the GPR78 or GPR26 ligand is genistein, daidzein, an analog of genistein or an analog of daidzein.

4. The method of claim 1, wherein the modulator is an agonist of the GPR78 or GPR26 polypeptide.

5. The method of claim 1, wherein the modulator is an antagonist of the GPR78 or GPR26 polypeptide.

* * * * *